(12) United States Patent
Hennequin et al.

(10) Patent No.: US 7,569,577 B2
(45) Date of Patent: Aug. 4, 2009

(54) QUINAZOLINE DERIVATIVES AS TYROSINE KINASE INHIBITORS

(75) Inventors: Laurent Francois Andre Hennequin, Reims (FR); Christopher Thomas Halsall, Macclesfield (GB)

(73) Assignee: Astrazeneca AB, Sodertalje (SE)

( * ) Notice: Subject to any disclaimer, the term of this patent is extended or adjusted under 35 U.S.C. 154(b) by 504 days.

(21) Appl. No.: 10/573,090

(22) PCT Filed: Sep. 13, 2004

(86) PCT No.: PCT/GB2004/003923

§ 371 (c)(1),
(2), (4) Date: Mar. 15, 2006

(87) PCT Pub. No.: WO2005/026150

PCT Pub. Date: Mar. 24, 2005

(65) Prior Publication Data

US 2007/0043009 A1 Feb. 22, 2007

(30) Foreign Application Priority Data

Sep. 16, 2003 (GB) .................... 0321620.7
Mar. 19, 2004 (GB) .................... 0406163.6

(51) Int. Cl.
*A61K 31/517* (2006.01)
*C07D 239/94* (2006.01)
(52) U.S. Cl. .................... 514/266.22; 544/293
(58) Field of Classification Search .......... 514/266.22; 544/293
See application file for complete search history.

(56) References Cited

U.S. PATENT DOCUMENTS

| | | | |
|---|---|---|---|
| 3,812,257 A | 5/1974 | Yamamoto | 514/266.21 |
| 3,971,783 A | 7/1976 | Barnish et al. | 514/284 |
| 4,335,127 A | 6/1982 | Vandenberk et al. | 514/266.22 |
| 4,921,863 A | 5/1990 | Sugimoto et al. | 514/319 |
| 5,411,963 A | 5/1995 | Dreikorn et al. | 514/266.3 |
| 5,457,105 A | 10/1995 | Barker | 514/234.5 |
| 5,616,582 A | 4/1997 | Barker | 514/234.5 |
| 5,747,498 A | 5/1998 | Schnur et al. | 514/266.4 |
| 5,770,599 A | 6/1998 | Gibson | 514/228.2 |
| 5,817,678 A | 10/1998 | Kim et al. | 514/326 |
| 6,127,366 A | 10/2000 | Kim et al. | 514/235.5 |
| 6,177,433 B1 | 1/2001 | Uckun et al. | 514/266.4 |
| 6,200,976 B1 | 3/2001 | Ries et al. | 514/249 |
| 6,297,258 B1 | 10/2001 | Wissner et al. | 514/313 |
| 6,313,127 B1 | 11/2001 | Waterson et al. | 514/253.01 |
| 6,541,491 B1 | 4/2003 | Davies et al. | 514/340 |
| 6,562,319 B2 | 5/2003 | Mishani et al. | 424/1.81 |
| 6,617,329 B2 | 9/2003 | Himmelsbach et al. | 514/252.14 |
| 6,653,305 B2 | 11/2003 | Himmelsbach et al. | 514/233.5 |
| 6,656,946 B2 | 12/2003 | Himmelsbach et al. | 514/266.4 |
| 6,740,651 B2 | 5/2004 | Himmelsbach et al. | 514/228.8 |
| 6,972,288 B1 | 12/2005 | Himmelsbach et al. | 514/234.8 |
| 7,148,230 B2 | 12/2006 | Bradbury et al. | |
| 2002/0049197 A1 | 4/2002 | Himmelsbach et al. | 514/217.06 |
| 2002/0082270 A1 | 6/2002 | Himmelsbach et al. | 514/266.2 |
| 2002/0082271 A1 | 6/2002 | Himmelsbach et al. | 514/266.24 |
| 2002/0128553 A1 | 9/2002 | Mishani et al. | 600/431 |
| 2002/0169180 A1 | 11/2002 | Himmelsbach et al. | 514/266.4 |
| 2002/0173509 A1 | 11/2002 | Himmelsbach et al. | 514/234.5 |
| 2002/0177601 A1 | 11/2002 | Himmelsbach et al. | 514/266.2 |
| 2003/0149062 A1 | 8/2003 | Jung et al. | 514/266.22 |
| 2003/0158196 A1 | 8/2003 | Jung et al. | 514/234.2 |
| 2003/0225079 A1 | 12/2003 | Singer et al. | 514/233.8 |
| 2004/0044014 A1 | 3/2004 | Himmelsbach et al. | 514/266.4 |
| 2004/0048880 A1 | 3/2004 | Himmelsbach et al. | 514/266.2 |
| 2004/0176361 A1 | 9/2004 | Fujio et al. | 514/224.2 |
| 2005/0043336 A1 | 2/2005 | Hennequin et al. | |

(Continued)

FOREIGN PATENT DOCUMENTS

DE 19908567 8/2000

(Continued)

OTHER PUBLICATIONS

Harris et al. "Systematic variation of a key quinazoline core" Presented at the XXII European Colloquium on Heterocyclic Chemistry (XXII ECHC-2006) Bari, Italy, Sep. 2-6, 2006.

(Continued)

*Primary Examiner*—James O Wilson
*Assistant Examiner*—Tamthom N Truong
(74) *Attorney, Agent, or Firm*—Morgan Lewis & Bockius LLP

(57) ABSTRACT

The invention concerns quinazoline derivatives of the Formula (I); wherein each of $R^1$, $R^2$, W, $X^1$, $X^2$, Z, a and b are as defined in the description; processes for their preparation; pharmaceutical compositions containing them and their use in the manufacture of a medicament for providing an antiproliferative effect. The quinazoline derivatives of Formula (I) are expected to be useful in the treatment of diseases such as certain cancers mediated by erbB receptor tyrosine kinases, particularly EGFR tyrosine kinase.

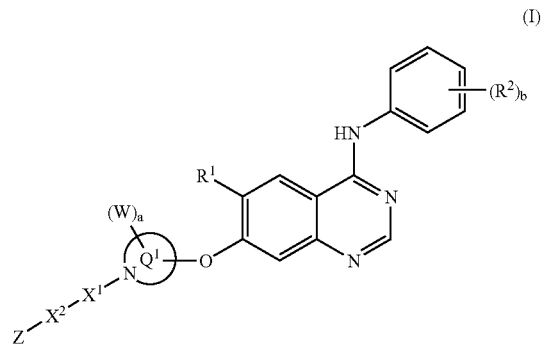

18 Claims, No Drawings

U.S. PATENT DOCUMENTS

| | | |
|---|---|---|
| 2005/0054662 A1 | 3/2005 | Hennequin et al. |
| 2005/0148607 A1 | 7/2005 | Suzuki et al. .......... 514/264.11 |
| 2005/0165035 A1 | 7/2005 | Bradbury et al. ....... 514/266.22 |
| 2005/0215574 A1 | 9/2005 | Bradbury et al. |
| 2006/0211714 A1 | 9/2006 | Hennequin et al. |
| 2006/0287295 A1 | 12/2006 | Barlaam et al. |
| 2007/0015743 A1 | 1/2007 | Bradbury et al. |
| 2007/0032508 A1 | 2/2007 | Bradbury et al. |
| 2007/0032513 A1 | 2/2007 | Hennequin et al. |
| 2007/0037837 A1 | 2/2007 | Hennequin et al. |
| 2007/0043010 A1 | 2/2007 | Bradbury et al. |
| 2007/0082921 A1 | 4/2007 | Hennequin et al. |
| 2007/0088044 A1 | 4/2007 | Hennequin et al. |
| 2007/0099943 A1 | 5/2007 | Bradbury et al. |
| 2007/0149546 A1 | 6/2007 | Bradbury et al. |
| 2007/0232607 A1 | 10/2007 | Bradbury et al. |
| 2007/0244136 A1 | 10/2007 | Hennequin et al. |
| 2007/0293490 A1 | 12/2007 | Delouvrie et al. |

FOREIGN PATENT DOCUMENTS

| | | |
|---|---|---|
| DE | 10040527 | 2/2002 |
| EP | 0 288 563 | 5/1994 |
| EP | 0 669 324 | 8/1995 |
| EP | 0 566 226 | 11/1995 |
| EP | 0 837 063 | 4/1998 |
| EP | 1 044 969 | 10/2000 |
| EP | 0 585 371 | 4/2002 |
| EP | 1 230 919 | 8/2002 |
| EP | 1 369 418 | 12/2003 |
| EP | 1 548 008 | 6/2005 |
| GB | 2295387 | 5/1996 |
| WO | WO 88/02365 | 4/1988 |
| WO | WO 92/20642 | 11/1992 |
| WO | WO 95/00146 | 1/1995 |
| WO | WO 95/15758 | 6/1995 |
| WO | WO 96/09294 | 3/1996 |
| WO | WO 96/30347 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 97/03069 | 1/1997 |
| WO | WO 97/06138 | 2/1997 |
| WO | WO 97/18813 | 5/1997 |
| WO | WO 97/22596 | 6/1997 |
| WO | WO 97/28128 | 8/1997 |
| WO | WO 97/30034 | 8/1997 |
| WO | WO 97/30035 | 8/1997 |
| WO | WO 97/30044 | 8/1997 |
| WO | WO 97/32856 | 9/1997 |
| WO | WO 97/38983 | 10/1997 |
| WO | WO 97/38994 | 10/1997 |
| WO | WO 98/02434 | 1/1998 |
| WO | WO 98/13354 | 4/1998 |
| WO | WO 98/38984 | 9/1998 |
| WO | WO 99/06378 | 2/1999 |
| WO | WO 99/35132 | 7/1999 |
| WO | WO 99/54313 | 10/1999 |
| WO | WO 00/09481 | 2/2000 |
| WO | WO 00/10981 | 3/2000 |
| WO | WO 00/12497 | 3/2000 |
| WO | WO 00/18740 | 4/2000 |
| WO | WO 00/20402 | 4/2000 |
| WO | WO 00/21955 | 4/2000 |
| WO | WO 00/24718 | 5/2000 |
| WO | WO 00/31048 A | 6/2000 |
| WO | WO 00/44728 | 8/2000 |
| WO | WO 00/47212 | 8/2000 |
| WO | WO 00/51991 | 9/2000 |
| WO | WO 00/55141 A | 9/2000 |
| WO | WO 00/56720 | 9/2000 |
| WO | WO 00/78735 | 12/2000 |
| WO | WO 01/07432 | 2/2001 |
| WO | WO 01/19788 | 3/2001 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | WO 01/32651 A | 5/2001 |
| WO | WO 01/77085 | 10/2001 |
| WO | WO 01/94341 A | 12/2001 |
| WO | WO 01/98277 | 12/2001 |
| WO | WO 02/16352 | 2/2002 |
| WO | WO 02/18351 | 3/2002 |
| WO | WO 02/18370 | 3/2002 |
| WO | WO 02/18372 | 3/2002 |
| WO | WO 02/18373 | 3/2002 |
| WO | WO 02/18376 | 3/2002 |
| WO | WO 02/24684 | 3/2002 |
| WO | WO 02/30924 | 4/2002 |
| WO | WO 02/34744 | 5/2002 |
| WO | WO 02/41882 | 5/2002 |
| WO | WO 02/44166 | 6/2002 |
| WO | WO 02/48117 | 6/2002 |
| WO | WO 02/50043 | 6/2002 |
| WO | WO 02/056882 | 7/2002 |
| WO | WO 02/062767 | 8/2002 |
| WO | WO 02/066445 | 8/2002 |
| WO | WO 02/068409 | 9/2002 |
| WO | WO 02/073235 | 9/2002 |
| WO | WO 02/076976 | 10/2002 |
| WO | WO 02/092577 | 11/2002 |
| WO | WO 02/092578 A | 11/2002 |
| WO | WO 02/097490 | 12/2002 |
| WO | WO 02/102315 | 12/2002 |
| WO | WO 03/000188 | 1/2003 |
| WO | WO 03/031406 | 4/2003 |
| WO | WO 03/040108 | 5/2003 |
| WO | WO 03/040109 A | 5/2003 |
| WO | WO 03/045364 | 6/2003 |
| WO | WO 03/045395 | 6/2003 |
| WO | WO 03/049740 | 6/2003 |
| WO | WO 03/066060 | 8/2003 |
| WO | WO 03/068264 | 8/2003 |
| WO | WO 03/082290 A | 10/2003 |
| WO | WO 03/082831 A | 10/2003 |
| WO | WO 03/089439 | 10/2003 |
| WO | WO 03/094921 | 11/2003 |
| WO | WO 03/099276 | 12/2003 |
| WO | WO 03/101491 | 12/2003 |
| WO | WO 2004/006846 | 1/2004 |
| WO | WO 2004/064718 | 8/2004 |
| WO | WO 2004/093880 | 11/2004 |
| WO | WO 2004/096226 | 11/2004 |
| WO | WO 2005/012290 | 2/2005 |
| WO | WO 2005/013998 | 2/2005 |
| WO | WO 2005/026151 | 3/2005 |
| WO | WO 2005/026152 | 3/2005 |
| WO | WO 2005/026156 | 3/2005 |
| WO | WO 2005/026157 | 3/2005 |
| WO | WO 2005/028469 | 3/2005 |
| WO | WO 2005/028470 | 3/2005 |
| WO | WO 2005/030757 | 4/2005 |
| WO | WO 2005/030765 | 4/2005 |
| WO | WO 2005/051923 | 6/2005 |
| WO | WO 2005/075439 | 8/2005 |
| WO | WO 2005/118572 | 12/2005 |
| WO | WO 2006/064196 | 6/2006 |
| WO | WO 2006/090163 | 8/2006 |
| WO | WO 2006/092573 | 9/2006 |
| WO | WO 2006/092574 | 9/2006 |

| WO | WO 2006/117521 | 11/2006 |
| WO | WO 2006/117523 | 11/2006 |
| WO | WO 2007/034143 | 3/2007 |
| WO | WO 2007/034144 | 3/2007 |
| WO | WO 2007/063291 | 6/2007 |
| WO | WO 2007/063293 | 6/2007 |

OTHER PUBLICATIONS

Tsou H-R, et al., "6-Substituted-4-(3-Bromophenylamino) Quina Zolines as Putative Irreversible Inhibitors of the Epidermal Growth Factor Receptor (EGFR) and Human Epidermal Growth Factor Receptor (HER-2) Tyrosine Kinases with Enhanced Antitumor Activity", 2001, Journal of Medicinal Chemistry, US, pp. 2719-2734.
Hennequin, Laurent F., et al., "Novel 4-Anilinoquinazolines with C-7 Basic Side Chains: Design and Structure Activity Relationship of a Series of Potent Orally Active, VEGF Receptor Tyrosine Kinase Inhibitors", Journal of Medicinal Chemistry, vol. 45, No. 6, pp. 1300-1312, 2002.
Small, Jeff B., et al., "Tyrosine Kinase Inhibitors. 17. Irreversible Inhibitors of the Epidermal Growth Factor Receptor . . . ", Journal of Medicinal Chemistry, vol. 43, No. 7, pp. 1380-1397, 2000.
Gaul, Micheal, et al., "Discovery and Biological Evaluation of Potent Dual ErB-2/Egfr Tyrosine Kinase Inhibitors: 6-Thiazolylquinazolines", Bioorganic & Medicinal Chemistry Letters, vol. 13, pp. 637-640, 2003.
Ballard et al. "Inhibitors of epidermal growth factor receptor tyrosine kinase: Novel C-5 substituted anilinoquinazolines designed to target the ribose pocket" Bioorg Med Chem Lett. 16(6):1633-1637 (2006).
Ballard et al. "5-Substituted 4-anilinoquinazolines as potent, selective and orally active inhibitors of erbB2 receptor tyrosine kinase" Bioorg Med Chem Lett. 15(19):4226-4229 (2005).
Ballard et al. "Inhibitors of epidermal growth factor receptor tyrosine kinase: optimisation of potency and in vivo pharmacokinetics" Bioorg Med Chem Lett. 16(18):4908-4912 (2006).
Harris et al. "Facile synthesis of 7-amino anilinoquinazolines via direct amination of the quinazoline core" Tetrahedron letters 46(43): 7381-7384 (2005).

Harris et al. "Selective alkylation of a 6,7-dihydroxyquinazoline" Tetrahedron letters 46(45):7715-7719 (2005).
Hennequin et al. "Novel 4-anilinoquinazolines with C-6 carbon-linked side chains: synthesis and structure-activity relationship of a series of potent, orally active, EGF receptor tyrosine kinase inhibitors" Bioorg Med Chem Lett. 16(10):2672-2676 (2006).
Gaul et al. "Discovery and Biological Evaluation of Potent Dual ErB-2/EGFR tyrosine Kinase Inhibitors:6-thiazolylquinazolines" Bioorganic & Medicinal Chemistry Letters 13: 637-640 (2003).
Hennequin et al. "Design and structure-activity relationship of a new class of potent VEGF receptor tyrosine kinase inhibitors" Journal Of Medicinal Chemistry 42:5369-5389 (1999).
Hennequin et al. "Novel 4-anilinoquinazolines with C-7 basic side chains : Design and structure activity relationship of a series of potent, orally active, VEGF receptor tyrosine kinase inhibitors" Journal Of Medicinal Chemistry 45(6):1300-1312 (2002).
Smaill et al. "Tyrosine kinase Inhibitors. 17. Irreversible Inhibitors of the Epidermal Growth Factor Receptor: 4-(phenylamino)quinazoline- and 4-(phenylamino0pyrido[3,2-d]pyrimidine-6-acrylamides bearing additional solubilizing function" Journal of Medicinal Chemistry 43(7):1380-1397 (2000).
Stamos et al. "Structure of the Epidermal Growth Factor Receptor Kinase Domain Alone and in Complex with a 4-Anilinoquinazoline Inhibitor" J. Biol. Chem. 277(48):46265-46272 (2002).
Traxler et al. "Protein tyrosine kinase inhibitors in cancer treatment" Exp. Opin. Ther. Patents 7(6):571-588 (1997).
Traxler et al. "Tyrosine kinase inhibitors in cancer treatment (Part II)" Exp. Opin. Ther. Patents 8(12):1599-1625 (1998).
Tsou et al. "6-Substituted-4-(3-bromophenylamino)quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity" J. Med. Chem. 44:2719-2734 (2001).
Vema et al. "Design of EGFR kinase inhibitors: a ligand-based approach and its confirmation with structure-based studies" Bioorg Med Chem. 11(21):4643-4653 (2003).

QUINAZOLINE DERIVATIVES AS TYROSINE KINASE INHIBITORS

The invention concerns certain novel quinazoline derivatives, or pharmaceutically acceptable salts, or pharmaceutically acceptable esters thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

Many of the current treatment regimes for diseases resulting from the abnormal regulation of cellular proliferation such as psoriasis and cancer, utilise compounds that inhibit DNA synthesis and cellular proliferation. To date, compounds used in such treatments are generally toxic to cells however their enhanced effects on rapidly dividing cells such as tumour cells can be beneficial. Alternative approaches to these cytotoxic anti-tumour agents are currently being developed, for example selective inhibitors of cell signalling pathways. These types of inhibitors are likely to have the potential to display an enhanced selectivity of action against tumour cells and so are likely to reduce the probability of the therapy possessing unwanted side effects.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors as well as paracrine and endocrine factors. By binding to specific transmembrane receptors, these ligands integrate the extracellular signal to the intracellular signalling pathways, therefore transducing the signal across the plasma membrane and allowing the individual cell to respond to its extracellular signals. Many of these signal transduction processes utilise the reversible process of the phosphorylation of proteins that are involved in the promotion of these diverse cellular responses. The phosphorylation status of target proteins is regulated by specific kinases and phosphatases that are responsible for the regulation of about one third of all proteins encoded by the mammalian genome. As phosphorylation is such an important regulatory mechanism in the signal transduction process, it is therefore not surprising that aberrations in these intracellular pathways result in abnormal cell growth and differentiation and so promote cellular transformation (reviewed in Cohen et al, *Curr Opin Chem Biol*, 1999, 3, 459-465).

It has been widely shown that a number of these tyrosine kinases are mutated to constitutively active forms and/or when over-expressed result in the transformation of a variety of human cells. These mutated and over-expressed forms of the kinase are present in a large proportion of human tumours (reviewed in Kolibaba et al, Biochimica et Biophysica Acta, 1997, 133, F217-F248). As tyrosine kinases play fundamental roles in the proliferation and differentiation of a variety of tissues, much focus has centred on these enzymes in the development of novel anti-cancer therapies. This family of enzymes is divided into two groups—receptor and non-receptor tyrosine kinases e.g. EGF Receptors and the SRC family respectively. From the results of a large number of studies including the Human Genome Project, about 90 tyrosine kinase have been identified in the human genome, of this 58 are of the receptor type and 32 are of the non-receptor type. These can be compartmentalised in to 20 receptor tyrosine kinase and 10 non-receptor tyrosine kinase subfamilies (Robinson et al, *Oncogene,* 2000, 19, 5548-5557).

The receptor tyrosine kinases are of particular importance in the transmission of mitogenic signals that initiate cellular replication. These large glycoproteins, which span the plasma membrane of the cell possess an extracellular binding domain for their specific ligands (such as Epidermal Growth Factor (EGF) for the EGF Receptor). Binding of ligand results in the activation of the receptor's kinase enzymatic activity that is encoded by the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., *EMBO J.,* 2000, 19, 3159). One mechanism in which this can be accomplished is by overexpression of the receptor at the protein level, generally as a result of gene amplification. This has been observed in many common human cancers (reviewed in Klapper et al., *Adv. Cancer Res.,* 2000, 77, 25) such as breast cancer (Sainsbury et al., *Brit. J. Cancer,* 1988, 58, 458; Guerin et al., *Oncogene Res.,* 1988, 3, 21; Slamon et al., *Science,* 1989, 244, 707; Klijn et al., *Breast Cancer Res. Treat.,* 1994, 29, 73 and reviewed in Salomon et al., *Crit. Rev. Oncol. Hematol.,* 1995, 19, 183), non-small cell lung cancers (NSCLCs) including adenocarcinomas (Cerny et al., *Brit. J. Cancer,* 1986, 54, 265; Reubi et al., *Int. J. Cancer,* 1990, 45, 269; Rusch et al., *Cancer Research,* 1993, 53, 2379; Brabender et al, *Clin. Cancer Res.,* 2001, 7, 1850) as well as other cancers of the lung (Hendler et al., *Cancer Cells,* 1989, 7, 347; Ohsaki et al., *Oncol. Rep.,* 2000, 7, 603), bladder cancer (Neal et al., *Lancet,* 1985, 366; Chow et al., *Clin. Cancer Res.,* 2001, 7, 1957, Zhau et al., *Mol Carcinog.,* 3, 254), oesophageal cancer (Mukaida et al., *Cancer,* 1991, 68, 142), gastrointestinal cancer such as colon, rectal or stomach cancer (Bolen et al., *Oncogene Res.,* 1987, 1, 149; Kapitanovic et al., *Gastroenterology,* 2000, 112, 1103; Ross et al., *Cancer Invest.,* 2001, 19, 554), cancer of the prostate (Visakorpi et al., *Histochem. J.,* 1992, 24, 481; Kumar et al., 2000, 32, 73; Scher et al., *J. Natl. Cancer Inst.,* 2000, 92, 1866), leukaemia (Konaka et al., *Cell,* 1984, 37, 1035, Martin-Subero et al., *Cancer Genet Cytogenet.,* 2001, 127, 174), ovarian (Hellstrom et al., *Cancer Res.,* 2001, 61, 2420), head and neck (Shiga et al., *Head Neck,* 2000, 22, 599) or pancreatic cancer (Ovotny et al., *Neoplasma,* 2001, 48, 188). As more human tumour tissues are tested for expression of the erbB family of receptor tyrosine kinases it is expected that their widespread prevalence and importance will be further enhanced in the future.

As a consequence of the mis-regulation of one or more of these receptors, it is widely believed that many tumours become clinically more aggressive and so correlate with a poorer prognosis for the patient (Brabender et al, *Clin. Cancer Res.,* 2001, 7, 1850; Ross et al, *Cancer Investigation,* 2001, 19, 554, Yu et al., *Bioessays,* 2000, 22.7, 673). In addition to these clinical findings, a wealth of pre-clinical information suggests that the erbB family of receptor tyrosine kinases are involved in cellular transformation. This includes the observations that many tumour cell lines overexpress one or more of the erbB receptors and that EGFR or erbB2 when transfected into non-tumour cells have the ability to transform these cells. This tumourigenic potential has been further verified as transgenic mice that overexpress erbB2 spontaneously develop tumours in the mammary gland. In addition to this, a number of pre-clinical studies have demonstrated that antiproliferative effects can be induced by knocking out one or more erbB activities by small molecule inhibitors, dominant negatives or inhibitory antibodies (reviewed in Mendelsohn et al., *Oncogene*, 2000, 19, 6550). Thus it has been recognised that inhibitors of these receptor tyrosine kinases should be of value as a selective inhibitor of the proliferation of mammalian cancer cells (Yaish et al. *Science*, 1988, 242, 933, Kolibaba et al, Biochimica et Biophysica Acta, 1997, 133, F217-F248; Al-Obeidi et al, 2000, *Oncogene*, 19, 5690-5701; Mendelsohn et al, 2000, *Oncogene*, 19, 6550-6565).

Recently the small molecule EGFR tyrosine kinase inhibitor, Iressa (also known as gefitinib, and ZD1834) has been approved for use in the treatment of advanced non-small cell lung cancer. Furthermore, findings using inhibitory antibodies against EGFR and erbB2 (c-225 and trastuzumab respectively) have proven to be beneficial in the clinic for the treatment of selected solid tumours (reviewed in Mendelsohn et al, 2000, *Oncogene*, 19, 6550-6565).

Amplification and/or activity of members of the erbB receptor tyrosine kinases have been detected and so have been implicated to play a role in a number of non-malignant proliferative disorders such as psoriasis (Ben-Bassat, *Curr. Pharm. Des.*, 2000, 6, 933; Elder et al., Science, 1989, 243, 811), benign prostatic hyperplasia (BPH) (Kumar et al., *Int. Urol. Nephrol.*, 2000, 32,73), atherosclerosis and restenosis (Bokemeyer et al., *Kidney Int.*, 2000, 58, 549). It is therefore expected that inhibitors of erbB receptor tyrosine kinases will be useful in the treatment of these and other non-malignant disorders of excessive cellular proliferation.

European patent application EP 566 226 discloses certain 4-anilinoquinazolines that are receptor tyrosine kinase inhibitors.

International patent applications WO 96/33977, WO 96/33978, WO 96/33979, WO 96/33980, WO 96/33981, WO 97/30034, WO 97/38994 disclose that certain quinazoline derivatives which bear an anilino substituent at the 4-position and a substituent at the 6- and/or 7-position possess receptor tyrosine kinase inhibitory activity.

European patent application EP 837 063 discloses aryl substituted 4-aminoquinazoline derivatives carrying moiety containing an aryl or heteroaryl group at the 6-or 7-position on the quinazoline ring. The compounds are stated to be useful for treating hyperproliferative disorders.

International patent applications WO 97/30035 and WO 98/13354 disclose certain 4-anilinoquinazolines substituted at the 7-position are vascular endothelial growth factor receptor tyrosine kinase inhibitors.

WO 00/55141 discloses 6,7-substituted 4-anilinoquinazoline compounds characterised in that the substituents at the 6-and/or 7-position carry certain ester groups.

WO 00/56720 discloses 6,7-dialkoxy-4-anilinoquinazoline compounds for the treatment of cancer or allergic reactions.

WO01/21596 discloses the use of certain 4-anilinoquinazoline derivatives as aurora 2 kinase inhibitors.

WO 02/18351 and WO 02/18372 disclose certain 4-anilinoquinazoline compounds substituted at the 6- and/or 7-position which are stated to have an inhibitory effect upon signal transduction mediated by tyrosine kinases.

WO 02/41882 discloses 4-anilinoquinazoline compounds substituted at the 6- and/or 7-position by a substituted pyrrolidinyl-alkoxy or piperidinyl-alkoxy group.

We have now found that surprisingly certain quinazoline derivatives substituted at the 7-position with a substituent containing certain substituted alkanoyl groups possess potent anti-tumour activity. The compounds of the present invention also generally possess high cellular potency, and favourable physical properties, particularly solubility, which may provide advantages in the formulation and delivery of the compound to patients. Many of the compounds of the invention posses favourable DMPK properties, for example high bioavailability and/or high free-plasma levels and/or advantageous half life and/or advantageous volume of distribution and such properties are expected to provide improved in-vivo efficacy and may reduce inter-patient variability in exposure to the compound compared to other EGFR tyrosine kinase inhibitors such as gefitinib.

Furthermore, many of the compounds according to the present invention are inactive or only weakly active in a hERG assay.

Without wishing to imply that the compounds disclosed in the present invention possess pharmacological activity only by virtue of an effect on a single biological process, it is believed that the compounds provide an anti-tumour effect by way of inhibition of one or more of the erbB family of receptor tyrosine kinases that are involved in the signal transduction steps which lead to the proliferation of tumour cells. In particular, it is believed that the compounds of the present invention provide an anti-tumour effect by way of inhibition of EGFR tyrosine kinase.

Generally the compounds of the present invention possess potent inhibitory activity against the erbB receptor tyrosine kinase family, for example by inhibition of EGF and/or erbB2 and/or erbB4 receptor tyrosine kinases, whilst possessing less potent inhibitory activity against other kinases, such as VEGF and KDR receptor tyrosine kinases. Furthermore, the compounds of the present invention possess substantially better potency against the EGFR tyrosine kinase over that of the erbB2 tyrosine kinase. Accordingly, it may be possible to administer a compound according to the present invention at a dose that is sufficient to inhibit EGFR tyrosine kinase whilst having no significant effect upon erbB2 (or other) tyrosine kinases. The selective inhibition provided by the compounds according to the present invention may provide treatments for conditions mediated by EGFR tyrosine kinase, whilst reducing undesirable side effects that may be associated with the inhibition of other tyrosine kinases.

According to a first aspect of the invention there is provided a quinazoline derivative of the Formula I:

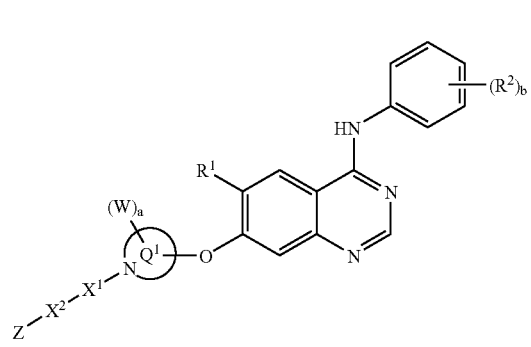

I wherein:

$R^1$ is selected from hydrogen, hydroxy, (1-6C)alkoxy, (2-6C)alkenyloxy, (2-6C)alkynyloxy, or from a group of the formula:

$Q^2$-$X^3$— wherein $X^3$ is a direct bond or is O, and $Q^2$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein adjacent carbon atoms in any (2-6C)alkylene chain within a $R^1$ substituent are optionally separated by the insertion into the chain of a group selected from O, S, SO, $SO_2$, $N(R^3)$, CO, $CH(OR^3)$, $CON(R^3)$, $N(R^3)CO$, $SO_2N(R^3)$, $N(R^3)SO_2$, CH=CH and C≡C wherein $R^3$ is hydrogen or (1-6C)alkyl, and wherein any $CH_2$=CH— or HC≡C— group within a $R^1$ substituent optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^3-X^4—$$

wherein $X^3$ is a direct bond or is selected from CO and $N(R^4)CO$, wherein $R^4$ is hydrogen or (1-6C)alkyl, and $Q^4$ is heterocyclyl or heterocyclyl-(1-6C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, oxo, thioxo, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$$—X^5-Q^4$$

wherein $X^5$ is a direct bond or is selected from O, S, SO, $SO_2$, $N(R^5)$, CO, $CH(OR^5)$, $CON(R^5)$, $N(R^5)CO$, $SO_2N(R^5)$, $N(R^5)SO_2$, $C(R^5)_2O$, $C(R^5)_2S$ and $C(R^5)_2N(R^5)$, wherein $R^5$ is hydrogen or (1-6C)alkyl, and $Q^4$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein any heterocyclyl group within a substituent on $R^1$ optionally bears one or more (for example 1, 2 or 3) substituents, which may be the same or different, selected from halogeno, trifluoromethyl, cyano, nitro, hydroxy, amino, carboxy, carbamoyl, formyl, mercapto, sulfamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, N-(1-6C)alkylsulfamoyl, N,N-di-[(1-6C)alkyl]sulfamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, and N-(1-6C)alkyl-(1-6C)alkanesulfonylamino, or from a group of the formula:

$$—X^6—R^6$$

wherein $X^6$ is a direct bond or is selected from O, $N(R^7)$ and C(O), wherein $R^7$ is hydrogen or (1-6C)alkyl, and $R^6$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, and wherein any heterocyclyl group within a substituent on $R^1$ optionally bears 1 or 2 oxo or thioxo substituents;

b is 1, 2, 3, 4 or 5;

each $R^2$, which may be the same or different, is selected from halogeno, cyano, nitro, hydroxy, amino, carboxy, carbamoyl, sulfamoyl, trifluoromethyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino and a group of the formula:

$$—X^7—R^8$$

wherein $X^7$ is a direct bond or is selected from O and $N(R^9)$, wherein $R^9$ is hydrogen or (1-6C)alkyl, and $R^8$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl;

$Q^1$ is piperidinyl;

a is 0, 1, 2, 3 or 4;

each W, which may be the same or different, is selected from halogeno, trifluoromethyl, cyano, nitro, hydroxy, oxo, amino, formyl, mercapto, (1-6C)alkyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$—X^8—R^{10}$$

wherein $X^8$ is a direct bond or is selected from O, CO, $SO_2$ and $N(R^{11})$, wherein $R^{11}$ is hydrogen or (1-6C)alkyl, and $R^{10}$ is halogeno-(1-6C)alkyl, hydroxy-(1-6C)alkyl, (1-6C)alkoxy-(1-6C)alkyl, cyano-(1-6C)alkyl, amino-(1-6C)alkyl, N-(1-6C)alkylamino-(1-6C)alkyl or N,N-di-[(1-6C)alkyl]amino-(1-6C)alkyl;

$X^1$ is selected from CO and $SO_2$;

$X^2$ is a group of the formula:

$$—(CR^{12}R^{13})_p-(Q^5)_m-(CR^{14}R^{15})_q—$$

wherein m is 0 or 1, p is 0, 1, 2, 3 or 4 and q is 0, 1, 2, 3 or 4, each of $R^{12}$, $R^{13}$, $R^{14}$ and $R^{15}$, which may be the same or different, is selected from hydrogen, (1-6C)alkyl, amino, (1-6C)alkylamino and di-[(1-6C)alkyl]amino, and $Q^5$ is selected from (3-7C)cycloalkylene and (3-7C)cycloalkenylene, and wherein any $CH_2$ or $CH_3$ group within an $X^2$ group, optionally bears on each said $CH_2$ or $CH_3$ group one or more halogeno or (1-6C)alkyl substituents or a substituent selected from hydroxy, cyano, amino, (1-6C)alkoxy, (1-6C)alkylamino and di-[(1-6C)alkyl]amino;

Z is selected from hydroxy, amino, (1-6C)alkylamino, di-[(1-6C)alkyl]amino, (1-6C)alkoxy, (1-6C)alkylsulfonyl, (1-6C)alkanesulfonylamino, N-(1-6C)alkyl-(1-6C)alkanesulfonylamino and a group of the formula:

$Q^6$-$X^9$— wherein $X^9$ is a direct bond or is selected from O, N($R^{16}$), $SO_2$ and $SO_2$N($R^{16}$), wherein $R^{16}$ is hydrogen or (1-6C)alkyl, and $Q^6$ is (3-7C)cycloalkyl, (3-7C)cycloalkyl-(1-4C)alkyl, (3-7C)cycloalkenyl, (3-7C)cycloalkenyl-(1-4C)alkyl, heterocyclyl or heterocyclyl-(1-4C)alkyl;

provided that when $X^9$ is a direct bond, $Q^6$ is heterocyclyl, and provided that when m, p and q are all 0, then Z is heterocyclyl, and wherein adjacent carbon atoms in any (2-6C)alkylene chain within a Z substituent are optionally separated by the insertion into the chain of a group selected from O, S, SO, $SO_2$, N($R^{17}$), CO, —C≡C— and —C≡C— wherein $R^{17}$ is hydrogen or (1-6C)alkyl, and wherein and wherein any $CH_2$ or $CH_3$ group within any Z group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein any heterocyclyl group within a Z substituent optionally bears one or more (for example 1, 2 or 3) substitutents which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^{10}$—$R^{18}$ wherein $X^{10}$ is a direct bond or is selected from O, CO, $SO_2$ and N($R^{19}$), wherein $R^{19}$ is hydrogen or (1-4C)alkyl, and $R^{18}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl; provided that:

when the 4-anilino group in Formula I is 4-bromo-2-fluoroanilino or 4-chloro-2-fluoroanilino and $R^1$ is hydrogen or (1-3C)alkoxy, then a is 0 and Z is selected from hydroxy, amino, (1-6C)alkylamino, di-[(1-6C)alkyl]amino, (1-6C)alkoxy, (1-6C)alkylsulfonyl, (1-6C)alkanesulfonylamino, N-(1-6C)alkyl-(1-6C)alkanesulfonylamino, and a group of the formula $Q^6$-$X^9$—;

or a pharmaceutically acceptable salt, or a pharmaceutically acceptable ester thereof.

In a particular embodiment of the invention there is provided a quinazoline derivative of the Formula I as defined above, or a pharmaceutically acceptable salt thereof.

In this specification the generic term "alkyl" includes both straight-chain and branched-chain alkyl groups such as propyl, isopropyl and tert-butyl, and (3-7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes methoxy, ethoxy, cyclopropyloxy and cyclopentyloxy, (1-6C)alkylamino includes methylamino, ethylamino, cyclobutylamino and cyclohexylamino, and di-[(1-6Calkyl]amino includes dimethylamino, diethylamino, N-cyclobutyl-N-methylamino and N-cyclohexyl-N-ethylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. It is further to be understood that in the names of chiral compounds (R,S) denotes any scalemic or racemic mixture while (R) and (S) denote the enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ratio 50:50. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the 'Q' groups (for example $Q^2$, $Q^4$ or $Q^6$) when it is (3-7C)cycloalkyl or for the (3-7C) cycloalkyl group within a 'Q' or R group is, for example, cyclopropyl, cyclobutyl, cyclopentyl, cyclohexyl, cycloheptyl or bicyclo[2.2.1]heptyl and a suitable value for any one of the 'Q' groups (for example $Q^2$, $Q^4$ or $Q^6$) when it is (3-7C) cycloalkenyl or for the (3-7C)cycloalkenyl group within a 'Q' group is, for example, cyclobutenyl, cyclopentenyl, cyclohexenyl or cycloheptenyl. It is to be understood that reference to (3-7C)cycloalkylene used herein for $Q^5$ refers to a divalent (3-7C)cycloalkane linking group, which group may be linked via different carbon atoms in the (3-7C)cycloalkylene ring, or which may be linked via a single carbon atom in the (3-7C) cycloalkylene ring. Accordingly, reference to, for example, a "cyclopropylene" group includes cycloprop-1,2-ylene and a cyclopropylidene group of the formula:

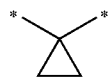

However references to an individual (3-7C)cycloalklene group such as cyclopropylidene are specific for that group only. A silmilar convention is adopted for the (3-7C)cycloalkenylene groups represented by $Q^5$.

A suitable value for the 'Q' groups, other than $Q^1$ (for example $Q^2$, $Q^3$, $Q^4$ or $Q^6$) when it is heterocyclyl or for the heterocyclyl group within a 'Q' group is a non-aromatic saturated (i.e. ring systems with the maximum degree of saturation) or partially saturated (i.e. ring systems retaining some, but not the full, degree of unsaturation) 3 to 10 membered monocyclic or bicyclic ring with up to five heteroatoms selected from oxygen, nitrogen and sulfur, which, unless specified otherwise, may be carbon or nitrogen linked, for example oxiranyl, oxetanyl, azetidinyl, tetrahydrofuranyl, 1,3-dioxolanyl, tetrahydropyranyl, 1,4-dioxanyl, oxepanyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl, decahydroisoquinolinyl or decahydroquinolinyl, particularly tetrahydrofuranyl, tetrahydropyranyl, pyrrolidinyl, morpholinyl, 1,4-oxazepanyl, thiamorpholinyl 1,1-dioxotetrahydro-4H-1,4-thiazinyl, piperidinyl or piperazinyl, more particularly tetrahydrofuran-3-yl, tetrahydropyran-4-yl, tetrahydrothien-3-yl, tetrahydrothiopyran-4-yl, pyrrolidin-1-yl, pyrrolidin-2-yl, pyrrolidin-3-yl, morpholino, morpholin-2-yl, piperidino, piperidin-4-yl, piperidin-3-yl, piperidin-2-yl or piperazin-1-yl. A nitrogen or sulfur atom within a heterocyclyl group may be oxidized to give the corresponding N or S oxide, for example 1,1-dioxotetrahydrothienyl, 1-oxotetrahydrothienyl, 1,1-dioxotetrahydrothiopyranyl or 1-oxotetrahydrothiopyranyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

$Q^1$ is piperidinyl, which group is linked to the oxygen in Formula I by a ring carbon atom.

A suitable value for a 'Q' group when it is heterocyclyl-(1-6C)alkyl is, for example, heterocyclylmethyl, 2-heterocyclylethyl and 3-heterocyclylpropyl. The invention comprises corresponding suitable values for 'Q' groups when, for example, rather than a heterocyclyl-(1-6C)alkyl group, an (3-7C)cycloalkyl-(1-6C)alkyl or (3-7C)cycloalkenyl-(1-6C)alkyl is present.

Suitable values for any of the 'R' groups ($R^1$ to $R^{19}$), W, or for various groups within a $X^1$, $X^2$ or Z group include:
for halogeno fluoro, chloro, bromo and iodo;
for (1-6C)alkyl: methyl, ethyl, propyl, isopropyl and tert-butyl;
for (2-8C)alkenyl: vinyl, isopropenyl, allyl and but-2-enyl;
for (2-8C)alkynyl: ethynyl, 2-propynyl and but-2-ynyl;
for (1-6C)alkoxy: methoxy, ethoxy, propoxy, isopropoxy and butoxy;
for (2-6C)alkenyloxy: vinyloxy and allyloxy;
for (2-6C)alkynyloxy: ethynyloxy and 2-propynyloxy;
for (1-6C)alkylthio: methylthio, ethylthio and propylthio;
for (1-6C)alkylsulfinyl: methylsulfinyl and ethylsulfinyl;
for (1-6C)alkylsulfonyl: methylsulfonyl and ethylsulfonyl;
for (1-6C)alkylamino: methylamino, ethylamino, propylamino, isopropylamino and butylamino;
for di-[(1-6C)alkyl]amino: dimethylamino, diethylamino, N-ethyl-N-methylamino and diisopropylamino;
for (1-6C)alkoxycarbonyl: methoxycarbonyl, ethoxycarbonyl, propoxycarbonyl and tert-butoxycarbonyl;
for N-(1-6C)alkylcarbamoyl: N-methylcarbamoyl, N-ethylcarbamoyl and N-propylcarbamoyl;
for N,N-di-[(1-6C)alkyl]carbamoyl: N,N-dimethylcarbamoyl, N-ethyl-N-methylcarbamoyl and N,N-diethylcarbamoyl;
for (2-6C)alkanoyl: acetyl, propionyl, butyryl and isobuyryl;
for (2-6C)alkanoyloxy: acetoxy and propionyloxy;
for (2-6C)alkanoylamino: acetamido and propionamido;
for N-(1-6C)alkyl-(2-6C)alkanoylamino: N-methylacetamido and N-methylpropionamido;
for N-(1-6C)alkylsulfamoyl: N-methylsulfamoyl and N-ethylsulfamoyl;
for N,N-di-[(1-6C)alkyl]sulfamoyl: N,N-dimethylsulfamoyl;
for (1-6C)alkanesulfonylamino: methanesulfonylamino and ethanesulfonylamino;
for N-(1-6C)alkyl-(1-6C)alkanesulfonylamino: N-methylmethanesulfonylamino and N-methylethanesulfonylamino;
for (3-6C)alkenoylamino: acrylamido, methacrylamido and crotonamido;
for N-(1-6C)alkyl-(3-6C)alkenoylamino: N-methylacrylamido and N-methylcrotonamido;
for (3-6C)alkynoylamino: propiolamido;
for N-(1-6C)alkyl-(3-6C)alkynoylamino: N-methylpropiolamido;
for amino-(1-6C)alkyl: aminomethyl, 2-aminoethyl, 1-aminoethyl and 3-aminopropyl;
for (1-6C)alkylamino-(1-6C)alkyl: methylaminomethyl, ethylaminomethyl, 1-methylaminoethyl, 2-methylaminoethyl, 2-ethylaminoethyl and 3-methylaminopropyl;
for di-[(1-6C)alkyl]amino-(1-6C)alkyl: dimethylaminomethyl, diethylaminomethyl, 1-dimethylaminoethyl, 2-dimethylaminoethyl and 3-dimethylaminopropyl;
for halogeno-(1-6C)alkyl: chloromethyl, 2-chloroethyl, 1-chloroethyl and 3-chloropropyl;
for hydroxy-(1-6C)alkyl: hydroxymethyl, 2-hydroxyethyl, 1-hydroxyethyl and 3-hydroxypropyl;
for (1-6C)alkoxy-(1-6C)alkyl: methoxymethyl, ethoxymethyl, 1-methoxyethyl, 2-methoxyethyl, 2-ethoxyethyl and 3-methoxypropyl;
for cyano-(1-6C)alkyl: cyanomethyl, 2-cyanoethyl, 1-cyanoethyl and 3-cyanopropyl;
for (1-6C)alkylthio-(1-6C)alkyl: methylthiomethyl, ethylthiomethyl, 2-methylthioethyl, 1-methylthioethyl and 3-methylthiopropyl;
for (1-6C)alkylsulfinyl-(1-6C)alkyl: methylsulfinylmethyl, ethylsulfinylmethyl, 2-methylsulfinylethyl, 1-methylsulfinylethyl and 3-methylsulfinylpropyl;
for (1-6C)alkylsulfonyl-(1-6C)alkyl: methylsulfonylmethyl, ethylsulfonylmethyl, 2-methylsulfonylethyl, 1-methylsulfonylethyl and 3-methylsulfonylpropyl;
for (2-6C)alkanoylamino-(1-6C)alkyl: acetamidomethyl, propionamidomethyl and 2-acetamidoethyl;
for N-(1-6C)alkyl-(2-6C)alkanoylamino-(1-6C)alkyl: N-methylacetamidomethyl, 2-(N-methylacetamido)ethyl and 2-(N-methylpropionamido)ethyl;
for (1-6C)alkoxycarbonylamino-(1-6C)alkyl: methoxycarbonylaminomethyl, ethoxycarbonylaminomethyl, tert-butoxycarbonylaminomethyl and 2-methoxycarbonylaminoethyl;
(2-6C)alkanoyloxy-(1-6C)alkyl: acetoxymethyl, 2-acetoxyethyl and 2-propionyloxyethyl;
for carbamoyl-(1-6C)alkyl: carbamoylmethyl, 1-carbamoylethyl, 2-carbamoylethyl and 3-carbamoylpropyl;
for (2-6C)alkanoyl-(1-6C)alkyl: acetylmethyl and 2-acetylethyl;
for N-(1-6C)alkylcarbamoyl-(1-6C)alkyl: N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;
for N,N-di[(1-6C)alkyl]carbamoyl-(1-6C)alkyl: N,N-dimethylcarbamoylmethyl, N,N-diethylcarbamoylmethyl, 2-(N,N-dimethylcarbamoyl)ethyl, and 3-(N,N-dimethylcarbamoyl)propyl;
for sulfamoyl(1-6C)alkyl: sulfamoylmethyl, 1-sulfamoylethyl, 2-sulfamoylethyl and 3-sulfamoylpropyl;

for N-(1-6C)alkylsulfamoyl(1-6C)alkyl: N-methylsulfamoylmethyl, N-ethylsulfamoylmethyl, N-propylsulfamoylmethyl, 1-(N-methylsulfamoyl)ethyl, 2-(N-methylsulfamoyl)ethyl and 3-(N-methylsulfamoyl)propyl; and for N,N di-(1-6C)alkylsulfamoyl(1-6C)alkyl: N,N-dimethylsulfamoylmethyl, N,N-diethylsulfamoylmethyl, N methyl, N-ethylsulfamoylmethyl, 1-(N,N-dimethylsulfamoyl) ethyl, 1-(N,N-diethylsulfamoyl)ethyl, 2-(N,N-dimethylsulfamoyl)ethyl, 2-(N,N-diethylsulfamoyl)ethyl and 3-(N, N-dimethylsulfamoyl)propyl.

When, as defined hereinbefore Z in Formula I is a group of the formula $Q^6$-$X^9$—, and $X^9$ is $SO_2N(R^{16})$, the $SO_2$ group is attached to $Q^6$ and the nitrogen atom is attached to $X^2$ in Formula I. The same convention is applied to other groups defined herein. For example when $X^2$ is a group of the formula $Q^5$-$(CR^{14}R^{15})_p$, the $Q^5$ group is attached to the group Z in Formula I and the $(CR^{14}R^{15})_p$ group is attached to the $X^1$ group in Formula I.

As defined hereinbefore, adjacent carbon atoms in any (2-6C)alkylene chain within, for example, a $R^1$ substituent may be optionally separated by the insertion into the chain of a group such as O, $CON(R^3)$, $N(R^3)$ or C≡C. For example, insertion of a C≡C group into the ethylene chain within a 2-morpholinoethoxy group gives rise to a 4morpholinobut-2-ynyloxy group and, for example, insertion of a CONH group into the ethylene chain within a 3-methoxypropoxy group gives rise to, for example, a 2-(2-methoxyacetamido)ethoxy group. It is to be understood that the term (2-6C)alkylene chain refers to any $CH_2CH_2$ group (for example within $R^1$) and includes, for example alkylene chains within a (1-6C) alkyl, (1-6C)alkoxy, (2-8C)alkenyl, (2-8C)alkenyloxy, (2-8C)alkynyl and (2-8C)alkynyloxy group. For example the insertion of a $N(CH_3)$ group between the third and fourth carbon atoms in a hex-5-enyloxy group in $R^1$ gives rise to a 3-(N-methyl-N-allylamino)propoxy group.

When, as defined hereinbefore, any $CH_2$=CH— or HC≡C— group within a $R^1$ substituent optionally bears at the terminal $CH_2$=or HC≡ position a substituent such as a group of the formula $Q^3$-$X^4$— wherein $X^4$ is, for example, NHCO and $Q^3$ is a heterocyclyl-(1-6C)alkyl group, suitable $R^1$ substituents so formed include, for example, N-[heterocyclyl-(1-6C)alkyl]carbamoylvinyl groups such as N-(2-pyrrolidin-1-ylethyl)carbamoylvinyl or N-[heterocyclyl-(1-6C) alkyl]carbamoylethynyl groups such as N-(2-pyrrolidin-1-ylethyl)carbamoylethynyl.

When reference is made herein to a $CH_2$ or $CH_3$ group optionally bearing on each said $CH_2$ or $CH_3$ group one or more halogeno or (1-6C)alkyl substituents, there are suitably 1 or 2 halogeno or (1-6C)alkyl substituents present on each said $CH_2$ group and there are suitably 1, 2 or 3 such substituents present on each said $CH_3$ group.

Where reference is made herein to any $CH_2$ or $CH_3$ group optionally bearing on each said $CH_2$ or $CH_3$ group a substituent as defined herein, suitable substituents so formed include, for example, hydroxy-substituted heterocyclyl-(1-6C)alkoxy groups such as 2-hydroxy-3-piperidinopropoxy and 2-hydroxy-3-morpholinopropoxy, hydroxy-substituted heterocyclyl-(1-6C)alkylamino groups such as 2-hydroxy-3-piperidinopropylamino and 2-hydroxy-3-morpholinopropylamino, and hydroxy-substituted (2-6)alkanoyl groups such as hydroxyacetyl, 2-hydroxypropionyl and 2-hydroxybutyryl.

Where reference is made herein to "any $CH_2$ or $CH_3$ group, other than a $CH_2$ group within a heterocyclyl group, optionally bearing a substituent", it is to be understood that such a statement is present only to distinguish between optional substituents that may be present on, for example, a $CH_3$ group in an alkyl group from substituents that may be present on carbon atoms of a heterocyclyl group. Accordingly, it is to be understood, that this statement does not exclude other substituents being present on ring carbon atoms in a heterocyclyl group when it is stated herein that said heterocyclyl group may also optionally bear one or more substituents. For example, if $R^1$ is 3-(pyrrolidin-1-yl)propoxy and herein it is stated that a $CH_2$ or $CH_3$ group within, for example, a $R^1$ substituent, other than a $CH_2$ group within a heterocyclyl group, optionally bears a hydroxy substituent, and that any heterocyclyl group within $R^1$ optionally bears an alkyl substituent, then the optional hydroxy substituent may be present on a $CH_2$ of the propoxy group to give for example a 2-hydroxy-3-(pyrrolidin-1-yl)propoxy group. Similarly an alkyl group such as methyl may be present on the pyrrolidinyl ring to give, for example, a 3-(3-methylpyrrolidin-1-yl)propoxy group. Equally, the propoxy group may be substituted by a hydroxy group and the pyrrolidinyl ring may be substituted by a methyl group to give, for example, a 2-hydroxy-3-(3-methylpyrrolidin-1-yl)propoxy group.

For the avoidance of doubt, when W is oxo, a $CH_2$ in $Q^1$ is substituted by O to give a C(O) group.

It is to be understood that reference herein to $Q^1$ being, for example piperidin-4-yl refers to the attachment of the piperidine ring to the oxygen in Formula I. The piperidine ring is further substituted at the 1-position by the group Z-$X^2$—$X^1$— and optionally bears one or more W substituents on one or more of the available piperidinyl ring carbon atoms.

It is to be understood that certain compounds of the Formula I may exist in solvated as well as unsolvated forms such as, for example, hydrated forms. It is to be understood that the invention encompasses all such solvated forms which exhibit an inhibitory effect on an erbB receptor tyrosine kinase.

It is also to be understood that certain compounds of the Formula I may exhibit polymorphism, and that the invention encompasses all such forms which exhibit an inhibitory effect on an erbB receptor tyrosine kinase.

It is also to be understood that the invention relates to all tautomeric forms of the compounds of the Formula I forms which exhibit an inhibitory effect on an erbB receptor tyrosine kinase.

A suitable pharmaceutically acceptable salt of a compound of the Formula I is, for example, an acid-addition salt of a compound of the Formula I, for example an acid-addition salt with an inorganic or organic acid such as hydrochloric, hydrobromic, sulfuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

The term "pharmaceutically acceptable ester" used herein refers to an ester of a quinazoline derivative of the Formula I which hydrolyses in vivo to leave the parent compound or a pharmaceutically acceptable salt thereof. An in-vivo hydrolysable ester of a quinazoline of Formula I may be used to alter or improve the physical and/or pharmacokinetic profile of the parent compound, for example the solubility. Suitable ester groups that may be used in the formation of pharmaceutically acceptable ester prodrugs are well known, for example as discussed in for example:

Pro-drugs as Novel Delivery Systems, T. Higuchi and V. Stella, Vol. 14 of the ACS Symposium Series, and in Edward B. Roche, ed.;

Bioreversible Carriers in Drug Design, American Pharmaceutical Association and Pergamon Press, 1987;

Design of Prodrugs, edited by H. Bundgaard, (Elsevier, 1985) and Methods in Enzymology, Vol. 42, p. 309-396, edited by K. Widder, et al. (Academic Press, 1985);

A Textbook of Drug Design and Development, edited by Krogsgaard-Larsen and H. Bundgaard, Chapter 5 "Design and Application of Prodrugs", by H. Bundgaard p. 113-191 (1991);

H. Bundgaard, Advanced Drug Delivery Reviews, 8, 1-38 (1992);

H. Bundgaard, et al., Journal of Pharmaceutical Sciences, 77, 285 (1988); and

N. Kakeya, et al., Chem Pharm Bull, 32, 692 (1984).

A particular pharmaceutically acceptable ester of a quinazoline derivative of the Formula I or a pharmaceutically acceptable salt thereof is, an ester formed with a carboxy or, particularly, a hydroxy group (for example when Z is hydroxy) in Formula I, which ester is hydrolysed in the human or animal body to produce the parent quinazoline of Formula I when administered to a warm blooded animal such as a human.

Suitable pharmaceutically acceptable esters for a carboxy group in Formula I include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically acceptable esters for a hydroxy group in Formula I or a pharmaceutically acceptable salt thereof include inorganic esters such as phosphate esters, α-acyloxyalkyl ethers and related compounds, and esters derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms, and may be formed at any hydroxy group in the compounds of this invention, for example when Z is hydroxy or contains a hydroxy group. Following administration, the pharmaceutically acceptable ester undergoes in-vivo hydrolysis breakdown to give the parent carboxy/hydroxy group in the quinazoline derivative of Formula I.

Examples of α-acyloxyalkyl ethers that may be used to form a pharmaceutically acceptable ester include acetoxymethoxy and 2,2-dimethylpropionyloxymethoxy. A selection of pharmaceutically acceptable ester forming groups for a hydroxy group in Formula I (for example when Z is hydroxy) include (1-6C)alkanoyl, benzoyl, phenylacetyl and substituted benzoyl and phenylacetyl, (1-6C)alkoxycarbonyl (to give alkyl carbonate esters), di-(1-4C)alkylcarbamoyl and N-(di-(1-4C)alkylaminoethyl)-N-(1-4C)alkylcarbamoyl (to give carbamates), di-(1-4C)alkylaminoacetyl and carboxyacetyl. Examples of substituents on benzoyl include chloromethyl or aminomethyl, (1-4C)alkylaminomethyl and di-((1-4C)alkyl)aminomethyl, and morpholino or piperazino linked from a ring nitrogen atom via a methylene linking group to the 3- or 4-position of the benzoyl ring.

Particular pharmaceutically acceptable esters are phosphate esters formed with a hydroxy group in the quinazoline derivative for the Formula I (for example when Z is hydroxy or contains a hydroxy group), or a pharmaceutically acceptable salt thereof. More particularly, pharmaceutically acceptable esters include quinazoline derivatives of the Formula I in which a hydroxy group in Formula I forms a phosphoryl (npd is 1) or phosphiryl (npd is 0) ester of the formula (PD1), or a pharmaceutically acceptable salt thereof:

(PD1)

Another particular pharmaceutically acceptable ester is a quinazoline derivative of the Formula I in which a hydroxy in Formula I (for example when Z is hydroxy) forms a phosphoryl to give a group of the formula (PD1) wherein npd is 1.

Useful intermediates for the preparation of such esters include compounds containing a group of formula (PD1) in which either or both of the —OH groups in (PD1) is independently protected by (1-4C)alkyl (such compounds also being interesting compounds in their own right), phenyl or phenyl-(1-4C)alkyl (such phenyl groups being optionally substituted by 1 or 2 groups independently selected from (1-4C)alkyl, nitro, halo and (1-4C)alkoxy).

Pharmaceutically acceptable esters of a quinazoline derivative of Formula I containing a group such as (PD1), may be prepared by reaction of a quinazoline derivative Formula I with a suitably protected phosphorylating agent (for example, containing a chloro or dialkylamino leaving group), followed by oxidation (if necessary) and deprotection. Suitable phosphorylating agents are well known and include, for example protected phosphoramidite compounds such as a N,N-di-[(1-6C)alkyl]-phosphoramidite, for example di-tert-butyl N,N-diethylphosphoramidite.

It is to be understood that an ester group in the quinazoline derivative of the Formula I may form a pharmaceutically acceptable salt of the ester group and that such salts form part of the present invention. Where pharmaceutically acceptable salts of a pharmaceutically acceptable ester is required this is achieved by conventional techniques well known to those of ordinary skill in the art. Thus, for example, compounds containing a group of formula (PD1), may ionise (partially or fully) to form salts with an appropriate number of counterions. By way of example, if a pharmaceutically acceptable ester pro-drug of a quinazoline derivative Formula I contains a (PD1) group, there are two HO—P— functionalities present, each of which may form an appropriate salt with a suitable counter-ion. Suitable salts of a group of the formula (PD1) are base salts such as an alkali metal salt for example sodium, an alkaline earth metal salt for example calcium or magnesium or an organic amine salt for example triethylamine, or tris-(2-hydroxyethyl)amine. Thus for example the group (PD1) may form, a mono- or di-sodium salt).

Particular novel compounds of the invention include, for example, quinazoline derivatives of the Formula I, or pharmaceutically acceptable salts, or pharmaceutically acceptable esters thereof, wherein, unless otherwise stated, each of $R^1$, $R^2$, W, $Q^1$, $X^1$, $X^2$, a, b and Z has any of the meanings defined hereinbefore or in paragraphs (a) to (nnnn) hereinafter:

(a) $R^1$ is selected from hydrogen, hydroxy, (1-6C)alkoxy, (2-6C)alkenyloxy, (2-6C)alkynyloxy, or from a group of the formula:

$Q^2$-$X^3$— wherein $X^3$ is a direct bond or is O, and $Q^2$ is (3-7C)cycloalkyl, (3-7C)cycloalkyl-(1-6C)alkyl, heterocyclyl or heterocyclyl-(1-6C)alkyl, and wherein adjacent carbon atoms in any (2-6C)alkylene chain within a $R^1$ substituent are optionally separated by the insertion into the chain of a group selected from O, $N(R^3)$, $CON(R^3)$, $N(R^3)CO$, CH=CH and C≡C wherein $R^3$ is hydrogen or (1-6C)alkyl, and wherein any $CH_2$=CH— or HC≡C— group within a $R^1$ substituent optionally bears at the terminal $CH_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$Q^3$-$X^4$— wherein $X^4$ is a direct bond or is selected from CO and $N(R^4)CO$, wherein $R^4$ is hydrogen or (1-6C)alkyl, and $Q^3$ is heterocyclyl or heterocyclyl-(1-6C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, amino, cyano, carbamoyl, (1-6C)alkoxy, (1-6C)alkylamino, di-[(1-6C)alkyl]amino, N-(1-6C)alkylcarbamoyl and N,N-di-[(1-6C)alkyl]carbamoyl, or from a group of the formula:

—$X^5$-$Q^4$ wherein $X^5$ is a direct bond or is selected from O, $N(R^5)$, $CON(R^5)$, $N(R^5)CO$ and $C(R^5)_2O$, wherein $R^5$ is hydrogen or (1-6C)alkyl, and $Q^4$ is heterocyclyl or heterocyclyl-(1-6C)alkyl, and wherein any heterocyclyl group within a substituent on $R^1$ optionally bears 1, 2 or 3 substituents, which may be the same or different, selected from halogeno, trifluoromethyl, cyano, nitro, hydroxy, amino, carbamoyl, (1-6C)alkyl, (2-8C)alkenyl, (2-8C)alkynyl, (1-6C)alkoxy, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, or from a group of the formula:

—$X^6$—$R^6$ wherein $X^6$ is a direct bond or is selected from O and $N(R^7)$, wherein $R^7$ is hydrogen or (1-6C)alkyl, and $R^6$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carbamoyl-(1-6C)alkyl, N-(1-6C)alkylcarbamoyl-(1-6C)alkyl and N,N-di-[(1-6C)alkyl]carbamoyl-(1-6C)alkyl, and wherein any heterocyclyl group within a substituent on $R^1$ optionally bears 1 or 2 oxo substituents;

(b) $R^1$ is selected from hydrogen, hydroxy, (1-6C)alkoxy, (2-6C)alkenyloxy, (2-6C)alkynyloxy, or from a group of the formula:

$Q^2$-$X^3$— wherein $X^3$ is a direct bond or is O, and $Q^2$ is heterocyclyl or heterocyclyl-(1-6C)alkyl, and wherein adjacent carbon atoms in any (2-6C)alkylene chain within a $R^1$ substituent are optionally separated by the insertion into the chain of a group selected from O, $N(R^3)$, $CON(R^3)$, $N(R^3)CO$, CH=CH and C≡C wherein $R^3$ is hydrogen or (1-6C)alkyl, and wherein any $CH_2$=CH— or HC≡C— group within a $R^1$ substituent optionally bears at the terminal $CH_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, amino, cyano, carbamoyl, (1-6C)alkoxy, (1-6C)alkylamino, di-[(1-6C)alkyl]amino, N-(1-6C)alkylcarbamoyl and N,N-di-[(1-6C)alkyl]carbamoyl, or from a group of the formula:

—$X^5$-$Q^4$ wherein $X^5$ is a direct bond or is selected from O, $N(R^5)$, $CON(R^5)$, $N(R^5)CO$ and $C(R^5)_2O$, wherein $R^5$ is hydrogen or (1-6C)alkyl, and $Q^4$ is heterocyclyl or heterocyclyl-(1-6C)alkyl, and wherein any heterocyclyl group within a substituent on $R^1$ optionally bears 1, 2 or 3 substituents, which may be the same or different, selected from halogeno, trifluoromethyl, hydroxy, amino, carbamoyl, (1-6C)alkyl, (2-8C)alkenyl, (2-8C)alkynyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, or from a group of the formula:

—$X^6$—$R^6$ wherein $X^6$ is a direct bond or is selected from O and $N(R^7)$, wherein $R^7$ is hydrogen or (1-6C)alkyl, and $R^6$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl and di-[(1-6C)alkyl]amino-(1-6C)alkyl, and wherein any heterocyclyl group within a substituent on $R^1$ optionally bears 1 or 2 oxo substituents;

(c) $R^1$ is selected from hydrogen, hydroxy, (1-6C)alkoxy, (2-6C)alkenyloxy and (2-6C)alkynyloxy, and wherein adjacent carbon atoms in any (2-6C)alkylene chain within a $R^1$ substituent are optionally separated by the insertion into the chain of a group selected from O, $N(R^3)$, $CON(R^3)$, $N(R^3)CO$, CH=CH and C≡C wherein $R^3$ is hydrogen or (1-6C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, amino, cyano, carbamoyl, (1-6C)alkoxy, (1-6C)alkylamino, di-[(1-6C)alkyl]amino, N-(1-6C)alkylcarbamoyl and N,N-di-[(1-6C)alkyl]carbamoyl;

(d) $R^1$ is selected from hydrogen, hydroxy, (1-6C)alkoxy, or from a group of the formula:

$Q^2$-$X^3$— wherein $X^3$ is O, and $Q^2$ is (3-7C)cycloalkyl, (3-7C)cycloalkyl-(1-6C)alkyl, heterocyclyl or heterocyclyl-(1-6C)alkyl, and wherein adjacent carbon atoms in any (2-6C)alkylene chain within a $R^1$ substituent are optionally separated by the insertion into the chain of a group selected from O and $N(R^3)$, wherein $R^3$ is hydrogen or (1-4C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, amino, cyano, (1-6C)alkoxy, (1-6C)alkylamino and di-[(1-6C)alkyl]amino, and wherein any heterocyclyl group within a substituent on $R^1$ optionally bears 1, 2 or 3 substituents, which may be the same or different, selected from halogeno, trifluoromethyl, cyano, nitro, hydroxy, amino, carbamoyl, (1-6C)alkyl, (2-8C)alkenyl, (2-8C)alkynyl, (1-6C)alkoxy, (1-6C)alkylsulfonyl, (1-6C)alkylamino, di-[(1-6C)alkyl]amino, N-(1-6C)alkylcarbamoyl, N,N-di-[(1-6C)alkyl]carbamoyl and (2-6C)alkanoyl, and wherein any heterocyclyl group within a substituent on $R^1$ optionally bears 1 or 2 oxo substituents;

(e) $R^1$ is selected from hydrogen, hydroxy, (1-6C)alkoxy, or from a group of the formula:

$$Q^2\text{-}X^3\text{---}$$

wherein $X^3$ is O, and $Q^2$ is azetidin-3-yl-(1-4C)alkyl, azetidin-1-yl-(2-4C)alkyl, pyrrolidin-2-yl-(1-4C)alkyl, pyrrolidin-3-yl-(1-4C)alkyl, pyrrolidin-1-yl-(2-4C)alkyl, piperidin-2-yl-(1-4C)alkyl, piperidin-3-yl-(1-4C)alkyl, piperidin4-yl-(1-4C)alkyl, piperidino-(2-4C)alkyl, piperazino-(2-4C)alkyl or morpholino-(2-4C)alkyl, and wherein adjacent carbon atoms in any (2-6C)alkylene chain within a $R^1$ substituent are optionally separated by the insertion into the chain of a group selected from O and $N(R^3)$, wherein $R^3$ is hydrogen or (1-4C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, (1-4C)alkoxy, amino, (1-4C)alkylamino and di-[(1-4C)alkyl]amino, and wherein any heterocyclyl group within a substituent on $R^1$ optionally bears 1, 2 or 3 substituents, which may be the same or different, selected from halogeno, hydroxy, amino, carbamoyl, (1-4C)alkyl, (2-4C)alkenyl, (2-4C)alkynyl, (1-4C)alkoxy, (1-4C)alkylsulfonyl, (1-4C)alkylamino, di-[(1-4C)alkyl]amino, N-(1-4C)alkylcarbamoyl, N,N-di-(1-4C)alkyl]carbamoyl and (2-4C)alkanoyl, and wherein any heterocyclyl group within a substituent on $R^1$ optionally bears 1 oxo substituent (preferably any oxo group on a morpholino group in $R^1$ is located at the 3 or 5 position on the morpholino ring);

(f) $R^1$ is selected from hydrogen, hydroxy, (1-4C)alkoxy, hydroxy-(2-4C)alkoxy, (1-3C)alkoxy-(2-4C)alkoxy or from a group of the formula:

$$Q^2\text{-}X^3\text{---}$$

wherein $X^3$ is O, and $Q^2$ is azetidin-1-yl-(2-4C)alkyl, pyrrolidin-1-yl-(2-4C)alkyl, piperidino-(2-4C)alkyl, piperazino-(2-4C)alkyl or morpholino-(2-4C)alkyl, and wherein any heterocyclyl group within a substituent on $R^1$ optionally bears 1, 2 or 3 substituents, which may be the same or different, selected from halogeno, hydroxy, amino, (1-4C)alkyl, (1-4C)alkoxy, (1-4C)alkylsulfonyl, (1-4C)alkylamino, di-[(1-4C)alkyl]amino, and (2-4C)alkanoyl, and wherein any heterocyclyl group within a substituent on $R^1$ optionally bears 1 oxo substituent;

(g) $R^1$ is selected from hydrogen, hydroxy, methoxy, ethoxy, propoxy, isopropyloxy, 2-hydroxyethoxy, 2-fluoroethoxy, cyclopropylmethoxy, 2-cyclopropylethoxy, vinyloxy, allyloxy, ethynyloxy, 2-propynyloxy, tetrahydrofuran-3-yloxy, tetrahydropyran-3-yloxy, tetrahydropyran-4-yloxy, tetrahydrofurfuryloxy, tetrahydrofuran-3-ylmethoxy, 2-(tetrahydrofuran-2-yl)ethoxy, 3-(tetrahydrofuran-2-yl) propoxy, 2-(tetrahydrofuran-3-yl)ethoxy, 3-(tetrahydrofuran-3-yl)propoxy, tetrahydropyranylmethoxy, 2-tetrahydropyranylethoxy, 3-tetrahydropyranylpropoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, pyrrolidin-1-yl, morpholino, piperidino and piperazin-1-yl, and wherein adjacent carbon atoms in any (2-6C)alkylene chain within a $R^1$ substituent are optionally separated by the insertion into the chain of a group selected from O, NH, $N(CH_3)$, $CH=CH$ and $C\equiv C$, and when $R^1$ is a vinyloxy, allyloxy, ethynyloxy or 2-propynyloxy group, the $R^1$ substituent optionally bears at the terminal $CH_2=$ or $HC\equiv$ position a substituent selected from N-(2-dimethylaminoethyl)carbamoyl, N-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$$Q^3\text{-}X^4\text{---}$$

wherein $X^4$ is a direct bond or is NHCO or $N(CH_3)CO$ and $Q^3$ is pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ group which is attached to 2 carbon atoms (other than a $CH_2$ group within a heterocyclyl ring) or any $CH_3$ group which is attached to a carbon atom within a $R^1$ substituent optionally bears on each said $CH_2$ or $CH_3$ group a substituent selected from hydroxy, amino, methoxy, ethoxy, methylsulfonyl, methylamino and dimethylamino, and wherein any heterocyclyl group within a substituent on $R^1$ optionally bears 1 or 2 substituents, which may be the same or different, selected from fluoro, chloro, trifluoromethyl, hydroxy, amino, methylamino, ethylamino, dimethylamino, diethylamino, carbamoyl, methyl, ethyl, n-propyl, isopropyl and methoxy, and any piperidin-3-ylmethyl, piperidin-4-ylmethyl or piperazin-1-yl group within a $R^1$ substituent is optionally N-substituted with 2-methoxyethyl, 3-methoxypropyl, 2-aminoethyl, 3-aminopropyl, 2-methylaminoethyl, 3-methylaminopropyl, 2-dimethylaminoethyl, 3-dimethylaminopropyl, acetyl or propionyl, and wherein any heterocyclyl group within a substituent on $R^1$ optionally bears 1 or 2 oxo substituents;

(h) $R^1$ is selected from hydrogen, hydroxy, (1-6C)alkoxy, (3-7C)cycloalkyl-oxy and (3-7C)cycloalkyl-(1-6C)alkoxy, and wherein any $CH_2$ or $CH_3$ group within a $R^1$ substituent optionally bears on each said $CH_2$ or $CH_3$ group one or more halogeno or (1-6C)alkyl substituents, or a substituent selected from hydroxy, cyano, amino, carboxy, carbamoyl, sulfamoyl, oxo, (1-6C)alkoxy, (1-6C)alkylthio, (1-6C)alkylsulfinyl, (1-6C)alkylsulfonyl, (1-6C)alkylamino, di-[(1-6C)alkyl]

amino, N-(1-6C)alkylcarbamoyl, N,N-di-[(1-6C)alkyl]carbamoyl, N-(1-6C)alkylsulfamoyl and N,N-di-[(1-6C)alkyl]sulfamoyl, (1-6C)alkanesulfonylamino and N-(1-6C)alkyl-(1-6C)alkanesulfonylamino;

(i) $R^1$ is selected from hydrogen, hydroxy, (1-6C)alkoxy, (3-7C)cycloalkyl-oxy and (3-7C)cycloalkyl-(1-6C)alkoxy, and wherein any $CH_2$ or $CH_3$ group within a $R^1$ substituent optionally bears on each said $CH_2$ or $CH_3$ group one or more fluoro or chloro substituents, or a substituent selected from hydroxy, amino, (1-4C)alkoxy, (1-4C)alkylamino and di-[(1-4C)alkyl]amino;

(j) $R^1$ is selected from hydrogen, hydroxy, (1-6C)alkoxy, (3-7C)cycloalkyl-oxy and (3-7C)cycloalkyl-(1-6C)alkoxy, and wherein adjacent carbon atoms in any (2-6C)alkylene chain within a $R^1$ substituent are optionally separated by the insertion into the chain of an O atom, and wherein any $CH_2$ or $CH_3$ group within a $R^1$ substituent optionally bears on each said $CH_2$ or $CH_3$ group one or more fluoro or chloro substituents, or a substituent selected from hydroxy and (1-4C)alkoxy;

(k) $R^1$ is selected from hydrogen, (1-6C)alkoxy, cyclopropyl-(1-4C)alkoxy, cyclobutyl-(1-4C)alkoxy, cyclopentyl-(1-4C)alkoxy, cyclohexyl-(1-6C)alkoxy, tetrahydrofuranyl-(1-4C)alkoxy and tetrahydropyranyl-(1-4C)alkoxy, and wherein adjacent carbon atoms in any (2-6C)alkylene chain within a $R^1$ substituent are optionally separated by the insertion into the chain of an O atom, and wherein any $CH_2$ or $CH_3$ group within a $R^1$ substituent optionally bears on each said $CH_2$ or $CH_3$ group one or more fluoro or chloro substituents, or a substituent selected from hydroxy and (1-3C)alkoxy;

(l) $R^1$ is selected from hydrogen, (1-6C)alkoxy, cyclopropylmethoxy and 2-cyclopropylethoxy, and wherein any $CH_2$ or $CH_3$ group within a $R^1$ substituent optionally bears on each said $CH_2$ or $CH_3$ group one or more fluoro or chloro substituents, or a substituent selected from hydroxy, methoxy and ethoxy;

(m) $R^1$ is selected from methoxy, ethoxy, propyloxy, isopropyloxy, cyclopropylmethoxy, 2-hydroxyethoxy, 2-fluoroethoxy, 2-methoxyethoxy, 2-ethoxyethoxy, 2,2-difluoroethoxy 2,2,2-trifluoroethoxy, 2-(pyrrolidin-1-yl)ethoxy, 3-(pyrrolidin-1-yl)propoxy, 2-piperidinoethoxy, 3-piperidinopropyl, 2-piperazinoethoxy, 3-piperazinopropoxy, 2-morpholinoethoxy and 3-morpholinopropoxy;

(n) $R^1$ is selected from hydrogen methoxy, ethoxy, propyloxy, isopropyloxy, cyclopropylmethoxy, 2-hydroxyethoxy, 2-fluoroethoxy, 2-methoxyethoxy, 2-ethoxyethoxy, 2,2-difluoroethoxy and 2,2,2-trifluoroethoxy;

(o) $R^1$ is selected from (1-4C)alkoxy, hydroxy-(2-4C)alkoxy and (1-3C)alkoxy-(2-3C)alkoxy;

(p) $R^1$ is selected from hydrogen and (1-3C)alkoxy (particularly $R^1$ is (1-3C)alkoxy such as methoxy, ethoxy and isopropyloxy);

(q) $R^1$ is hydrogen;

(r) $R^1$ is methoxy;

(s) each $R^2$, which may be the same or different, is selected from halogeno, cyano, nitro, hydroxy, amino, carboxy, (1-6C)alkyl, (2-8C)alkenyl, (2-8C)alkynyl, (1-6C)alkoxy, (1-6C)alkylamino, di-[(1-6C)alkyl]amino, (2-6C)alkanoyl, (2-6C)alkanoyloxy, and a group of the formula:

—$X^7$—$R^8$ wherein $X^7$ is a direct bond or is selected from O and N($R^9$), wherein $R^9$ is hydrogen or (1-6C)alkyl, and $R^8$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl;

(t) each $R^2$, which may be the same or different, is selected from halogeno, hydroxy, amino, (1-6C)alkyl, (2-8C)alkenyl, (2-8C)alkynyl, (1-6C)alkoxy, (1-6C)alkylamino and di-[(1-6C)alkyl]amino;

(u) each $R^2$, which may be the same or different, is selected from fluoro, chloro, bromo, iodo, cyano, hydroxy, trifluoromethyl, (1-4C)alkyl, (2-4C)alkenyl, (2-4C)alkynyl and (1-4C)alkoxy;

(v) each $R^2$, which may be the same or different, is selected from fluoro, chloro, bromo, (1-4C)alkyl, (2-4C)alkenyl and (2-4C)alkynyl;

(w) each $R^2$, which may be the same or different, is selected from fluoro, chloro, bromo, iodo, cyano, carbamoyl, hydroxy, trifluoromethyl, methyl, ethyl, isopropyl, methoxy, ethoxy, vinyl, allyl, ethynyl, 1-propynyl, 2-propynyl, N-methylcarbamoyl, N-ethylcarbamoyl and N,N-dimethylcarbamoyl;

(x) each $R^2$, which may be the same or different, is selected from fluoro, chloro, bromo, iodo, cyano, hydroxy, trifluoromethyl, methyl, ethyl, isopropyl, methoxy, ethoxy, vinyl, allyl, ethynyl, 1-propynyl, and 2-propynyl;

(y) each $R^2$, which may be the same or different, is selected from fluoro, chloro, bromo, cyano, hydroxy, trifluoromethyl, methyl, ethyl, methoxy, ethoxy and ethynyl;

(z) each $R^2$, which may be the same or different, is selected from fluoro, chloro, bromo and ethynyl;

(aa) each $R^2$, which may be the same or different, is selected from halogeno (particularly fluoro, chloro and bromo);

(bb) b is 1, 2 or 3 and one $R^2$ is at the meta (3-) position on the anilino group in Formula 1;

(cc) b is 1, 2 or 3 and each $R^2$, which may be the same or different, is as defined in any of (s) to (aa) above;

(dd) b is 1, 2 or 3, one $R^2$ is at the meta (3-) position on the anilino group in Formula 1 and is halogeno, and when b is 2 or 3 the other $R^2$ group(s), which may be the same or different, are as defined in any of any of (s) to (aa) above;

(ee) b is 1, 2 or 3, each $R^2$, which may be the same or different, is halogeno, and wherein one $R^2$ is at the meta (3-) position on the anilino group;

(ff) b is 1 or 2, each $R^2$, which may be the same or different, is halogeno (particularly fluoro, chloro or bromo) and wherein one $R^2$ is at the meta (3-) position and the other $R^2$ is at the ortho (2-) or para (4-) position on the anilino group;

(gg) b is 1 or 2, one $R^2$ is at the meta (3-) position on the anilino group and is chloro or bromo (particularly chloro), and when b is 2 the other $R^2$ group is selected from fluoro, chloro and bromo;

(hh) the anilino group at the 4-position on the quinazoline ring in Formula I is selected from 3-chloro-4-fluoroanilino, 3-bromo-2-fluoroanilino, 3-chloro-2-fluoroanilino, 2-fluoro-5-chloroanilino, 3-bromoanilino and 3-ethynylanilino;

(ii) the anilino group at the 4-position on the quinazoline ring in Formula I is selected from 3-chloro-4-fluoroanilino, 3-chloro-2-fluoroanilino, 2-fluoro-5-chloroanilino, 3-bromoanilino, 3-methylanilino and 3-ethynylanilino;

(jj) the anilino group at the 4-position on the quinazoline ring in Formula I is 3-chloro-4-fluoroanilino;

(kk) the anilino group at the 4-position on the quinazoline ring in Formula I is 3-chloro-2-fluoroanilino or 3-bromo-2-fluoroanilino (more particularly the anilino is 3-chloro-2-fluoroanilino);

(ll) $Q^1$ is selected from piperidin-3-yl and piperidin-4-yl;

(mm) $Q^1$ is piperidin-4-yl;

(nn) each W, which may be the same or different, is selected from halogeno, trifluoromethyl, hydroxy, oxo, (1-6C) alkyl, (1-6C)alkoxy, and from a group of the formula:

—$X^8$—$R^{10}$ wherein $X^8$ is a direct bond or is O, and $R^{10}$ is halogeno-(1-6C)alkyl, hydroxy-(1-6C)alkyl or (1-6C)alkoxy-(1-6C)alkyl;

(oo) each W, which may be the same or different, is selected from halogeno, hydroxy, oxo, (1-6C)alkyl and (1-6C)alkoxy;

(pp) each W, which may be the same or different, is selected from halogeno (particularly fluoro), hydroxy, (1-3C)alkyl and (1-3C)alkoxy;

(qq) a is 0, 1, or 2 and each W, which may be the same or different, is as defined in any of (nn) to (pp);

(rr) a is 0 or 1 and W is as defined in any of (nn) to (pp);

(ss) a is 0;

(tt) $Q^1$ is piperidin-4-yl, a is 0 or 1 and W is as defined in any of (nn) to (pp);

(uu) $X^1$ is CO;

(vv) $X^1$ is $SO_2$;

(ww) $X^2$ is a group of the formula:

—$(CR^{12}R^{13})_p$-$(Q^5)_m$-$(CR^{14}R^{15})_q$- wherein m is 0 or 1, p is 0, 1, 2, 3 or 4 and q is 0, 1, 2, 3 or 4, each of $R^{12}$, $R^{13}$, $R^{14}$ and $R^{15}$, which may be the same or different, is selected from hydrogen, (1-6C)alkyl, amino, (1-6C)alkylamino and di-[(1-6C)alkyl]amino, and $Q^5$ is selected from (3-7C)cycloalkylene and (3-7C)cycloalkenylene, and wherein any $CH_2$ or $CH_3$ group within an $X^2$ group, optionally bears on each said $CH_2$ or $CH_3$ group one or more halogeno or (1-6C)alkyl substituents, and wherein any $CH_2$ group which is attached to 2 carbon atoms or any $CH_3$ group which is attached to a carbon atom within a $X^2$ substituent optionally bears on each said $CH_2$ or $CH_3$ group a substituent selected from hydroxy, cyano, amino, (1-6C)alkoxy, (1-6C)alkylamino and di-[(1-6C)alkyl]amino;

(xx) $X^2$ is selected from a group of the formula -$(Q^5)_m$-$(CR^{14}R^{15})_q$- and a group of the formula —$(CR^{12}R^{13})_q$-$(Q^5)_m$-, wherein m is 0 or 1, q is 1, 2, 3 or 4, and $Q^5$, $R^{12}$, $R^{13}$, $R^{14}$ and $R^{15}$ are as hereinbefore defined;

(yy) $X^2$ is a group of the formula -$Q^5$-, for example (3-7C) cycloalkylene such as cyclopropylidene;

(zz) $X^2$ is selected from cyclopropylene, cyclopbutylene, cyclopentylene, cyclohexylene, methylene-(3-6C)cycloalkylene, (3-6C)cycloalkylene-methylene-, ethylene-(3-6C)cycloalkylene and (3-6C)cycloalkylene-ethylene-, and wherein and wherein any $CH_2$ or $CH_3$ group within $X^2$, optionally bears on each said $CH_2$ or $CH_3$ group one or more halogeno or (1-6C)alkyl substituents or a substituent selected from hydroxy, amino, (1-6C)alkoxy, (1-6C)alkylamino and di-[(1-6C)alkyl]amino;

(aaa) $X^2$ is a group of the formula —$(CR^{12}R^{13})_q$—, q is 1, 2, 3 or 4 (particularly 1 or 2), each of $R^{12}$ and $R^{13}$, which may be the same or different, is selected from hydrogen and (1-6C)alkyl, and wherein and wherein any $CH_2$ or $CH_3$ group within $X^2$, optionally bears on each said $CH_2$ or $CH_3$ group one or more halogeno substituents, and wherein any $CH_2$ group which is attached to 2 carbon atoms or any $CH_3$ group which is attached to a carbon atom within a $X^2$ substituent optionally bears on each said $CH_2$ or $CH_3$ group a substituent selected from hydroxy, amino, (1-6C)alkoxy, (1-6C)alkylamino and di-[(1-6C)alkyl]amino;

(bbb) $X^2$ is a group of the formula —$(CR^{12}R^{13})_q$—, q is 1, 2 or 3, each of $R^{12}$ and $R^{13}$, which may be the same or different, is selected from hydrogen and (1-6C)alkyl, and wherein any $CH_2$ or $CH_3$ group within an $X^2$ group, optionally bears on each said $CH_2$ or $CH_3$ group one or more halogeno substituents, and wherein any $CH_2$ group which is attached to 2 carbon atoms or any $CH_3$ group which is attached to a carbon atom within a $X^2$ substituent optionally bears on each said $CH_2$ or $CH_3$ group a substituent selected from hydroxy, and (1-6C)alkoxy;

(ccc) $X^2$ is a group of the formula —$(CR^{12}R^{13})_q$—$(CR^{12aa}R^{13aa})$—, q is 1, 2 or 3 (particularly 1 or 2, more particularly 1), each of $R^{12}$, $R^{13}$ and $R^{13aa}$, which may be the same or different, is selected from hydrogen and (1-6C)alkyl, $R^{12aa}$ is selected from amino, (1-6C)alkylamino and di-[(1-6C)alkyl]amino, and wherein any $CH_2$ or $CH_3$ group within an $X^2$ group, optionally bears on each said $CH_2$ or $CH_3$ group one or more halogeno substituents, and wherein any $CH_2$ group which is attached to 2 carbon atoms or any $CH_3$ group which is attached to a carbon atom within a $X^2$ substituent optionally bears on each said $CH_2$ or $CH_3$ group a substituent selected from hydroxy, amino, (1-6C)alkoxy, (1-6C)alkylamino and di-[(1-6C)alkyl]amino;

(ddd) $X^2$ is a group of the formula —$(CR^{12}R^{13})_q$—, q is 1, 2, 3 or 4 (particularly 1 or 2, more particularly 1), each of $R^{12}$ and $R^{13}$, which may be the same or different, is selected from hydrogen and (1-6C)alkyl, provided that at least one of the $R^{12}$ or $R^{13}$ groups in $X^2$ is (1-6C)alkyl, and wherein any $CH_2$ or $CH_3$ group within an $X^2$ group, optionally bears on each said $CH_2$ or $CH_3$ group one or more halogeno substituents, and wherein any $CH_2$ group which is attached to 2 carbon atoms or any $CH_3$ group which is attached to a carbon atom within a $X^2$ substituent optionally bears on each said $CH_2$ or $CH_3$ group a substituent selected from hydroxy, and (1-6C)alkoxy;

(eee) $X^2$ is selected from a group of the formula —$(CR^{12}R^{13})$—, —$(CR^{12}R^{13}CH_2)$—, —$(CR^{12}R^{13}CH_2CH_2)$—, —$(CH_2CR^2R^{13})$— and —$(CH_2CH_2CR^{12}R^{13})$—, each of $R^{12}$ and $R^3$, which may be the same or different, is selected from hydrogen and (1-6C)alkyl, and wherein any $CH_2$ or $CH_3$ group within $X^2$, optionally bears on each said $CH_2$ or $CH_3$ group one or more halogeno substituents, and wherein any $CH_2$ group which is attached to 2 carbon atoms or any $CH_3$ group which is attached to a carbon atom within a $X^2$ substituent optionally bears on each said $CH_2$ or $CH_3$ group a substituent selected from hydroxy, amino, (1-6C)alkoxy, (1-6C)alkylamino and di-[(1-6C)alkyl]amino;

(fff) $X^2$ is selected from a group of the formula —$(CR^{12}R^{13})$—, —$(CR^{12}R^{13}CH_2)$—, —$(CR^{12}R^{13}CH_2CH_2)$—, —$(CH_2CR^{12}R^{13})$— and —$(CH_2CH_2CR^{12}R^{13})$—, each of $R^{12}$ and $R^3$, which may be the same or different, is selected from hydrogen and (1-6C)alkyl, provided that at least one of $R^{12}$ or $R^{13}$ is a branched (1-6C)alkyl group, and wherein any $CH_2$ or $CH_3$ group within $X^2$, optionally bears on each said $CH_2$ or $CH_3$ group one or more halogeno substituents, and wherein any $CH_2$ group which is attached to 2 carbon atoms or any $CH_3$ group which is attached to a carbon atom within a $X^2$ substituent optionally bears on each said $CH_2$ or $CH_3$ group a substituent selected from hydroxy, amino, (1-6C)alkoxy, (1-6C)alkylamino and di-[(1-6C)alkyl]amino;

(ggg) $X^2$ is selected from a group of the formula —$(CR^{12}R^{13})$—, —$(CR^{12}R^{13}CH_2)$—, —$(CR^{12}R^{13}CH_2CH_2)$—, —$(CH_2CR^{12}R^{13})$— and —$(CH_2CH_2CR^{12}R^{13})$—, each of $R^{12}$ and $R^{13}$, which may be the same or different, is selected from hydrogen and (1-6C)alkyl, provided that at least one of $R^2$ or $R^{13}$ in $X^2$ is a branched alkyl group, which branched alkyl group is preferably selected from iso-propyl, iso-butyl, sec-butyl and tert-butyl, and wherein any $CH_2$ or $CH_3$ group within $X^2$, optionally bears on each said $CH_2$ or $CH_3$ group one or more fluoro or chloro substituents, and wherein any $CH_2$ group which is attached to 2 carbon atoms or any $CH_3$ group which is attached to a carbon atom within a $X^2$ substituent optionally bears on each said $CH_2$ or $CH_3$ group a substituent selected from hydroxy and (1-3C)alkoxy;

(hhh) $X^2$ is selected from a group of the formula —$CH_2$—, —$CH_2CH_2$—, —$CH_2CH_2CH_2$—$(CR^{12}R^{13})$—, —$(CR^{12}R^{13}CH_2)$— and —$(CH_2CR^{12}R^{13})$— wherein each of $R^{12}$ and $R^{13}$, which may be the same or different, is selected from hydrogen, (1-4C)alkyl, hydroxy-(1-4C)alkyl and (1-4C)alkoxy-(1-4C)alkyl, provided that $R^{12}$ and $R^{13}$ are not both hydrogen;

(iii) $X^2$ is selected from a group of the formula —$CH_2$—, —$CH_2CH_2$—, —$(CHR^{12a})$, —$(CHR^{12a}CH_2)$—, —$(C(R^{12a})_2CH_2)$—, —$(CH_2C(R^{12a})_2)$— and —$(CH_2CHR^{12b})$—, wherein each $R^{12a}$, which may be the same or different, is selected from (1-4C)alkyl, hydroxy-(1-4C)alkyl, (1-3C)alkoxy-(1-4C)alkyl, amino-(1-4C)alkyl, (1-4C)alkylamino-(1-4C)alkyl and di-[(1-4C)alkyl]-amino-(1-4C)alkyl, and wherein $R^{12b}$ is selected from hydroxy, amino, (1-4C)alkyl, (1-4C)alkoxy, (1-4C)alkylamino, di-[(1-4C)alkyl]-amino, hydroxy-(1-4C)alkyl, (1-3C)alkoxy-(1-4C)alkyl, amino-(1-4C)alkyl, (1-4C)alkylamino-(1-4C)alkyl and di-[(1-4C)alkyl]-amino-(1-4C)alkyl;

(jjj) $X^2$ is selected from a group of the formula —$CH_2$—, —$CH_2CH_2$—, —$(CHR^{12a})$—, —$(CHR^{12a}CH_2)$— and —$(CH_2CHR^{12b})$— wherein $R^{12a}$ is selected from hydrogen, (1-4C)alkyl, hydroxy-(1-4C)alkyl, (1-3C)alkoxy-(1-4C)alkyl, amino-(1-4C)alkyl, (1-4C)alkylamino-(1-4C)alkyl and di-[(1-4C)alkyl]-amino-(1-4C)alkyl, and wherein $R^{12b}$ is selected from hydrogen, hydroxy, amino, (1-4C)alkyl, (1-4C)alkoxy, hydroxy-(1-4C)alkyl, (1-3C)alkoxy-(1-4C)alkyl, amino-(1-4C)alkyl, (1-4C)alkylamino-(1-4C)alkyl and di-[(1-4C)alkyl]-amino-(1-4C)alkyl;

(kkk) $X^2$ is selected from a group of the formula —$CH_2$—, —$CH_2CH_2$—, —$(CHR^{12a})$—, —$(CHR^{12a}CH_2)$—, —$(C(R^{12a})_2CH_2)$—, —$(CH_2C(R^{12a})_2)$— and —$(CH_2CHR^{12b})$—, wherein each $R^{12a}$, which may be the same or different, is (1-4C)alkyl, and wherein $R^{12b}$ is selected from amino, (1-4C)alkylamino and di-[(1-4C)alkyl]-amino;

(lll) $X^2$ is selected from a group of the formula —$(CHR^{12a})$—, —$(CHR^{12a}CH_2)$—, —$(C(R^{12a})_2CH_2)$—, —$(CH_2C(R^{12a})_2)$— and —$(CH_2CHR^{12b})$—, wherein each $R^{12a}$, which may be the same or different, is (1-4C)alkyl (particularly (1-3C)alkyl), and wherein $R^{12b}$ is selected from amino, (1-4C)alkylamino and di-[(1-4C)alkyl]-amino (particularly $R^{12b}$ is selected from (1-4C)alkylamino and di-[(1-4C)alkyl]-amino, more particularly di-[(1-3C)alkyl]-amino);

(mmm) $X^2$ is selected from a group of the formula —$CH_2$—, —$CH_2CH_2$—, —$(CHR^{12})$—, —$(CHR^{12}CH_2)$— and —$(CH_2CHR^{12})$— wherein $R^{12}$ is selected from hydrogen, (1-4C)alkyl, hydroxy-(1-4C)alkyl, (1-3C)alkoxy-(1-4C)alkyl, amino-(1-4C)alkyl, (1-4C)alkylamino-(1-4C)alkyl and di-[(1-4C)alkyl]-amino-(1-4C)alkyl;

(nnn) $X^2$ is selected from a group of the formula —$CH_2$—, —$CH_2CH_2$—, —$(CHR^{12a})$—, —$(CHR^{12a}CH_2)$—, —$(C(R^{12a})_2CH_2)$—, —$(CH_2C(R^{12a})_2)$— and —$(CH_2CHR^{12a})$—, wherein each $R^{12a}$, which may be the same or different, is (1-4C)alkyl;

(ooo) $X^2$ is selected from a group of the formula —$(CHR^{12a})$—, —$(CHR^{12a}CH_2)$—, —$(C(R^{12a})_2CH_2)$—, —$(CH_2C(R^{12a})_2)$— and —$(CH_2CHR^{12a})$— (particularly, $X^2$ is —$CHR^{12a}$)—), wherein each $R^{12a}$, which may be the same or different, is (1-4C)alkyl;

(ppp) $X^2$ is selected from a group of the formula —$(CH_2)_q$—, wherein q is 1, 2 or 3, particularly q is 1 or 2, more particularly 1;

(qqq) Z is selected from hydroxy, amino, (1-6C)alkylamino, di-[(1-6C)alkyl]amino, (1-6C)alkoxy, (1-6C)alkylsulfonyl, (1-6C)alkanesulfonylamino and N-(1-6C)alkyl-(1-6C)alkanesulfonylamino and a group of the formula:

$$Q^6\text{-}X^9—$$

wherein $X^9$ is a direct bond or is selected from O, $N(R^{16})$, $SO_2$ and $SO_2N(R^{16})$, wherein $R^{16}$ is hydrogen or (1-6C)alkyl, and $Q^6$ is (3-7C)cycloalkyl, (3-7C)cycloalkyl-(1-4C)alkyl, (3-7C)cycloalkenyl, (3-7C)cycloalkenyl-(1-4C)alkyl, heterocyclyl or heterocyclyl-(1-4C)alkyl, provided that when $X^9$ is a direct bond, $Q^6$ is heterocyclyl, and provided that when m, p and q are all 0, then Z is heterocyclyl, and wherein any heterocyclyl group in Z is a monocyclic fully saturated 4, 5, 6 or 7-membered heterocyclyl group containing 1 or 2 heteroatoms selected from oxygen, nitrogen and sulfur, and wherein and wherein any $CH_2$ or $CH_3$ group within a Z group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein any heterocyclyl group within a Z substituent optionally bears one or more (for example 1, 2 or 3) substitutents which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$-X^{10}-R^{18}$$

wherein $X^{10}$ is a direct bond or is selected from O, CO, $SO_2$ and $N(R^{19})$, wherein $R^{19}$ is hydrogen or (1-4C)alkyl, and $R^{18}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl;

(rrr) Z is selected from hydroxy, amino, (1-6C)alkylamino, di-[(1-6C)alkyl]amino, (1-6C)alkoxy and a group of the formula:

$$Q^6-X^9-$$

wherein $X^9$ is a direct bond or is selected from O and $N(R^{16})$, wherein $R^{16}$ is hydrogen or (1-6C)alkyl, and $Q^6$ is (3-7C)cycloalkyl, (3-7C)cycloalkyl-(1-4C)alkyl, (3-7C)cycloalkenyl, (3-7C)cycloalkenyl-(1-4C)alkyl, heterocyclyl or heterocyclyl-(1-4C)alkyl, provided that when $X^9$ is a direct bond, $Q^6$ is heterocyclyl, and provided that when m, p and q are all 0, then Z is heterocyclyl, and wherein any heterocyclyl group in Z is a monocyclic non-aromatic fully saturated or partially saturated 4, 5, 6 or 7-membered heterocyclyl group containing 1 heteroatom selected from oxygen and nitrogen and optionally a further heteroatom selected from oxygen, nitrogen and sulfur, and wherein and wherein any $CH_2$ or $CH_3$ group within a Z group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein any heterocyclyl group within a Z substituent optionally bears one or more (for example 1, 2 or 3) substitutents which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$-X^{10}-R^{18}$$

wherein $X^{10}$ is a direct bond or is selected from O, CO, $SO_2$ and $N(R^{19})$, wherein $R^{19}$ is hydrogen or (1-4C)alkyl, and $R^{18}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl;

(sss) Z is selected from hydroxy, amino, (1-6C)alkylamino, di-[(1-6C)alkyl]amino, (1-6C)alkoxy and a group of the formula:

$$Q^6-X^9-$$

wherein $X^9$ is a direct bond or is selected from O and $N(R^{16})$, wherein $R^{16}$ is hydrogen or (1-6C)alkyl, and $Q^6$ is (3-7C)cycloalkyl, (3-7C)cycloalkyl-(1-4C)alkyl, (3-7C)cycloalkenyl, (3-7C)cycloalkenyl-(1-4C)alkyl, heterocyclyl or heterocyclyl-(1-4C)alkyl, provided that when $X^9$ is a direct bond, $Q^6$ is heterocyclyl, and provided that when m, p and q are all 0, then Z is heterocyclyl, and wherein any heterocyclyl group in Z is selected from tetrahydrofuranyl, 1,3-dioxolanyl, tetrahydropyranyl, 1,4-dioxanyl, oxepanyl, pyrrolidinyl, morpholinyl, piperidinyl, homopiperidinyl, piperazinyl and homopiperazinyl, which heterocyclyl group may be carbon or nitrogen linked to the group to which it is attached, and wherein and wherein any $CH_2$ or $CH_3$ group within a Z group, other than a $CH_2$ group within a heterocyclyl ring, optionally bears on each said $CH_2$ or $CH_3$ group one or more halogen or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein any heterocyclyl group within a Z substituent optionally bears one or more (for example 1, 2 or 3) substitutents which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$$-X^{10}-R^{18}$$

wherein $X^{10}$ is a direct bond or is selected from O, CO, $SO_2$ and $N(R^{19})$, wherein $R^{19}$ is hydrogen or (1-4C)alkyl, and $R^{18}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl;

(ttt) Z is selected from hydroxy, amino, (1-6C)alkylamino, di-[(1-6C)alkyl]amino, (1-6C)alkoxy and a group of the formula:

$$Q^6-X^9-$$

wherein $X^9$ is a direct bond and $Q^6$ is heterocyclyl, and provided that when m, p and q are all 0, then Z is heterocyclyl (preferably carbon linked to $X^1$), and wherein any heterocyclyl group in Z is selected from azetidinyl, tetrahydrofuranyl, 1,3-dioxolanyl, tetrahydropyranyl, 1,4-dioxanyl, oxepanyl, pyrrolidinyl, morpholinyl, piperidinyl, homopiperidinyl, piperazinyl and homopiperazinyl, and wherein and wherein any $CH_2$ or $CH_3$ group within a Z group optionally bears on each said $CH_2$ or $CH_3$ group one or more halogeno or (1-6C)alkyl substituents or a substituent selected from hydroxy and (1-6C)alkoxy, and wherein any heterocyclyl group within a Z substituent optionally bears one or more (for example 1, 2 or 3) substitutents which may be the same or different, selected from halogeno, trifluoromethyl, cyano, nitro, hydroxy, amino, formyl, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino and (2-6C)alkanoyl;

(uuu) Z is selected from hydroxy, amino, (1-6C)alkylamino, hydroxy-(2-6C)alkylamino, (1-4C)alkoxy-(2-6C)alkylamino, di-[(1-6C)alkyl]amino, N-[hydroxy-(2-6C)alkyl]-N-(1-6C)alkylamino, N-[(1-4C)alkoxy-(2-6C)alkyl]-N-(1-6C)alkylamino, di-[hydroxy-(2-6C)alkyl]-amino, di-[(1-4C)alkoxy-(2-6C)alkyl]amino, N-[(1-4C)alkoxy-(2-6C)alkyl]-N-[hydroxy-(2-6C)alkyl]-amino, (1-6C)alkoxy, hydroxy-(2-6C)alkoxy, (1-4C)alkoxy-(2-6C)alkoxy, azetidin-1-yl, pyrrolidin-1-yl, piperidino, piperazin-1-yl, morpholino, homopiperidin-1-yl homopiperazin-1-yl, tetrahydrofuran-2-yl, tetrahydrofuran-3-yl, 1,3-dioxolanyl, tetrahydropyranyl, 1,4-dioxanyl and a group of the formula:

$Q^6-X^9-$ wherein $X^9$ is selected from O and $N(R^{16})$, wherein $R^{16}$ is hydrogen or (1-4C)alkyl, and $Q^6$ is (3-7C)cycloalkyl, (3-7C)cycloalkyl-(1-4C)alkyl, (3-7C)cycloalkenyl, (3-7C)cycloalkenyl-(1-4C)alkyl, heterocyclyl or heterocyclyl-(1-4C)alkyl, and wherein any heterocyclyl group in $Q^6$ is selected from tetrahydrofuranyl, 1,3-dioxolanyl, tetrahydropyranyl, 1,4-dioxanyl, oxepanyl, pyrrolidinyl, morpholinyl, tetrahydro-1,4-thiazinyl, piperidinyl, homopiperidinyl, piperazinyl, homopiperazinyl, which heterocyclyl group may be carbon or nitrogen linked to the group to which it is attached, and provided that when m, p and q are all 0, then Z is heterocyclyl, preferably one of the above mentioned heterocyclyl groups that may be represented by $Q^6$, (which heterocyclyl group is preferably carbon linked to $X^1$), and wherein and wherein any $CH_2$ or $CH_3$ group within a Z group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein any heterocyclyl group within a Z substituent optionally bears one or more (for example 1, 2 or 3) substitutents which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

$-X^{10}-R^{18}$ wherein $X^{10}$ is a direct bond or is selected from O, CO, $SO_2$ and $N(R^{19})$, wherein $R^{19}$ is hydrogen or (1-4C)alkyl, and $R^{18}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl;

(vvv) Z is selected from amino, (1-6C)alkylamino, hydroxy-(2-6C)alkylamino, (1-4C)alkoxy-(2-6C)alkylamino, di-[(1-6C)alkyl]amino, N-[hydroxy-(2-6C)alkyl]-N-1-6C)alkylamino, N-[(1-4C)alkoxy-(2-6C)alkyl]-N-1-6C)alkylamino, di-[hydroxy-2-6C)alkyl]-amino, di-[(1-4C)alkoxy-(2-6C)alkyl]amino, N-[(1-4C)alkoxy-(2-6C)alkyl]-N-[hydroxy-(2-6C)alkyl]-amino, azetidin-1-yl, pyrrolidin-1-yl, piperidino, piperazin-1-yl, morpholino, homopiperidin-1-yl and homopiperazin-1-yl, and wherein and wherein any $CH_2$ or $CH_3$ group within a Z group, optionally bears on each said $CH_2$ or $CH_3$ group one or more fluoro substituents or a substituent selected from hydroxy, cyano, amino, (2-6C)alkenyl, (2-6C)alkynyl, (1-6C)alkoxy, (1-6C)alkylamino and di-[(1-6C)alkyl]amino, and wherein any heterocyclyl group within a Z substituent optionally bears one or more (for example 1, 2 or 3) substitutents which may be the same or different, selected from halogeno, cyano, hydroxy, amino, (1-4C)alkyl, (1-4C)alkoxy, (2-4C)alkanoyl, (1-4C)alkylamino and di-[(1-4C)alkyl]amino, and provided that when m, p and q are all 0, then Z is one of the above mentioned heterocyclyl groups that may be represented by Z, such as pyrrolidin-1-yl or piperidino (preferably the sum of m+p+q is at least 1);

(www) Z is selected from hydroxy, (1-6C)alkoxy, hydroxy-(2-6C)alkoxy, (1-4C)alkoxy-(2-6C)alkoxy, tetrahydrofuran-2-yl, tetrahydrofuran-3-yl, 1,3-dioxolanyl, 1,4-dioxanyl, tetrahydropyranyl and a group of the formula:

$Q^6-X^9-$ wherein $X^9$ is O, and $Q^6$ is (3-7C)cycloalkyl, (3-7C)cycloalkyl-(1-4C)alkyl, (3-7C)cycloalkenyl, (3-7C)cycloalkenyl-(1-4C)alkyl, heterocyclyl or heterocyclyl-(1-4C)alkyl, wherein any heterocyclyl group represented by $Q^6$ is preferably selected from tetrahydrofuran-2-yl, tetrahydrofuran-3-yl, 1,3-dioxolanyl, 1,4-dioxanyl and tetrahydropyranyl, and provided that when m, p and q are all 0, then Z is selected from tetrahydrofuran-2-yl, tetrahydrofuran-3-yl, 1,3-dioxolanyl, 1,4-dioxanyl, tetrahydropyranyl and oxepanyl, and wherein any $CH_2$ or $CH_3$ group within a Z group, optionally bears on each said $CH_2$ or $CH_3$ group one or more fluoro substituents or a substituent selected from hydroxy, cyano, amino, (2-6C)alkenyl, (2-6C)alkynyl, (1-6C)alkoxy, (1-6C)alkylamino and di-[(1-6C)alkyl]amino, and wherein any heterocyclyl group within a Z substituent optionally bears one or more (for example 1, 2 or 3) substitutents which may be the same or different, selected from halogeno, cyano, hydroxy, amino, (1-4C)alkyl, (1-4C)alkoxy, (1-4C)alkylamino and di-[(1-4C)alkyl]amino;

(xxx) Z is selected from hydroxy, amino, (1-6C)alkylamino, hydroxy-(2-6C)alkylamino, (1-4C)alkoxy-(2-6C)alkylamino, di-[(1-6C)alkyl]amino, N-[hydroxy-(2-6C)alkyl]-N-(1-6C)alkylamino, N-[(1-4C)alkoxy-(2-6C)alkyl]-N-(1-6C)alkylamino, di-[hydroxy-(2-6C)alkyl]-amino, di-[(1-4C)alkoxy-(2-6C)alkyl]amino, N-[(1-4C)alkoxy-(2-6C)alkyl]-N-[hydroxy-(2-6C)alkyl]-amino, (1-6C)alkoxy, hydroxy-(2-6C)alkoxy and (1-4C)alkoxy-(2-6C)alkoxy, and wherein the sum of m+p+q is at least 1;

(yyy) Z is selected from hydroxy, amino, (1-6C)alkylamino, di-[(1-6C)alkyl]amino, (1-6C)alkoxy, hydroxy-(2-6C)alkoxy and (1-4C)alkoxy-(2-6C)alkoxy, and the sum of m+p+q is at least 1;

(zzz) Z is selected from hydroxy, (1-6C)alkoxy, hydroxy-(2-6C)alkoxy and (1-4C)alkoxy-(2-4C)alkoxy), and the sum of m+p+q is at least 1;

(aaaa) Z is selected from hydroxy, methoxy, ethoxy, 2-hydroxyethoxy, 2-methoxyethoxy, amino, methylamino, ethylamino, N-(2-hydroxyethyl)amino, N-(2-methoxyethyl)amino, dimethylamino, N-methyl-N-ethylamino, diethylamino, N-(2-hydroxyethyl)-N-methylamino, N-(2-hydroxyethyl)-N-ethylamino, N,N-di-(2-hydroxyethyl)amino, N-(2-methoxyethyl)-N-methylamino, N-(2- methoxyethyl)-N-ethylamino, pyrrolidin-1-yl, piperidino, piperazin-1-yl, morpholino, tetrahydrofuranyl and tetrahydropyranyl, and wherein any heterocyclyl group within Z optionally bears 1 or 2 substituents, which may be the same or different, selected from fluoro, chloro, hydroxy, (1-4C)alkyl, (2-4C)alkanoyl and (1-4C)alkoxy, and provided that when m, p and q are all 0, then Z is one of the above mentioned heterocyclyl groups that may be represented by Z, such as pyrrolidin-1-yl, tetrahydrofuranyl or piperidino (preferably the sum of m+p+q is at least 1);

(bbbb) Z is selected from pyrrolidin-1-yl, piperidino, piperazin-1-yl, morpholino, homopiperidin-1-yl, homopiperazin-1-yl, (particularly Z is selected from pyrrolidin-1-yl, piperidino, piperazin-1-yl and morpholino), and wherein the heterocyclyl group within Z optionally bears one or more (for example 1, 2 or 3) substituents, which may be the same or different selected from fluoro, chloro, cyano, hydroxy, amino, carbamoyl, (1-4C)alkyl, (1-4C)alkoxy, (1-4C)alkylamino, di-[(1-4C)alkyl]amino, N-(1-4C)alkylcarbamoyl, N,N-di-[(1-4C)alkyl]carbamoyl, acetyl, propionyl, 2-fluoroethyl, 2-hydroxyethyl, 2-methoxyethyl, cyanomethyl, hydroxyacetyl, aminoacetyl, methylaminoacetyl, ethylaminoacetyl, dimethylaminoacetyl and N-methyl-N-ethylaminoacetyl (preferably the sum of m+p+q is at least 1);

(cccc) Z is selected from hydroxy, (1-4C)alkoxy, tetrahydrofuranyl and tetrahydropyranyl and wherein any tetrahydrofuranyl or tetrahydropyranyl group within Z optionally bears one or two substituents, which may be the same or different selected from fluoro, chloro, hydroxy, (1-4C)alkyl and (1-4C)alkoxy, and provided that when m, p and q are all 0, then Z is selected from tetrahydrofuranyl and tetrahydropyranyl (preferably the sum of m+p+q is at least 1);

(dddd) Z is hydroxy or (1-4C)alkoxy (particularly Z is hydroxy), and the sum of m+p+q is at least 1;

(eeee) Z is as defined in any of (qqq) to (dddd) above, and wherein $X^2$ is selected from $—CH_2—$, $—CH_2CH_2—$, $—(CR^{12}R^{13})—$, $—(CR^{12}R^{13}CH_2)—$, $—(CH_2CR^{12}R^{13})—$ and (3-6C)cycloalkenylene (for example cyclopropylene such as cyclopropylidene), wherein each of $R^{12}$ and $R^{13}$, which may be the same or different, is selected from hydrogen, (1-4C)alkyl, hydroxy-(1-4C)alkyl, and (1-3C)alkoxy-(1-4C)alkyl, provided that $R^{12}$ and $R^{13}$ are not both hydrogen, and wherein $X^1$ is CO;

(ffff) Z is as defined in any of (qqq) to (dddd) above;

$X^2$ is selected from a group of the formula $—CH_2—$, $—CH_2CH_2—$, $—(CHR^{12a})—$, $—(CHR^{12a}CH_2)—$, $—(C(R^{12a})_2CH_2)—$, $—(CH_2C(R^{12a})_2)—$ and $—(CH_2CHR^{12b})—$ (particularly, $X^2$ is $—(CHR^{12a})—$), wherein each $R^{12a}$, which may be the same or different, is selected from (1-4C)alkyl, hydroxy-(1-4C)alkyl and (1-3C)alkoxy-(1-4C)alkyl, and wherein $R^{12b}$ is selected from hydroxy, amino, (1-4C)alkyl, (1-4C)alkoxy, (1-4C)alkylamino, di-[(1-4C)alkyl]-amino, hydroxy-(1-4C)alkyl, (1-3C)alkoxy-(1-4C)alkyl, amino-(1-4C)alkyl, (1-4C)alkylamino-(1-4C)alkyl and di-[(1-4C)alkyl]-amino-(1-4C)alkyl; and wherein $X^1$ is CO;

(gggg) Z is selected from hydroxy and (1-4C)alkoxy, $X^2$ is selected from a group of the formula $—CH_2—$, $—CH_2CH_2—$, $—(CHR^{12a})—$, $—(CHR^{12a}CH_2)—$, $—C(R^{12a})_2CH_2)—$, $—(CH_2C(R^{12a})_2)—$ and $—(CH_2CHR^{12b})—$ (particularly, $X^2$ is $—(CHR^{12a})—$), wherein each $R^{12a}$, which may be the same or different, is (1-4C)alkyl, and wherein $R^{12b}$ is selected from hydroxy, amino, (1-4C)alkyl, (1-4C)alkoxy, (1-4C)alkylamino and di-[(1-4C)alkyl]-amino, and wherein $X^1$ is CO;

(hhhh) $Z-X^2—X^1$ is hydroxy-(2-4C)alkanoyl, for example hydroxyacetyl, 2-hydroxypropionyl or 3-hydroxypropionyl, particularly $Z-X^2—X^1$ is 2-hydroxypropionyl);

(iiii) $Z-X^2—X^1$ is (1-4C)alkoxy-(2-4C)alkanoyl, for example methoxyacetyl, 2-methoxypropionyl or 3-methoxypropionyl);

(jjjj) $Z-X^2—X^1$ is selected from amino-(2-4C)alkanoyl, (1-4C)alkylamino-(2-4C)alkanoyl and di-[(1-4C)alkyl]amino-(2-4C)alkanoyl (for example $Z-X^2—X^1$ is di-[(1-4C)alkyl]amino-acetyl such as dimethylaminoacetyl);

(kkkk) $Z-X^2—$ is selected from tetrahydrofuranyl, 1,3-dioxolanyl, tetrahydropyranyl, 1,4-dioxanyl, oxepanyl, pyrrolidinyl, morpholinyl, piperidinyl, homopiperidinyl, piperazinyl and homopiperazinyl, which heterocyclyl is linked to the carbonyl group in Formula I, by a ring carbon, and wherein the heterocyclyl group within $Z-X^2$ optionally bears 1 or 2 substituents, which may be the same or different, selected from fluoro, chloro, hydroxy, (1-4C)alkyl, (1-4C)alkoxy and (2-4C)alkanoyl;

(llll) $Z-X^2—$ is selected from tetrahydrofuranyl, 1,3-dioxolanyl, tetrahydropyranyl, 1,4-dioxanyl, oxepanyl (for example $Z-X^2$ is selected tetrahydrofuran-2-yl or tetrahydropyran-2-yl);

(mmmm) $Z-X^2—$ is selected from pyrrolidinyl, morpholinyl, piperidinyl, homopiperidinyl, piperazinyl and homopiperazinyl, which heterocyclyl is linked to $X^1$ in Formula I, by a ring carbon, and wherein the heterocyclyl group within $Z-X^2$ optionally bears 1 or 2 substituents, which may be the same or different, selected from fluoro, chloro, hydroxy, (1-4C)alkyl, (1-4C)alkoxy and (2-4C)alkanoyl; and (nnnn) $Z-X^2$ is selected from pyrrolidin-1-yl, piperidino, morpholino, piperazin-1-yl, homopiperidin-1-yl and homopiperazin-1-yl, and wherein the heterocyclyl group within $Z-X^2$ optionally bears 1 or 2 substituents, which may be the same or different, selected from fluoro, chloro, hydroxy, (1-4C)alkyl, (1-4C)alkoxy and (2-4C)alkanoyl.

A particular embodiment of the present invention is a quinazoline derivative of the Formula I wherein:

$R^1$ is selected from hydrogen, (1-6C)alkoxy, cyclopropyl-(1-4C)alkoxy, cyclobutyl-(1-4C)alkoxy, cyclopentyl-(1-4C)alkoxy, cyclohexyl-(1-6C)alkoxy, tetrahydrofuranyl-(1-4C)alkoxy and tetrahydropyranyl-(1-4C)alkoxy, and wherein any $CH_2$ or $CH_3$ group within a $R^1$ substituent optionally bears on each said $CH_2$ or $CH_3$ group one or more halogeno substituents, or a substituent selected from hydroxy and (1-4C)alkoxy;

b is 1, 2 or 3;

each $R^2$, which may be the same or different, is selected from halogeno (particularly fluoro, chloro or bromo), cyano, hydroxy, trifluoromethyl, (1-4C)alkyl, (2-4C)alkenyl, (2-4C)alkynyl and (1-4C)alkoxy;

$Q^1$ is piperidin-4-yl;

a is 0, 1 or 2;

each W, which may be the same or different, is selected from halogeno (particularly fluoro), trifluoromethyl, hydroxy, oxo, (1-6C)alkyl, (1-6C)alkoxy, and from a group of the formula:

$$—X^8—R^{10}$$

wherein $X^8$ is a direct bond or is O, and $R^{10}$ is halogeno-(1-6C)alkyl, hydroxy-(1-6C)alkyl or (1-6C)alkoxy-(1-6C)alkyl;

$X^1$ is CO; and

Z and $X^2$ have any of the values hereinbefore defined;

provided that:

when the 4-anilino group in Formula I is 4-bromo-2-fluoroanilino or 4chloro-2-fluoroanilino, $R^1$ is hydrogen or (1-3C)alkoxy, and $X^1$ is CO, then a is 0 and Z is selected from hydroxy, amino, (1-6C)alkylamino, di-[(1-6C)alkyl]amino, (1-6C)alkoxy, (1-6C)alkylsulfonyl, (1-6C)alkanesulfonylamino, N-(1-6C)alkyl-(1-6C)alkanesulfonylamino, and a group of the formula $Q^6$-$X^9$—, wherein $Q^6$-$X^9$— is as hereinbefore defined;

or a pharmaceutically acceptable salt, or a pharmaceutically acceptable ester thereof.

In this embodiment, a particular value for $X^2$ is a group selected from (3-6C)cycloalkylene (such as cyclopropylidene), —$CH_2$—, —$CH_2CH_2$—, —$CH_2CH_2CH_2$— —$CR^{12}R^{13}$—, —$(CR^{12}R^{13}CH_2)$— and —$(CH_2CR^{12}R^{13})$— wherein each of $R^{12}$ and $R^{13}$, which may be the same or different, is selected from hydrogen, (1-4C)alkyl, hydroxy-(1-4C)alkyl, and (1-3C)alkoxy-(1-4C)alkyl, provided that $R^2$ and $R^{13}$ are not both hydrogen, and wherein any $CH_2$ group within a (3-6C)cycloalkylene group in $X^2$, optionally bears on each said $CH_2$ or group one or more (1-4C)alkyl substituents or a substituent selected from hydroxy, (1-4C)alkoxy, hydroxy-(1-4C)alkyl, and (1-3C)alkoxy-(1-4C)alkyl.

In this embodiment, a particular value for Z is a group selected from hydroxy, amino, (1-6C)alkylamino, di-[(1-6C)alkyl]amino, (1-6C)alkoxy and a group of the formula:

$Q^6$-$X^9$— wherein $X^9$ is a direct bond or is selected from O and N($R^{16}$), wherein $R^{16}$ is hydrogen or (1-6C)alkyl, and $Q^6$ is (3-7C)cycloalkyl, (3-7C)cycloalkyl-(1-4C)alkyl, (3-7C)cycloalkenyl, (3-7C)cycloalkenyl-(1-4C)alkyl, heterocyclyl or heterocyclyl-(1-4C)alkyl, provided that when $X^9$ is a direct bond, $Q^6$ is heterocyclyl, and provided that when m, p and q are all 0, then Z is heterocyclyl, and wherein any heterocyclyl group in Z is selected from tetrahydrofuranyl, 1,3-dioxolanyl, tetrahydropyranyl, 1,4-dioxanyl, oxepanyl, pyrrolidinyl, morpholinyl, tetrahydro-1,4-thiazinyl, piperidinyl, homopiperidinyl, piperazinyl and homopiperazinyl, which heterocyclyl group may be carbon or nitrogen linked to the group to which it is attached, and wherein and wherein any $CH_2$ or $CH_3$ group within a Z group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein any heterocyclyl group within a Z substituent optionally bears one or more (for example 1, 2 or 3) substitutents which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

—$X^{10}$—$R^{18}$ wherein $X^{10}$ is a direct bond or is selected from O, CO, $SO_2$ and N($R^{19}$), wherein $R^{19}$ is hydrogen or (1-4C)alkyl, and $R^{18}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl.

Another particular value for Z in this embodiment is a group selected from hydroxy, amino, (1-6C)alkylamino, hydroxy-(2-6C)alkylamino, (1-4C)alkoxy-(2-6C)alkylamino, di-[(1-6C)alkyl]amino, N-[hydroxy-(2-6C)alkyl]-N-(1-6C)alkylamino, N-[(1-4C)alkoxy-(2-6C)alkyl]-N-(1-6C)alkylamino, di-[hydroxy-(2-6C)alkyl]-amino, di-[(1-4C)alkoxy-(2-6C)alkyl]amino, N-[(1-4C)alkoxy-(2-6C)alkyl]-N-[hydroxy-(2-6C)alkyl]-amino, (1-6C)alkoxy, hydroxy-(2-6C)alkoxy, (1-4C)alkoxy-(2-6C)alkoxy, azetidin-1-yl, pyrrolidin-1-yl, piperidino, piperazin-1-yl, morpholino, homopiperidin-1-yl homopiperazin-1-yl, tetrahydrofuran-2-yl, tetrahydrofuran-3-yl, 1,3-dioxolanyl, tetrahydropyranyl and 1,4-dioxanyl, and provided that when m, p and q are all 0, then Z is one of the heterocyclyl groups mentioned above, and wherein any heterocyclyl group in Z optionally bears 1 or 2 substituents, which may be the same or different, selected from fluoro, chloro, hydroxy, (1-4C)alkyl and (1-4C)alkoxy.

Another particular value for Z in this embodiment is a group selected from hydroxy, (1-4C)alkoxy, hydroxy-(2-4C)alkoxy and (1-4C)alkoxy-(2-4C)alkoxy more particularly Z is hydroxy or(1-4C)alkoxy.

In this embodiment a particular value for each $R^2$, which may be the same or different, is a group selected from fluoro, chloro or bromo and (2-4C)alkynyl;

In this embodiment a particular 4-anilino group in Formula I is selected from 3-chloro-4-fluoroanilino, 3-bromo-2-fluoroanilino, 3-chloro-2-fluoroanilino, 2-fluoro-5-chloroanilino, 3-bromoanilino and 3-ethynylanilino. Still more particularly the anilino group is 3-chloro-2-fluoroanilino or 3-bromo-2-fluoroanilino.

Another particular embodiment of the present invention is a quinazoline derivative of the Formula I wherein:

$R^1$ is selected from (1-4C)alkoxy, hydroxy-(2-4C)alkoxy, (1-3C)alkoxy-(2-4C)alkoxy or from a group of the formula:

$Q^2$-$X^3$— wherein $X^3$ is O, and $Q^2$ is azetidin-1-yl-(2-4C)alkyl, pyrrolidin-1-yl-(2-4C)alkyl, piperidino-(2-4C)alkyl, piperazino-(2-4C)alkyl or morpholino-(2-4C)alkyl, and wherein any heterocyclyl group within a substituent on $R^1$ optionally bears 1, 2 or 3 substituents, which may be the same or different, selected from halogeno, hydroxy, amino, (1-4C)alkyl, (1-4C)alkoxy, (1-4C)alkylsulfonyl, (1-4C)alkylamino, di-[(1-4C)alkyl]amino, and (2-4C)alkanoyl, and wherein any heterocyclyl group within a substituent on $R^1$ optionally bears 1 oxo substituent;

b is 1, 2 or 3;

each $R^2$, which may be the same or different, is selected from fluoro, chloro, bromo and (2-4C)alkynyl;

$Q^1$ is piperidin-4-yl;

a is 0 or 1 (preferably 0);

each W, which may be the same or different is selected from halogeno (particularly fluoro), hydroxy, (1-3C)alkyl and (1-3C)alkoxy;

$X^1$ is CO;

$X^2$ is selected from a group of the formula —$CH_2$—, —$CH_2CH_2$—, —$(CHR^{12a})$—, —$(CHR^{12a}CH_2)$—, —$C(R^{12a})_2CH_2)$—, —$(CH_2C(R^{12a})_2)$— and —$(CH_2CHR^{12b})$—, wherein each $R^{12a}$, which may be the same or different, is selected from (1-4C)alkyl, hydroxy-(1-4C)alkyl, (1-3C)alkoxy-(1-4C)alkyl, amino-(1-4C)alkyl, (1-4C)alkylamino-(1-4C)alkyl and di-[(1-4C)alkyl]-amino-(1-4C)alkyl (particularly $R^{12a}$ is (1-4C)alkyl), and wherein $R^{12b}$ is selected from hydroxy, amino, (1-4C)alkyl, (1-4C)alkoxy, (1-4C)alkylamino, di-[(1-4C)alkyl]-amino, hydroxy-(1-4C)alkyl, (1-3C)alkoxy-(1-4C)alkyl, amino-(1-4C)alkyl, (1-4C)alkylamino-(1-4C)alkyl and di-[(1-4C)alkyl]-amino-(1-4C)alkyl (particularly $R^{12b}$ selected from amino, (1-4C)alkylamino and di-[(1-4C)alkyl]-amino);

Z is selected from hydroxy, (1-4C)alkoxy, hydroxy-(2-4C)alkoxy and (1-4C)alkoxy-(2-4C)alkoxy, or Z-$X^2$ is selected from tetrahydrofuranyl, tetrahydropyranyl, azetidinyl, pyrrolidinyl, piperidinyl and morpholinyl, wherein Z-$X^2$ is linked to $X^1$ by a ring carbon atom, and wherein any heterocyclyl group within Z optionally bears one or two substituents, which may be the same or different selected from fluoro, chloro, hydroxy, (1-4C)alkyl, (1-4C)alkoxy and (2-4C)alkanoyl;

provided that:

when the 4-anilino group in Formula I is 4-bromo-2-fluoroanilino or 4-chloro-2-fluoroanilino and $R^1$ is (1-3C)alkoxy, then a is 0;

or a pharmaceutically acceptable salt, or a pharmaceutically acceptable ester thereof.

In this embodiment a particular value for Z is a group selected from hydroxy, and (1-4C)alkoxy (for example Z is hydroxy, methoxy or ethoxy).

In this embodiment a particular 4-anilino group in Formula I is selected from 3-chloro-4-fluoroanilino, 3-bromo-2-fluoroanilino, 3-chloro-2-fluoroanilino, 2-fluoro-5-chloroanilino, 3-bromoanilino and 3-ethynylanilino. Still more particularly the anilino group is 3-chloro-2-fluoroanilino or 3-bromo-2-fluoroanilino.

Another particular embodiment of the present invention is a quinazoline derivative of the Formula I wherein:

$R^1$ is selected from (1-4C)alkoxy, hydroxy-(2-4C)alkoxy, (1-3C)alkoxy-(2-4C)alkoxy or from a group of the formula:

$Q^2-X^3$— wherein $X^3$ is O, and $Q^2$ is azetidin-1-yl-(2-4C)alkyl, pyrrolidin-1-yl-(2-4C)alkyl, piperidino-(2-4C)alkyl, piperazino-(2-4C)alkyl or morpholino-(2-4C)alkyl, and wherein any heterocyclyl group within a substituent on $R^1$ optionally bears 1, 2 or 3 substituents, which may be the same or different, selected from halogeno, hydroxy, amino, (1-4C)alkyl, (1-4C)alkoxy, (1-4C)alkylsulfonyl, (1-4C)alkylamino, di-[(1-4C)alkyl]amino, and (2-4C)alkanoyl, and wherein any heterocyclyl group within a substituent on $R^1$ optionally bears 1 oxo substituent (particularly $R^1$ is selected from (1-4C)alkoxy, hydroxy-(2-4C)alkoxy and (1-3C)alkoxy-(2-4C)alkoxy, more particularly $R^1$ is (1-4C)alkoxy;

b is 1, 2 or 3 (particularly b is 1, more particularly b is 2);

each $R^2$, which may be the same or different, is selected from fluoro, chloro, bromo and (2-4C)alkynyl;

$Q^1$ is piperidin-4-yl;

a is 0 or 1 (preferably 0);

each W, which may be the same or different is selected from halogeno (particularly fluoro), hydroxy, (1-3C)alkyl and (1-3C)alkoxy;

$X^1$ is CO;

$X^2$ is a group of the formula —$(CR^{12}R^{13})_q$—$(CR^{12aa}R^{13aa})$—, q is 1, 2 or 3 (particularly 1 or 2, more particularly 1), each of $R^{12}$, $R^{13}$ and $R^{13aa}$, which may be the same or different, is selected from hydrogen and (1-6C)alkyl, $R^{12aa}$ is selected from amino, (1-4C)alkylamino and di-[(1-4C)alkyl]amino;

Z is selected from hydroxy, (1-4C)alkoxy, hydroxy-(2-4C)alkoxy and (1-4C)alkoxy-(2-4C)alkoxy, or Z-$X^2$ is Z is selected from tetrahydrofuranyl, tetrahydropyranyl, azetidinyl, pyrrolidinyl, piperidinyl and morpholinyl, wherein Z-$X^2$ is linked to $X^1$ by a ring carbon atom, and wherein any heterocyclyl group within Z optionally bears one or two substituents, which may be the same or different selected from fluoro, chloro, hydroxy, (1-4C)alkyl, (1-4C)alkoxy and (2-4C)alkanoyl;

provided that:

when the 4-anilino group in Formula I is 4-bromo-2-fluoroanilino or 4-chloro-2-fluoroanilino and $R^1$ is (1-3C)alkoxy, then a is 0;

or a pharmaceutically acceptable salt, or a pharmaceutically acceptable ester thereof.

In this embodiment a particular value for Z is a group selected from hydroxy, and (1-4C)alkoxy (for example Z is hydroxy, methoxy or ethoxy).

In this embodiment a particular 4-anilino group in Formula I is selected from 3-chloro-4-fluoroanilino, 3-bromo-2-fluoroanilino, 3-chloro-2-fluoroanilino 3-bromoanilino and 3-ethynylanilino. More particularly in this embodiment the 4-anilino group in Formula I is selected from 3-chloro-4-fluoroanilino, 3-bromo-2-fluoroanilino, 3-chloro-2-fluoroanilino and 3-bromoanilino. Still more particularly the anilino group is 3-chloro-2-fluoroanilino or 3-bromo-2-fluoroanilino. Preferably the anilino group is 3-chloro-2-fluoroanilino.

Another particular embodiment of the present invention is a quinazoline derivative of the Formula I wherein:

$R^1$ is selected from (1-4C)alkoxy, hydroxy-(2-4C)alkoxy, (1-3C)alkoxy-(2-4C)alkoxy or from a group of the formula:

$Q^2-X^3$— wherein $X^3$ is O, and $Q^2$ is azetidin-1-yl-(2-4C)alkyl, pyrrolidin-1-yl-(2-4C)alkyl, piperidino-(2-4C)alkyl, piperazino-(2-4C)alkyl or morpholino-(2-4C)alkyl, and wherein any heterocyclyl group within a substituent on $R^1$ optionally bears 1, 2 or 3 substituents, which may be the same or different, selected from halogeno, hydroxy, amino, (1-4C)alkyl, (1-4C)alkoxy, (1-4C)alkylamino and di-[(1-4C)alkyl]amino (particularly $R^1$ is selected from (1-4C)alkoxy, hydroxy-(2-4C)alkoxy and (1-3C)alkoxy-(2-4C)alkoxy, more particularly $R^1$ is (1-4C)alkoxy, for example methoxy, ethoxy, isopropyloxy, still more particularly $R^1$ is methoxy);

the 4-anilino group in Formula I is selected from 3-chloro4-fluoroanilino, 3-bromo-2-fluoroanilino, 3-chloro-2-fluoroanilino, 2-fluoro-5-chloroanilino, 3-bromoanilino and 3-ethynylanilino;

b is 1 or 2;

each $R^2$, which may be the same or different, is selected from fluoro, chloro, bromo and ethynyl;

$Q^1$ is piperidin-4-yl;

a is 0 or 1 (preferably 0);

each W, which may be the same or different is selected from halogeno (particularly fluoro), hydroxy, (1-3C)alkyl and (1-3C)alkoxy;

$X^1$ is CO;

$X^2$ is selected from a group of the formula —$(CHR^{12a})$—, —$(CHR^{12a}CH_2)$—, —$(C(R^{12a})_2CH_2)$—, —$(CH_2C(R^{12a})_2)$— and —$(CH_2CHR^{12b})$—, wherein each $R^{12a}$, which may be the same or different, is (1-4C)alkyl (particularly (1-3C)alkyl), and wherein $R^{12b}$ is selected from amino, (1-4C)alkylamino and di-[(1-4C)alkyl]-amino (particularly $R^{12b}$ is selected from (1-4C)alkylamino and di-[(1-4C)alkyl]-amino, more particularly di-[(1-3C)alkyl]-amino);

Z is selected from hydroxy, (1-4C)alkoxy, hydroxy-(2-4C)alkoxy and (1-4C)alkoxy-(2-4C)alkoxy, or Z-$X^2$ is selected from tetrahydrofuranyl, tetrahydropyranyl, azetidinyl, pyrrolidinyl, piperidinyl and morpholinyl, which is linked to $X^1$ by a ring carbon atom, and wherein any heterocyclyl group within Z optionally bears one or two substituents, which may be the same or different selected from fluoro, chloro, hydroxy, (1-4C)alkyl, (1-4C)alkoxy and (2-4C)alkanoyl;

or a pharmaceutically acceptable salt, or a pharmaceutically acceptable ester thereof.

In this embodiment a particular value for Z is a group selected from hydroxy, and (1-4C)alkoxy (for example Z is hydroxy, methoxy or ethoxy).

In this embodiment a particular 4-anilino group in Formula I is selected from 3-bromo-2-fluoroanilino, 3-chloro-2-fluoroanilino, 3-bromoanilino and 3-ethynylanilino. Still more particularly the anilino group is 3-chloro-2-fluoroanilino or 3-bromo-2-fluoroanilino.

Another particular embodiment of the present invention is a quinazoline derivative of the Formula I wherein:

$R^1$ is selected from (1-4C)alkoxy, hydroxy-(2-4C)alkoxy, (1-3C)alkoxy-(2-4C)alkoxy or from a group of the formula:

$Q^2$-$X^3$— wherein $X^3$ is O, and $Q^2$ is azetidin-1-yl-(2-4C)alkyl, pyrrolidin-1-yl-(2-4C)alkyl, piperidino-(2-4C)alkyl, piperazino-(2-4C)alkyl or morpholino-(2-4C)alkyl, and wherein any heterocyclyl group within a substituent on $R^1$ optionally bears 1, 2 or 3 substituents, which may be the same or different, selected from halogeno, hydroxy, amino, (1-4C)alkyl, (1-4C)alkoxy, (1-4C)alkylamino and di-[(1-4C)alkyl]amino (particularly $R^1$ is selected from (1-4C)alkoxy, hydroxy-(2-4C)alkoxy and (1-3C)alkoxy-(2-4C)alkoxy, more particularly $R^1$ is (1-4C)alkoxy, for example methoxy, ethoxy, isopropyloxy, still more particularly $R^1$ is methoxy);

the 4-anilino group in Formula I is selected from 3-chloro-4-fluoroanilino, 3-bromo-2-fluoroanilino, 3-chloro-2-fluoroanilino, 2-fluoro-5-chloroanilino, 3-bromoanilino and 3-ethynylanilino;

Z is hydroxy or (1-4C)alkoxy, (particularly Z is hydroxy, methoxy or ethoxy, more particularly Z is hydroxy or methoxy, especially Z is hydroxy);

$Q^1$ is piperidin-4-yl;

a is 0 or 1 (preferably 0);

each W, which may be the same or different is selected from hydroxy, (1-3C)alkyl and (1-3C)alkoxy;

$X^1$ is CO;

$X^2$ is selected from a group of the formula —$(CHR^{12a})$— and —$(CH_2CHR^{12b})$—, wherein $R^{12a}$ is (1-4C)alkyl (particularly (1-3C)alkyl, more particularly methyl), and wherein $R^{12b}$ is selected from amino, (1-4C)alkylamino and di-[(1-4C)alkyl]-amino (particularly $R^{12b}$ is selected from (1-3C)alkylamino and di-[(1-3C)alkyl]-amino, more particularly di-[(1-3C)alkyl]-amino, still more particularly $R^{12b}$ is methylamino and especially dimethylamino);

or a pharmaceutically acceptable salt, or a pharmaceutically acceptable ester thereof.

In this embodiment a particular 4-anilino group in Formula I is selected from 3-bromo-2-fluoroanilino, 3-chloro-2-fluoroanilino, 3-bromoanilino and 3-ethynylanilino. Still more particularly the anilino group is 3-chloro-2-fluoroanilino or 3-bromo-2-fluoroanilino.

Another particular embodiment of the present invention is a quinazoline derivative of the Formula I wherein:

$R^1$ is (1-4C)alkoxy (for example methoxy, ethoxy, isopropyloxy, particularly methoxy);

the 4-anilino group in Formula I is selected from 3-chloro-4-fluoroanilino, 3-bromo-2-fluoroanilino, 3-chloro-2-fluoroanilino, 2-fluoro-5-chloroanilino, 3-bromoanilino and 3-ethynylanilino;

$Q^1$ is piperidin-4-yl;

a is 0 or 1 (preferably 0);

each W, which may be the same or different is selected from hydroxy, (1-3C)alkyl and (1-3C)alkoxy;

$X^1$ is CO;

Z-$X^2$ is selected from tetrahydrofuranyl, tetrahydropyranyl, azetidinyl, pyrrolidinyl, piperidinyl and morpholinyl (particularly Z-$X^2$ is tetrahydrofuranyl or pyrrolidinyl), wherein Z-$X^2$ is linked to $X^1$ by a ring carbon atom, and wherein any heterocyclyl group within Z optionally bears one or two substituents, which may be the same or different selected from fluoro, chloro, hydroxy, methyl, methoxy and acetyl;

or a pharmaceutically acceptable salt, or a pharmaceutically acceptable ester thereof.

In this embodiment a particular 4-anilino group in Formula I is selected from 3-bromo-2-fluoroanilino, 3-chloro-2-fluoroanilino, 3-bromoanilino and 3-ethynylanilino, more particularly the anilino group is selected from 3-bromo-2-fluoroanilino and 3-chloro-2-fluoroanilino.

Another embodiment of the compounds of Formula I is a quinazoline derivative of the Formula Ia:

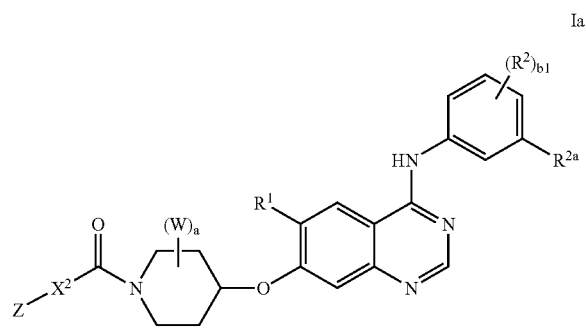

Ia wherein:

$R^1$ is selected from hydrogen, (1-6C)alkoxy, cyclopropyl-(1-4C)alkoxy, cyclobutyl-(1-4C)alkoxy, cyclopentyl-(1-4C)alkoxy, cyclohexyl-(1-6C)alkoxy, tetrahydrofuranyl-(1-4C)alkoxy and tetrahydropyranyl-(1-4C)alkoxy, and wherein any $CH_2$ or $CH_3$ group within a $R^1$ substituent optionally bears on each said $CH_2$ or $CH_3$ group one or more halogeno substituents, or a substituent selected from hydroxy and (1-4C)alkoxy;

$b_1$ is 0, 1 or 2;

each $R^2$, which may be the same or different, is selected from halogeno (particularly fluoro, chloro or bromo), cyano, hydroxy, trifluoromethyl, (1-4C)alkyl, (2-4C)alkenyl, (2-4C)alkynyl and (1-4C)alkoxy (particularly $R^2$ is selected from fluoro, chloro, bromo or ethynyl, more particularly $R^2$ is selected from fluoro, chloro and bromo);

$R^{2a}$ is halogeno (particularly fluoro, chloro or bromo, more particularly fluoro or chloro, still more particularly chloro or bromo, and especially $R^{2a}$ is chloro);

a is 0, 1 or 2;

each W, which may be the same or different, is selected from halogeno (particularly fluoro), hydroxy, (1-4C)alkyl and (1-4C)alkoxy;

$X^2$ is a group of the formula:

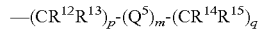

wherein m is 0 or 1, p is 0, 1, 2, 3 or 4 and q is 0, 1, 2, 3 or 4, each of $R^{12}$, $R^{13}$, $R^{14}$ and $R^{15}$, which may be the same or different, is selected from hydrogen, (1-6C)alkyl, amino, (1-6C)alkylamino and di-[(1-6C)alkyl]amino, and $Q^5$ is selected from (3-7C)cycloalkylene and (3-7C)cycloalkenylene, and wherein any $CH_2$ or $CH_3$ group within an $X^2$ group, optionally bears on each said $CH_2$ or $CH_3$ group one or more halogeno or (1-6C)alkyl substituents or a substituent selected from hydroxy, cyano, amino, (1-6C)alkoxy, (1-6C)alkylamino and di-[(1-6C)alkyl]amino;

Z is selected from hydroxy, amino, (1-6C)alkylamino, di-[(1-6C)alkyl]amino, (1-6C)alkoxy, (1-6C)alkylsulfonyl, (1-6C)alkanesulfonylamino, N-(1-6C)alkyl-(1-6C)alkanesulfonylamino, and a group of the formula:

wherein $X^9$ is a direct bond or is selected from O, N($R^{16}$), $SO_2$ and $SO_2N(R^{16})$, wherein $R^{16}$ is hydrogen or (1-6C)alkyl, and $Q^6$ is (3-7C)cycloalkyl, (3-7C)cycloalkyl-(1-4C)alkyl, (3-7C)cycloalkenyl, (3-7C)cycloalkenyl-(1-4C)alkyl, heterocyclyl or heterocyclyl-(1-4C)alkyl, provided that when $X^9$ is a direct bond, $Q^6$ is heterocyclyl, and provided that when m, p and q are all 0, then Z is heterocyclyl, and wherein adjacent carbon atoms in any (2-6C)alkylene chain within a Z substituent are optionally separated by the insertion into the chain of a group selected from O, S, SO, $SO_2$, N($R^{17}$), CO, —C═C— and —C≡C— wherein $R^{17}$ is hydrogen or (1-6C)alkyl, and wherein and wherein any $CH_2$ or $CH_3$ group within any Z group, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein any heterocyclyl group within a Z substituent optionally bears one or more (for example 1, 2 or 3) substitutents which may be the same or different, selected from halogeno, trifluoromethyl, cyano, nitro, hydroxy, amino, formyl, mercapto, (1-6C)alkyl, (2-6C)alkenyl, (2-6C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, (2-6C)alkanoyl, (2-6C)alkanoyloxy and from a group of the formula:

wherein $X^{10}$ is a direct bond or is selected from O, CO, $SO_2$ and N($R^{19}$), wherein $R^{19}$ is hydrogen or (1-4C)alkyl, and $R^{18}$ is halogeno-(1-4C)alkyl, hydroxy-(1-4C)alkyl, (1-4C)alkoxy-(1-4C)alkyl, cyano-(1-4C)alkyl, amino-(1-4C)alkyl, N-(1-4C)alkylamino-(1-4C)alkyl and N,N-di-[(1-4C)alkyl]amino-(1-4C)alkyl;

provided that:

when the 4-anilino group in Formula I is 4-bromo-2-fluoroanilino or 4-chloro-2-fluoroanilino and $R^1$ is (1-3C)alkoxy, then a is 0;

or a pharmaceutically acceptable salt, or a pharmaceutically acceptable ester thereof.

Another embodiment of the present invention is a quinazoline derivative of the Formula Ia as hereinbefore defined, wherein $X^2$ is a group selected from (3-6C)cycloalkylene (such as cyclopropylidene), —$CH_2$—, —$CH_2CH_2$—, —$CH_2CH_2CH_2$— —$(CR^{12}R^{13})$—, —$CR^{12}R^{13}CH_2$— and —$(CH_2CR^{12}R^{13})$— wherein each of $R^{12}$ and $R^{13}$, which may be the same or different, is selected from hydrogen, (1-4C)alkyl, hydroxy-(1-4C)alkyl, and (1-3C)alkoxy-(1-4C)alkyl, provided that $R^{12}$ and $R^{13}$ are not both hydrogen, and wherein any $CH_2$ group within a (3-6C)cycloalkylene group in $X^2$, optionally bears on each said $CH_2$ or group one or more (1-4C)alkyl substituents or a substituent selected from hydroxy, (1-4C)alkoxy, hydroxy-(1-4C)alkyl, and (1-3C)alkoxy-(1-4C)alkyl.

Another embodiment of the present invention is a quinazoline derivative of the Formula 1a as hereinbefore defined, wherein $X^2$ is a group selected from cyclopropylidene, —$CH_2$—, —$CH_2CH_2$—, —$(CR^{12}R^{13})$—, —$(CR^{12}R^{13}CH_2)$— and —$(CH_2CR^{12}R^{13})$—, wherein each of $R^{12}$ and $R^{13}$, which may be the same or different, is selected from hydrogen and (1-4C)alkyl.

Another embodiment of the present invention is a quinazoline derivative of the Formula 1a as hereinbefore defined, wherein Z is selected from hydroxy, amino, (1-6C)alkylamino, hydroxy-(2-6C)alkylamino, (1-4C)alkoxy-(2-6C)alkylamino, di-[(1-6C)alkyl]amino, N-[hydroxy-(2-6C)alkyl]-N-(1-6C)alkylamino, N-[(1-4C)alkoxy-(2-6C)alkyl]-N-(1-6C)alkylamino, di-[hydroxy-(2-6C)alkyl]-amino, di-[(1-4C)alkoxy-(2-6C)alkyl]amino, N-[(1-4C)alkoxy-(2-6C)alkyl]-N-[hydroxy-(2-6C)alkyl]-amino, (1-6C)alkoxy, hydroxy-(2-6C)alkoxy, (1-4C)alkoxy-(2-6C)alkoxy, azetidin-1-yl, pyrrolidin-1-yl, piperidino, piperazin-1-yl, morpholino, homopiperidin-1-yl homopiperazin-1-yl, tetrahydrofuran-2-yl, tetrahydrofuran-3-yl, 1,3-dioxolanyl, tetrahydropyranyl and 1,4-dioxanyl; or the group Z-$X^2$ is selected from is selected from tetrahydrofuranyl, 1,3-dioxolanyl, tetrahydropyranyl, 1,4-dioxanyl, oxepanyl, pyrrolidinyl, morpholinyl, piperidinyl, homopiperidinyl, piperazinyl and homopiperazinyl, which heterocyclyl represented by Z-$X^2$ is linked to the carbonyl group in Formula Ia, by a ring carbon, and wherein any heterocyclyl group within Z-$X^2$ optionally bears 1 or 2 substituents, which may be the same or different, selected from fluoro, chloro, hydroxy, (1-4C)alkyl, (1-4C)alkoxy and (2-4C)alkanoyl.

More particularly, in Formula 1a, Z is selected from hydroxy, methoxy, ethoxy, 2-hydroxyethoxy, 2-methoxyethoxy, amino, methylamino, ethylamino, N-(2-hydroxyethyl)amino, N-(2-methoxyethyl)amino, dimethylamino, N-methyl-N-ethylamino, di-ethylamino, N-(2-hydroxyethyl)-N-methylamino, N-(2-hydroxyethyl)-N-ethylamino, N,N-di-(2-hydroxyethyl)amino, N-(2-methoxyethyl)-N-methylamino, N-(2-methoxyethyl)-N-ethylamino, pyrrolidin-1-yl, piperidino, piperazin-1-yl, morpholino, tetrahydrofuranyl and tetrahydropyranyl; or the group $Z-X^2$ is selected from is selected from tetrahydrofuranyl and tetrahydropyranyl, and wherein any heterocyclyl group within Z optionally bears 1 or 2 substituents, which may be the same or different, selected from fluoro, chloro, hydroxy, (1-4C)alkyl and (1-4C)alkoxy. More particularly Z is selected from hydroxy, (1-4C)alkoxy, hydroxy-(2-4C)alkoxy and (1-4C)alkoxy-(2-4C)alkoxy, still more particularly Z is selected from hydroxy and (1-4C)alkoxy (for example Z is hydroxy or methoxy). Preferably Z is hydroxy.

Another embodiment of the present invention is a quinazoline derivative of the Formula 1a as hereinbefore defined, wherein:

$R^{2a}$ is bromo or chloro (particularly chloro); and b is 0 or 1 and $R^2$ is at the ortho (2-) position and is halogeno (particularly $R^2$ is fluoro); or b is 0 or 1 and $R^2$ is at the para (4-) position and is halogeno (particularly $R^2$ is fluoro) and wherein $R^1$, W, a, $X^2$ and Z have any of the meanings defined hereinabove in relation to the quinazoline derivative of Formula 1a.

Another particular embodiment of the invention is a quinazoline derivative of the Formula 1a as hereinbefore defined wherein the anilino group at the 4-position on the quinazoline ring is selected from 3-bromo-2-fluoroanilino, 3-bromoanilino, 3-chloro-4-fluoroanilino and 3-chloro-2-fluoroanilino. Particularly the anilino group is selected from 3-chloro-4-fluoroanilino and 3-chloro-2-fluoroanilino. More particularly the anilino group is 3-chloro-4-fluoroanilino. It is preferred that the anilino group is 3-chloro-2-fluoroanilino. Wherein in this embodiment $R^1$, W, a, $X^2$ and Z have any of the meanings defined hereinabove in relation to the quinazoline derivative of Formula 1a.

Another embodiment of the compounds of Formula I is a quinazoline derivative of the Formula Ib:

Ib wherein:

$R^1$ is selected from hydrogen, (1-6C)alkoxy, cyclopropyl-(1-4C)alkoxy, cyclobutyl-(1-4C)alkoxy, cyclopentyl-(1-4C)alkoxy, cyclohexyl-(1-6C)alkoxy, tetrahydrofuranyl-(1-4C)alkoxy and tetrahydropyranyl-(1-4C)alkoxy, and wherein any $CH_2$ or $CH_3$ group within a $R^1$ substituent optionally bears on each said $CH_2$ or $CH_3$ group one or more halogeno substituents, or a substituent selected from hydroxy and (1-4C)alkoxy;

$R^{2b}$ is bromo or chloro (particularly chloro);

a is 0, 1 or 2 (particularly a is 0);

each W, which may be the same or different, is selected from hydroxy, halogeno (particularly fluoro), (1-4C)alkyl and (1-4C)alkoxy;

$X^2$ is selected from a group of the formula —$CH_2$—, —$CH_2CH_2$—, —$CH_2CH_2CH_2$— —$(CR^{12}R^{13})$—, —$(CR^{12}R^{13}CH_2)$— and —$(CH_2CR^{12}R^{13})$— wherein each of $R^2$ and $R^{13}$, which may be the same or different, is selected from hydrogen and (1-4C)alkyl (particularly $X^2$ is $CH_2$, more particularly $X^2$ is$(CHR^{12a})$—, wherein $R^{12a}$ is (1-4C)alkyl);

Z is selected from hydroxy, amino, (1-6C)alkylamino, hydroxy-(2-6C)alkylamino, (1-4C)alkoxy-(2-6C)alkylamino, di-[(1-6C)alkyl]amino, N-[hydroxy-(2-6C)alkyl]-N-(1-6C)alkylamino, N-[(1-4C)alkoxy-(2-6C)alkyl]-N-(1-6C)alkylamino, di-[hydroxy-(2-6C)alkyl]-amino, di-[(1-4C)alkoxy-(2-6C)alkyl]amino, N-[(1-4C)alkoxy-(2-6C)alkyl]-N-[hydroxy-(2-6C)alkyl]-amino, (1-6C)alkoxy, hydroxy-(2-6C)alkoxy, (1-4C)alkoxy-(2-6C)alkoxy, azetidin-1-yl, pyrrolidin-1-yl, piperidino, piperazin-1-yl, morpholino, homopiperidin-1-yl homopiperazin-1-yl, tetrahydrofuran-2-yl, tetrahydrofuran-3-yl, 1,3-dioxolanyl, tetrahydropyranyl and 1,4-dioxanyl; or the group $Z-X^2$ is selected from is selected from tetrahydrofuranyl, 1,3-dioxolanyl, tetrahydropyranyl, 1,4-dioxanyl, oxepanyl, pyrrolidinyl, morpholinyl, piperidinyl, homopiperidinyl, piperazinyl and homopiperazinyl, which heterocyclyl represented by $Z-X^2$ is linked to the carbonyl group in Formula Ib, by a ring carbon, and wherein any heterocyclyl group within $Z-X^2$ optionally bears 1 or 2 substituents, which may be the same or different, selected from fluoro, chloro, hydroxy, (1-4C)alkyl, (1-4C)alkoxy and (2-4C)alkanoyl;

or a pharmaceutically acceptable salt, or a pharmaceutically acceptable ester thereof.

In an embodiment in Formula Ib, Z is selected from hydroxy, methoxy, ethoxy, 2-hydroxyethoxy, 2-methoxyethoxy, amino, methylamino, ethylamino, N-(2-hydroxyethyl)amino, N-(2-methoxyethyl)amino, dimethylamino, N-methyl-N-ethylamino, di-ethylamino, N-(2-hydroxyethyl)-N-methylamino, N-(2-hydroxyethyl)-N-ethylamino, N,N-di-(2-hydroxyethyl)amino, N-(2-methoxyethyl)-N-methylamino, N-(2-methoxyethyl)-N-ethylamino, pyrrolidin-1-yl, piperidino, piperazin-1-yl, morpholino, tetrahydrofuranyl and tetrahydropyranyl; or the group $Z-X^2$ is selected from is selected from tetrahydrofuranyl and tetrahydropyranyl, and wherein any heterocyclyl group within Z optionally bears 1 or 2 substituents, which may be the same or different, selected from fluoro, chloro, hydroxy, (1-4C)alkyl and (1-4C)alkoxy.

In another embodiment in formula Ib, $R^1$ is selected from hydrogen methoxy, ethoxy, propyloxy, isopropyloxy, cyclopropylmethoxy, 2-hydroxyethoxy, 2-fluoroethoxy, 2-methoxyethoxy, 2-ethoxyethoxy, 2,2-difluoroethoxy and 2,2,2-trifluoroethoxy (Particularly $R^1$ is selected from hydrogen and (1-3C)alkoxy, more particularly $R^1$ is (1-3C)alkoxy such as methoxy).

In another embodiment in Formula Ib, $R^1$ is selected from (1-4C)alkoxy, hydroxy-(2-4C)alkoxy and (1-3C)alkoxy-(2-4C)alkoxy; a is 0; Z is selected from hydroxy, (1-4C)alkoxy, hydroxy-(2-4C)alkoxy and (1-4C)alkoxy-(2-4C)alkoxy, more particularly Z is selected from hydroxy and (1-4C)alkoxy, particularly Z is hydroxy or methoxy (especially hydroxy); and $X^2$ has any of the meanings defined hereinabove in relation to the quinazoline of the Formula 1b.

Another embodiment of the compounds of Formula I is a quinazoline derivative of the Formula Ic:

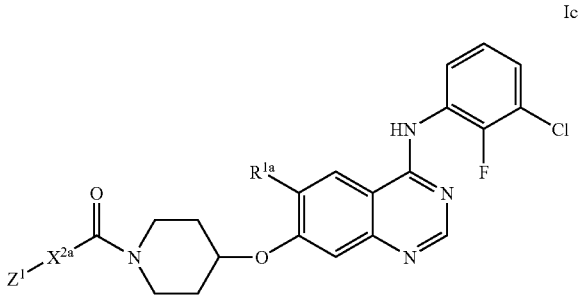

wherein:

$R^{1a}$ is selected from (1-3C)alkoxy, hydroxy-(2-3C)alkoxy and (1-3C)alkoxy-(2-3C)alkoxy (particularly $R^{1a}$ is methoxy);

$X^{2a}$ is selected from a group of the formula —(CHR$^{12a}$)— and —(CH$_2$CHR$^{12b}$)—, wherein $R^{12a}$ is (1-4C)alkyl (particularly (1-3C)alkyl, more particularly methyl), and wherein $R^{12b}$ is selected from amino, (1-4C)alkylamino and di-[(1-4C)alkyl]-amino (particularly $R^{12b}$ is selected from (1-3C)alkylamino and di-[(1-3C)alkyl]-amino, more particularly di-[(1-3C)alkyl]-amino, still more particularly $R^{12b}$ is methylamino and especially di methyl amino);

$Z^1$ is selected from hydroxy, (1-4C)alkoxy, hydroxy-(2-4C)alkoxy and (1-4C)alkoxy-(2-4C)alkoxy (particularly $Z^1$ is hydroxy or (1-4C)alkoxy, for example hydroxy or methoxy), or the group $Z^1$-$X^{2a}$ is selected from tetrahydrofuranyl, tetrahydropyranyl, pyrrolidinyl, and piperidinyl, wherein $Z^1$-$X^{2a}$ is linked to the carbonyl group by a ring carbon atom, and wherein any heterocyclyl group within $Z^1$ optionally bears one or two substituents, which may be the same or different selected from fluoro, chloro, hydroxy, (1-4C)alkyl, (1-4C)alkoxy and (2-4C)alkanoyl;

or a pharmaceutically acceptable salt, or a pharmaceutically acceptable ester thereof.

In this embodiment, preferably $Z^1$ is selected from hydroxy and (1-4C)alkoxy (particularly $Z^1$ is hydroxy or methoxy, still more particularly $Z^1$ is hydroxy).

In this embodiment, preferably $X^{2a}$ is a group of the formula —(CHR$^{12a}$)—, wherein $R^{12a}$ is (1-4C)alkyl (particularly (1-3C)alkyl, more particularly methyl), Another embodiment of the compounds of Formula I is a quinazoline derivative of the Formula Id:

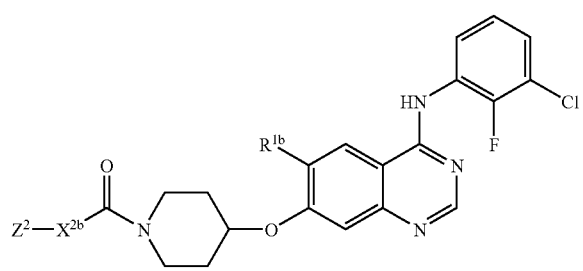

wherein:

$R^{1b}$ is (1-4C)alkoxy, and wherein any CH$_2$ or CH$_3$ group within a $R^{1b}$ substituent optionally bears on each said CH$_2$ or CH$_3$ group one or more halogeno substituents, or any CH$_2$ or CH$_3$ group within a $R^1$ which is not attached to an oxygen atom optionally bears on each said CH$_2$ or CH$_3$ group a substituent selected from hydroxy and (1-3C)alkoxy;

$X^{2b}$ is selected from a group of the formula —CH$_2$—, —CH$_2$CH$_2$—, —(CHR$^{12}$)—, —(CHR$^{12}$CH$_2$)— and —(CH$_2$CHR$^{12}$)— wherein $R^{12}$ is selected from (1-3C)alkyl, hydroxy-(1-3C)alkyl and (1-3C)alkoxy-(1-3C)alkyl; and $Z^2$ is selected from hydroxy, (1-3C)alkoxy, hydroxy-(2-3C)alkoxy, (1-3C)alkoxy-(2-3C)alkoxy, tetrahydrofuran-2-yl, tetrahydrofuran-3-yl, 1,3-dioxolanyl, tetrahydropyranyl and 1,4-dioxanyl;

and wherein any heterocyclyl group within $Z^2$-$X^{2b}$ optionally bears 1 or 2 substituents, which may be the same or different, selected from fluoro, chloro, hydroxy, (1-3C)alkyl, (1-3C)alkoxy and (2-3C)alkanoyl;

or a pharmaceutically acceptable salt thereof, or a pharmaceutically acceptable ester thereof.

In an embodiment in formula Id, $R^{1b}$ is selected from methoxy, ethoxy, 2-hydroxyethoxy, 2-fluoroethoxy, 2-methoxyethoxy, 2-ethoxyethoxy, 2,2-difluoroethoxy and 2,2,2-trifluoroethoxy (Particularly $R^{1b}$ is (1-3C)alkoxy such as methoxy).

In another embodiment in formula Id, $X^{2b}$ is selected from a group of the formula —CH$_2$—, —CH$_2$CH$_2$— and —(CHR$^{12}$)—, wherein $R^{12}$ is selected from (1-3C)alkyl, hydroxy-(1-3C)alkyl and (1-3C)alkoxy-(1-3C)alkyl (for example $R^{12}$ is methyl).

In another embodiment in formula Id, $X^{2b}$ is selected from a group of the formula —CH$_2$— and —(CHR$^{12}$)—, wherein $R^2$ is (1-3C)alkyl (for example methyl). For example $X^{2b}$ is selected from —CH$_2$— and —CH(CH$_3$)—, particularly $X^{2b}$ is —CH(CH$_3$)—.

In another embodiment in formula Id, $Z^2$ is selected from hydroxy and (1-3C)alkoxy (especially hydroxy).

In another embodiment in formula Id, the group $Z^2$-$X^{2b}$— is selected from hydroxymethyl, methoxymethyl, (S)-1-hydroxyethyl, (R)-1-hydroxyethyl, (S)-1-methoxyethyl, (R)-1-methoxyethyl. Particularly the group $Z^2$-$X^{2b}$— is 1-hydroxyethyl, more particularly (S)-1-hydroxyethyl or (R)-1-hydroxyethyl.

In another embodiment in formula Id $R^{1b}$ is (1-3C)alkoxy such as methoxy; and the group $Z^2$-$X^{2b}$— is selected from hydroxymethyl, methoxymethyl, (S)-1-hydroxyethyl, (R)-1-hydroxyethyl, (S)-1-methoxyethyl, (R)-1-methoxyethyl. Particularly in this embodiment $Z^2$-$X^{2b}$ is 1-hydroxyethyl, more particularly (S)-1-hydroxyethyl or (R)-1-hydroxyethyl.

A particular compound of the invention is, for example, a quinazoline derivative of the Formula I selected from:

N-(3-chloro-2-fluorophenyl)-7-({1-[(dimethylamino)acetyl]piperidin4-yl}oxy)-6-methoxyquinazolin-4-amine;

N-(3-chloro-2-fluorophenyl)-6-methoxy-7-({1-[(2-methoxyethoxy)acetyl]piperidin-4-yl}oxy)quinazolin-4-amine;

N-(3-chloro-2-fluorophenyl)-6-methoxy-7-{[1-(methoxyacetyl)piperidin-4-yl]oxy}quinazolin-4-amine;

2-[4-({4-[3-chloro-2-fluoroanilino]-6-methoxyquinazolin-7-yl}oxy)piperidin-1-yl]-2-oxoethanol;

N-(3-chloro-2-fluorophenyl)-7-{[1-(ethoxyacetyl)piperidin-4-yl]oxy}-6-methoxyquinazolin-4-amine;

N-(3-chloro-2-fluorophenyl)-6-methoxy-7-{[1-(3-methoxypropanoyl)piperidin-4-yl]oxy}quinazolin-4-amine;
3-[4-({4-[3-chloro-2-fluoroanilino]-6-methoxyquinazolin-7-yl}oxy)piperidin-1-yl]-3-oxopropan-1-ol;
(2S)-1-[4-({4-[3chloro-2-fluoroanilino]-6-methoxyquinazolin-7-yl}oxy)piperidin-1-yl]-1-oxopropan-2-ol;
(2S,3S)-1-[4-({4-[3chloro-2-fluoroanilino]-6-methoxyquinazolin-7-yl}oxy)piperidin-1-yl]-3-methyl-1-oxopentan-2-ol;
4-[4-({4-[3chloro-2-fluoroanilino]-6-methoxyquinazolin-7-yl}oxy)piperidin-1-yl]-2-methyl-4-oxobutan-2-ol;
N-(3-chloro-2-fluorophenyl)-6-methoxy-7-{[1-(tetrahydrofuran-2-ylcarbonyl)piperidin-4-yl]oxy}quinazolin-4-amine;
3-[4-({4-[3chloro-2-fluoroanilino]-6-methoxyquinazolin-7-yl}oxy)piperidin-1-yl]-2,2-dimethyl-3-oxopropan-1-ol;
(3R,5S)-1-acetyl-5-{[4-({4-[3-chloro-2-fluoroanilino]-6-methoxyquinazolin-7-yl}oxy)piperidin-1-yl]carbonyl}pyrrolidin-3-ol; and
N-(3-chloro-2-fluorophenyl)-6-methoxy-7-({1-[(4-methylpiperazin-1-yl)acetyl]piperidin-4-yl}oxy)quinazolin-4-amine;

or a pharmaceutically acceptable salt, or pharmaceutically acceptable ester thereof.

Another particular compound of the invention is, for example, a quinazoline derivative of the Formula I selected from:

N-(3-Chloro-2-fluorophenyl)-6-methoxy-7-{[1-(methoxyacetyl)piperidin-4-yl]oxy}quinazolin-4-amine;
2-[4-({4-[3-chloro-2-fluoroanilino]-6-methoxyquinazolin-7-yl}oxy)piperidin-1-yl]-2-oxoethanol;
N-(3-chloro-2-fluorophenyl)-7-{[1-(ethoxyacetyl)piperidin-4-yl]oxy}-6-methoxyquinazolin-4-amine;
(2S)-1-[4-({4-[3-chloro-2-fluoroanilino]-6-methoxyquinazolin-7-yl}oxy)piperidin-1-yl]-1-oxopropan-2-ol; and
3-[4-({4-[3-chloro-2-fluoroanilino]-6-methoxyquinazolin-7-yl}oxy)piperidin-1-yl]-2,2-dimethyl-3-oxopropan-1-ol;
(2S)-1-[4-({4-[3-chloro-2-fluoroanilino]-6-methoxyquinazolin-7-yl}oxy)piperidin-1-yl]-3,3-dimethyl-1-oxobutan-2-ol;
N-(3-chloro-2-fluorophenyl)-6-methoxy-7-{[1-(1-methyl-L-prolyl)piperidin-4-yl]oxy}quinazolin-4-amine;
N-(3-chloro-2-fluorophenyl)-6-methoxy-7-({1-[(2S)-tetrahydrofuran-2-ylcarbonyl]piperidin-4-yl}oxy)quinazolin-4-amine;
(2R)-1-[4-({4-[3-chloro-2-fluoroanilino]-6-methoxyquinazolin-7-yl}oxy)piperidin-1-yl]-1-oxopropan-2-ol;
N-(3-chloro-2-fluorophenyl)-6-methoxy-7-({1-[(2S)-2-methoxypropanoyl]piperidin-4-yl}oxy)quinazolin-4-amine;
N-(3-chloro-2-fluorophenyl)-6-methoxy-7-({1-[(2R)-2-methoxypropanoyl]piperidin-4-yl}oxy)quinazolin-4-amine;
(2R)-3-[4-({4-[3-chloro-2-fluoroanilino]-6-methoxyquinazolin-7-yl}oxy)piperidin-1-yl]-2-(dimethylamino)-3-oxopropan-1-ol;
(2S)-1-[4-({4-[(3-chloro-4-fluoroanilino]-6-methoxyquinazolin-7-yl}oxy)piperidin-1-yl]-1-oxopropan-2-ol;
(2S)-1-[4-({4-[3-bromoanilino]-6-methoxyquinazolin-7-yl}oxy)piperidin-1-yl]-1-oxopropan-2-ol;
(2S)-1-[4-({4-[3-bromo-2-fluoroanilino]-6-methoxyquinazolin-7-yl}oxy)piperidin-1-yl]-1-oxopropan-2-ol;
(2R)-1-[4-({4-[3-bromo-2-fluoroanilino]-6-methoxyquinazolin-7-yl}oxy)piperidin-1-yl]-1-oxopropan-2-ol; and (2R)-1-[4-({4-[3-bromoanilino]-6-methoxyquinazolin-7-yl}oxy)piperidin-1-yl]-1-oxopropan-2-ol;

or a pharmaceutically acceptable salt, or a pharmaceutically acceptable ester thereof.

In a particular embodiment the invention there is provided a quinazoline derivative of the Formula I described herein, or a pharmaceutically acceptable salt thereof.

A quinazoline derivative of the Formula I, or a pharmaceutically acceptable salt, or a pharmaceutically acceptable ester thereof, may be prepared by any process known to be applicable to the preparation of chemically-related compounds. Suitable processes include, for example, those illustrated in WO94/27965, WO 95/03283, WO 96/33977, WO 96/33978, WO 96/33979, WO 96/33980, WO 96/33981, WO 97/30034, WO 97/38994, WO01/66099, U.S. Pat. No. 5,252,586, EP 520 722, EP 566 226, EP 602 851 and EP 635 507. Such processes, when used to prepare a quinazoline derivative of the Formula I are provided as a further feature of the invention and are illustrated by the following representative process variants in which, unless otherwise stated, $R^1$, $R^2$, $X^1$, $X^2$, $Q^1$, W, a, b and Z have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

Process (a):

For the preparation of compounds of the Formula I wherein $X^1$ is CO, the coupling, conveniently in the presence of a suitable base, of a quinazoline of the formula II or a salt thereof:

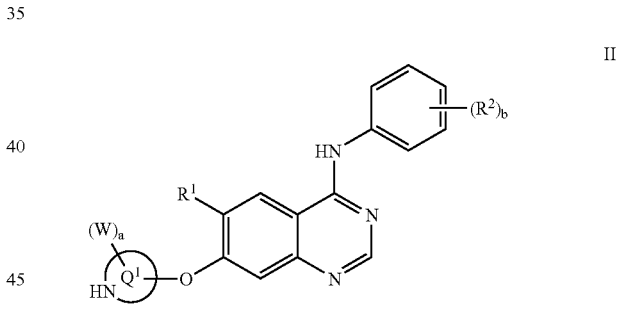

II wherein $R^1$, $R^2$, W, a, b and $Q^1$ have any of the meanings defined hereinbefore except that any functional group is protected if necessary, with an acid of the formula III, or a reactive derivative thereof:

$$Z\text{-}X^2\text{---}COOH \qquad\qquad III$$

wherein Z and $X^2$ have any of the meanings defined hereinbefore except that any functional group is protected if necessary;

or

Process (b) the reaction, conveniently in the presence of a suitable base, of a quinazoline of the formula II, or salt thereof, as hereinbefore defined in relation to Process (a), with a compound of the formula IV:

$$Z\text{-}X^2\text{---}X^1\text{-}L^1 \qquad\qquad IV$$

wherein $L^1$ is a displaceable group and Z, $X^1$ and $X^2$ have any of the meanings defined hereinbefore except that any functional group is protected if necessary;

or

Process (c) for the preparation of those quinazoline derivatives of the Formula I wherein Z is linked to $X^2$ by nitrogen, the reaction, conveniently in the presence of a suitable base, of a compound of the formula V:

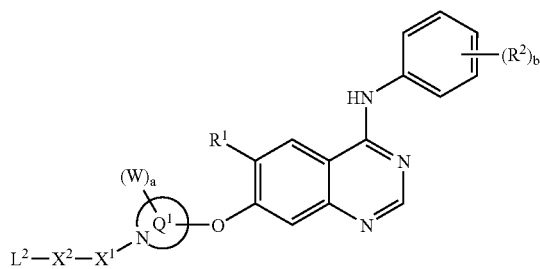

wherein $L^2$ is a displaceable group and $R^1$, $R^2$, W, $X^1$, $X^2$, a, b and $Q^1$ have any of the meanings defined hereinbefore except that any functional group is protected if necessary, with a compound of the formula ZH, wherein Z is as hereinbefore defined, except that any functional group is protected if necessary; or Process (d)

for the preparation of those quinazoline derivatives which carry a mono- or di-(1-6C)alkylamino group, the reductive amination of the corresponding quinazoline derivative of the Formula I which contains an N—H group using formaldehyde or a (2-6C)alkanolaldehyde (for example acetaldehyde or propionaldehyde); or Process (e)

for the production of those quinazoline derivatives of the Formula I wherein $R^1$ is hydroxy, the cleavage of a quinazoline derivative of the Formula I wherein $R^1$ is a (1-6C)alkoxy group; or Process (f)

for the production of those quinazoline derivatives of the Formula I wherein $R^1$ is linked to the quinazoline ring by an oxygen atom, by coupling a compound of the Formula VI:

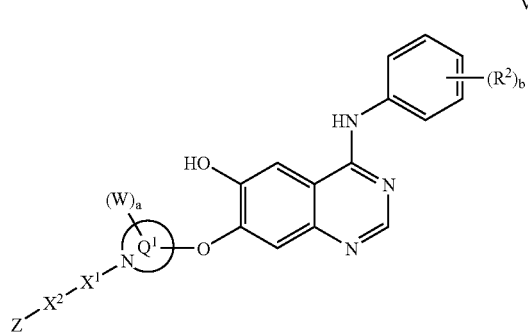

wherein $R^2$, W, $X^1$, $X^2$, Z, a, b and $Q^1$ have any of the meanings defined hereinbefore except that any functional group is protected if necessary, with a compound of the formula $R^{1'}$OH, wherein the group $R^{1'}$O is one of the oxygen linked groups as hereinbefore defined for $R^1$ (for example $R^{1'}$ is (1-6C)alkoxy or $Q^2$-O—), except that any functional group is protected if necessary;

and thereafter, if necessary (in any order):

(i) converting a quinazoline derivative of the Formula I into another quinazoline derivative of the Formula I;

(ii) removing any protecting group that is present by conventional means; and (iii) forming a pharmaceutically acceptable salt, or a pharmaceutically acceptable ester. Specific conditions for the above reactions are as follows:

Conditions for Process (a)

The coupling reaction is conveniently carried out in the presence of a suitable coupling agent, such as a carbodiimide, or a suitable peptide coupling agent, such as a uronium coupling agent, for example O-(7-azabenzotriazol-1-yl)-N,N,N', N'-tetramethyluronium hexafluoro-phosphate (HATU) or O-(1H-Benzotriazol-1-yl)-N,N,N',N'-tetramethyl uronium tetrafluoroborate (TBTU); or a carbodiimide such as dicyclohexylcarbodiimide, optionally in the presence of a catalyst such as dimethylaminopyridine or 4-pyrrolidinopyridine.

The coupling reaction is conveniently carried out in the presence of a suitable base. A suitable base is, for example, an organic amine base such as, for example, pyridine, 2,6-lutidine, collidine, 4-dimethylaminopyridine, triethylamine, di-isopropylethylamine, N-methylmorpholine or diazabicyclo[5.4.0]undec-7-ene, or, for example, an alkali or alkaline earth metal carbonate, for example sodium carbonate, potassium carbonate, cesium carbonate or calcium carbonate.

The reaction is conveniently carried out in the presence of a suitable inert solvent or diluent, for example an ester such as or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, from 0 to 120° C., conveniently at or near ambient temperature.

By the term "reactive derivative" of the acid of the formula III is meant a carboxylic acid derivative that will react with the quinazoline of formula II to give the corresponding amide. A suitable reactive derivative of a carboxylic acid of the formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, or N-hydroxybenzotriazole; or an acyl azide, for example an azide formed by the reaction of the acid and azide such as diphenylphosphoryl azide; an acyl cyanide, for example a cyanide formed by the reaction of an acid and a cyanide such as diethylphosphoryl cyanide. The reaction of such reactive derivatives of carboxylic acid with amines (such as a compound of the formula II) is well known in the art, for Example they may be reacted in the presence of a base, such as those described above, and in a suitable solvent, such as those described above. The reaction may conveniently be performed at a temperature as described above.

Preparation of Starting Materials for Process (a)

The quinazoline of the formula II may be obtained by conventional procedures, for example as illustrated in Reaction Scheme 1:

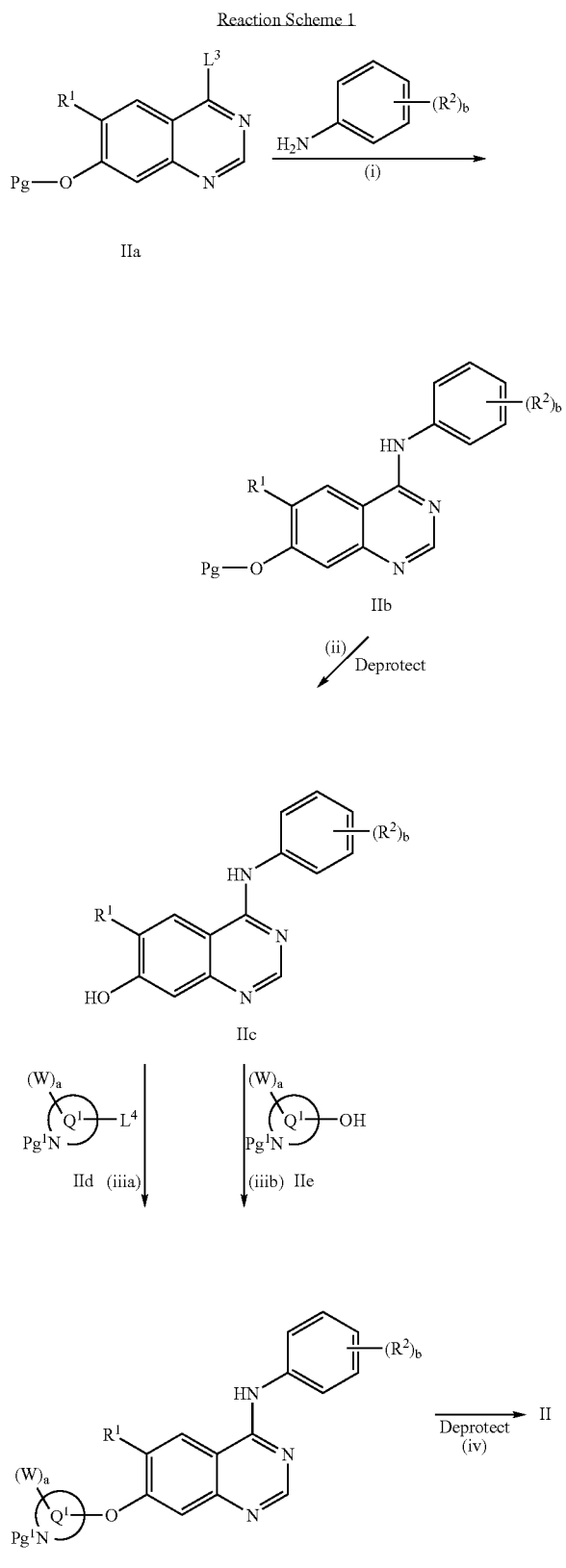

Reaction Scheme 1 wherein $R^1$, $R^2$, $Q^1$, W, a and b are as hereinbefore defined, except any functional group is protected if necessary, and whereafter any protecting group that is present is removed by conventional means, Pg is a suitable hydroxy protecting group, $Pg^1$ is a suitable amino protecting group and $L^3$ is a displaceable group.

Conditions in Reaction Scheme 1

Step(i): Suitable hydroxy protecting groups represented by Pg are well known in the art and include those mentioned herein, for example a lower alkanoyl group such as acetyl, or a benzyl group.

A suitable displaceable group $L^3$ is, for example, a halogeno (particularly chloro), alkoxy, aryloxy, mercapto, alkylthio, arylthio, alkylsulfinyl, arylsulfinyl, alkylsulfonyl, arylsulfonyl, alkylsulfonyloxy or arylsulfonyloxy group, for example a chloro, bromo, methoxy, phenoxy, pentafluorophenoxy, methylthio, methanesulfonyl, methanesulfonyloxy or toluene-4-sulfonyloxy group. A particular displaceable group $L^3$ is chloro.

The reaction is conveniently carried out in the presence of an acid. Suitable acids include, for example hydrogen chloride gas (conveniently dissolved in a suitable solvent such as diethyl ether or dioxane) or hydrochloric acid.

Alternatively the quinazoline derivative of the formula IIa, wherein $L^3$ is halogeno (for example chloro), may be reacted with the aniline in the absence of an acid or a base. In this reaction displacement of the halogeno leaving group $L^3$ results in the formation of the acid $HL^3$ in-situ and the autocatalysis of the reaction.

Alternatively, the reaction of the quinazoline of formula IIa with the aniline may be carried out in the presence of a suitable base. A suitable base is, for example, an organic amine base such as, for example, pyridine, 2,6-lutidine, collidine, 4-dimethylaminopyridine, triethylamine, di-isopropylethylamine, N-methylmorpholine or diazabicyclo[5.4.0]undec-7-ene, or, an alkali or alkaline earth metal carbonate, for example sodium carbonate, potassium carbonate, cesium carbonate or calcium carbonate, or an alkali metal hydride, for example sodium hydride, an alkali metal fluoride such as cesium fluoride, or an alkali metal disilazide such as sodium hexamethyldisilazide.

The above reactions are conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one, dimethylsulfoxide or acetonitrile. The above reactions are conveniently carried out at a temperature in the range, for example, 0 to 250° C., conveniently in the range 40 to 80° C. or, preferably, at or near the reflux temperature of the solvent when used.

The aniline and the compound of the formula IIa are commercially available or can be prepared using conventional methods.

Step (ii):

Deprotection using well-known methods. For example when Pg is a benzyl group it may be removed by treating the compound of formula IIb with a suitable acid such as trifluoroacetic acid. Alternatively a benzyl protecting group may be removed by metal-catalysed hydrogenation, for example by hydrogenation in the presence of a palladium on carbon catalyst. Similarly, when Pg is a lower alkanoyl group such as acetyl it may be removed by hydrolysis under basic conditions, for example using ammonia, conveniently as a methanolic ammonia solution.

Step (iiia):

Suitable amino protecting groups $Pg_2$ are well known, for example tert-butoxycarbonyl (BOC) groups.

$L^4$ is a suitable displaceable group, for example as described above in relation to $L^2$, such as halogeno (particularly chloro or bromo), or an alkylsulfonyloxy (particularly methanesulfonyloxy) or arylsulfonyloxy (particularly toluene-4-sulfonyloxy or 4-nitrophenylsulfonyloxy) group.

The reaction of the compound of formula IIc with the compound of formula IId is conveniently carried out in the presence of a suitable base. Suitable bases include those described above in relation to step (i), such as cesium fluoride or potassium carbonate. The reaction is conveniently carried out in the presence of a suitable inert solvent, for example, a dipolar aprotic solvent such as N,N-dimethylformamide, N,N-dimethylacetamide, N-methylpyrrolidin-2-one, dimethylsulfoxide or acetonitrile. The above reaction is conveniently carried out at a temperature in the range, for example, 0 to 250° C., conveniently in the range 40 to 80° C. or, preferably, at or near the reflux temperature of the solvent when used.

Step (iiib):

An alternative to step (iiia) is the coupling of the compound of formula IIc with the alcohol of the formula IIe using the Mitsunobu coupling reaction. Suitable Mitsunobu conditions are well known and include, for example, reaction in the presence of a suitable tertiary phosphine and a di-alkylazodicarboxylate in an organic solvent such as THF, or suitably dichloromethane and in the temperature range 0° C. to 100° C., for example 0° C. to 60° C., but suitably at or near ambient temperature. A suitable tertiary phosphine includes for example tri-n-butylphosphine or particularly tri-phenylphosphine. A suitable di-alkylazodicarboxylate includes, for example, diethyl azodicarboxylate (DEAD) or suitably di-tert-butyl azodicarboxylate (DTAD). Details of Mitsunobu reactions are contained in Tet. Letts., 31, 699, (1990); The Mitsunobu Reaction, D. L. Hughes, Organic Reactions, 1992, Vol. 42, 335-656 and Progress in the Mitsunobu Reaction, D. L. Hughes, Organic Preparations and Procedures International, 1996, Vol. 28, 127-164.

The compounds of the formulae IId and IIe are commercially available or can be prepared using conventional methods.

Step (iv):

Removal of the amino protecting group $Pg_1$ using well known methods. For example when $Pg_1$ is a BOC group, by treatment with a suitable acid such as trifluoroacetic acid or hydrochloric acid.

In an alternative route to that shown in Reaction Scheme 1, the aniline in step (i) may be reacted with the unprotected variant of the compound of the formula IIa (i.e. Pg is hydrogen), to give the compound of formula IIc directly.

The compound of formula II may also be prepared according to Reaction Scheme 2:

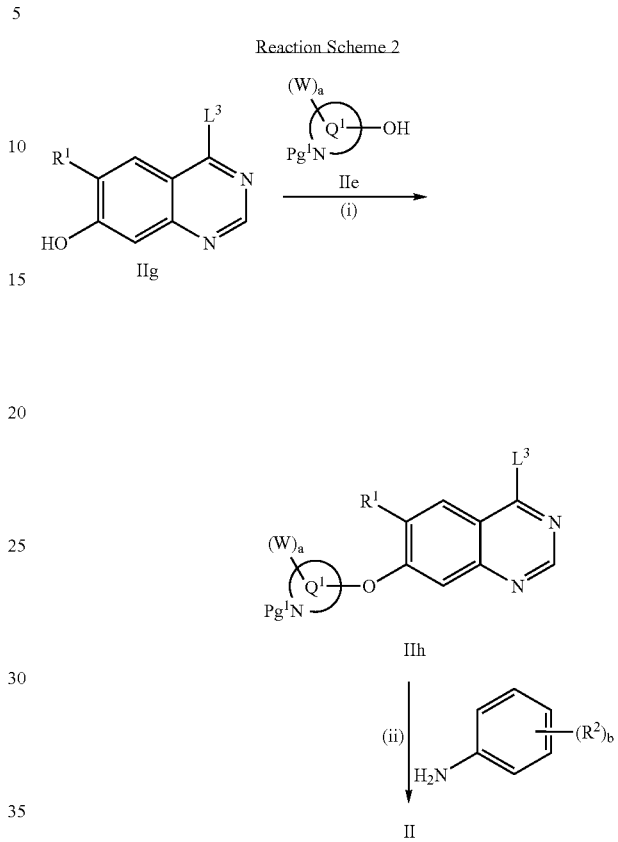

wherein $R^1$, $R^2$, $Q^1$, W, a, b, $L^3$ and $Pg^1$ are as hereinbefore defined, except any functional group is protected if necessary, and whereafter any protecting group that is present is removed by conventional means.

Conditions in Reaction Scheme 2

Step (i):

Coupling under Mitsunobu conditions as described above in relation to step (iiib) in Reaction Scheme 1.

Step (ii):

The reaction is conveniently carried out in the presence of an acid. Suitable acids include, for example hydrogen chloride gas (conveniently dissolved in a suitable solvent such as diethyl ether or dioxane) or hydrochloric acid. The reaction is conveniently carried out in a suitable inert solvent, for example as described in step (i) of Reaction Scheme 1. Conveniently, the protecting group $Pg^1$ is removed in-situ as a result of the acidic conditions during the aniline coupling reaction, for example when $Pg^1$ is tert-butoxycarbonyl. Alternatively, the protecting group may be removed using conventional methods following the reaction.

The quinazoline of the formula IIg is commercially available or can be prepared using conventional methods.

Quinazoline derivatives of the Formula II wherein $R^1$ is heterocyclyl-(2-6C)alkoxy, wherein the heterocyclyl group is nitrogen linked to the (2-6C)alkoxy group may be prepared according to Reaction Scheme 3:

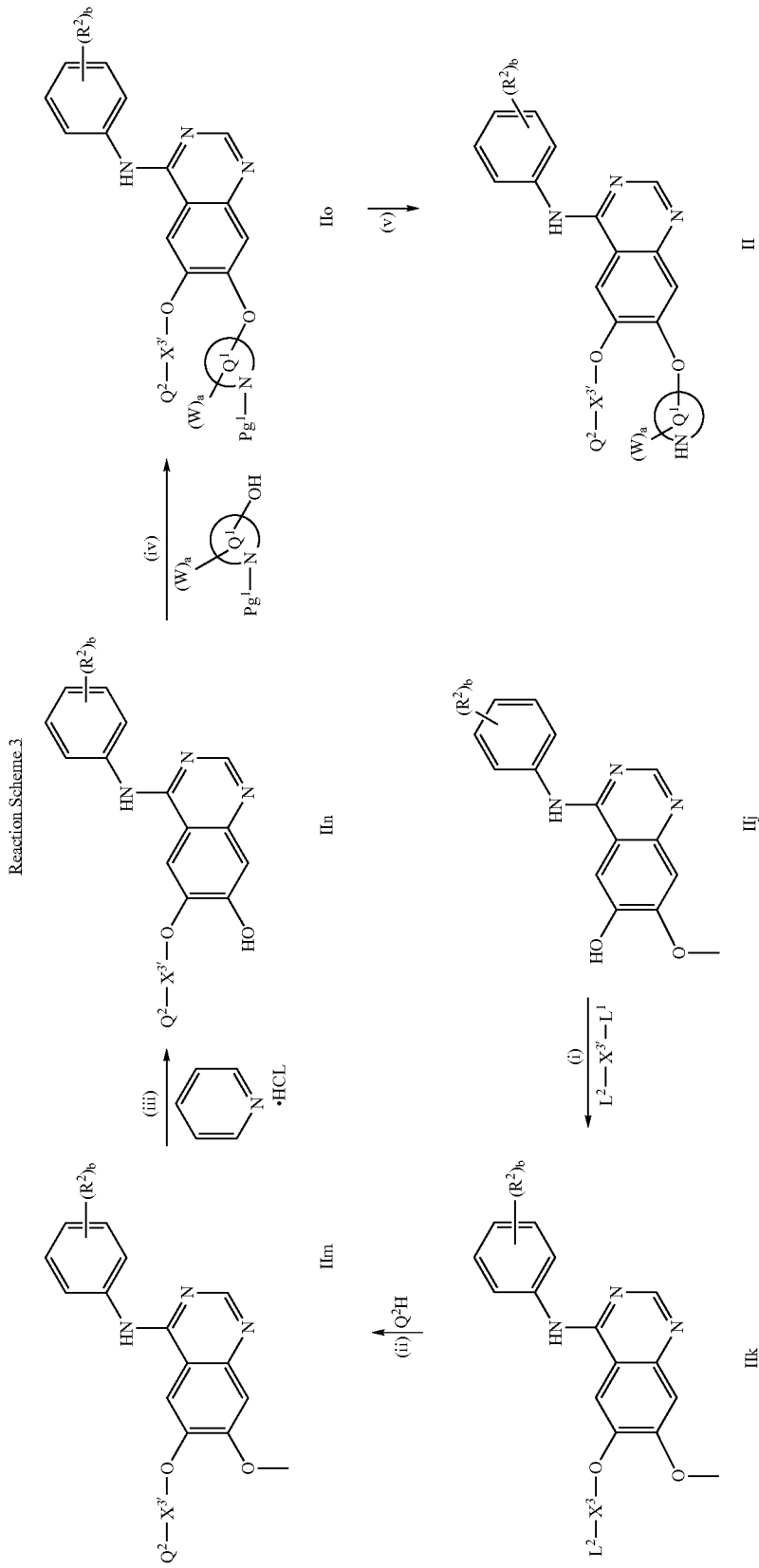

wherein $R^1$, $R^2$, $Q^1$, W, $X^2$, $L^1$, $L^2$, a, b and $Pg^1$ are as hereinbefore defined, except any functional group is protected if necessary, $X^3$' is (2-6C)-alkylene and $Q^2$ is a heterocyclyl group containing an NH ring group, and whereafter any protecting group that is present is removed by conventional means.

Step (i): $L^1$ and $L^2$ are displaceable groups as defined in relation to Process (b), for example halogeno such as chloro. The reaction with the compound of Formula IIj may be carried out under analogous conditions to those used in Process (b) described herein.

The compound of Formula IIj may be prepared using standard methods, for example as described in WO03/082831 to give a compound of the Formula IIj carrying a 2,3-di-haloanilines. Analogous methods may be used to prepare compounds of the Formula IIj by coupling 4-chloro-6-hydroxy-7-methoxyquinazoline with the appropriate aniline.

Step (ii): Analogous conditions to Process (b) described herein.

Step (iii): Cleavage of the methoxy group under standard conditions for such reactions, for example by treatment of the compound of Formula IIm with pyridinium hydrochloride at elevated temperature, for example from 60 to 180° C. conveniently about 170° C.

Step(iv): Coupling under Mitsunobu conditions as described above in relation to step (iiib) in Reaction Scheme 1.

Step (v): Deprotection to remove the amine protecting group $Pg^1$, for example when $Pg^1$ is tert-butoxycarbonyl, by treating the compound of Formula (IIo) with a suitable acid such a trifluoroacetic acid.

Reaction Conditions for Process (b)

A suitable displaceable group $L^1$ includes for example halogeno such as chloro.

The reaction is conveniently performed in the presence of a suitable base, for example, conveniently in the presence of a suitable base, for example an organic amine base such as, for example, pyridine, 2,6-lutidine, collidine, 4-dimethylaminopyridine, triethylamine, di-isopropylethylamine, N-methylmorpholine or diazabicyclo[5.4.0]undec-7-ene, or, for example, an alkali or alkaline earth metal carbonate, for example sodium carbonate, potassium carbonate, cesium carbonate, calcium carbonate, or an alkali metal hydride, for example sodium hydride, or an alkali metal disilazide such as sodium hexamethyldisilazide.

The reaction is conveniently carried out in the presence of a suitable inert solvent or diluent, for example a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one or dimethylsulfoxide.

The reaction is suitably carried out at a temperature of from 0° C. to 30° C., conveniently at ambient temperature.

When Z is hydroxy, the hydroxy group is conveniently protected during the reaction with the compound of Formula II. Suitable protecting groups are well known, for example an alkanoyl group such as acetyl. The protecting group may be removed following reaction with the compound of Formula II by conventional means, for example alkaline hydrolysis in the presence of a suitable base such as sodium hydroxide.

Compounds of the formula IV are commercially available compounds or they are known in the literature, or they can be can be prepared by standard processes known in the art.

Reaction Conditions for Process (c):

A suitable displaceable group represented by $L^2$ includes, for example a halogeno or a sulfonyloxy group, for example chloro, bromo, methylsulfonyloxy or toluene4-sulfonyloxy group. A particular group $L^2$ is chloro.

The reaction is conveniently performed in the presence of a suitable base, for example one of the bases described in relation to Process (b).

The reaction is conveniently carried out in the presence of a suitable inert solvent or diluent, for example a halogenated solvent such as methylene chloride, chloroform or carbon tetrachloride, an ether such as tetrahydrofuran or 1,4-dioxane, an ester such as ethyl acetate, an aromatic solvent such as toluene, or a dipolar aprotic solvent such as N,N-dimethylformamide, N,N-dimethylacetamide, N-methylpyrrolidin-2-one or dimethylsulfoxide.

The reaction is suitably carried out at a temperature of from 0° C. to 80° C., conveniently at ambient temperature.

Preparation of Starting Materials for Process (c)

The compound of formula V used as starting material may be prepared by, for example, reacting, conveniently in the presence of a suitable base, a quinazoline of the formula II, or salt thereof, as hereinbefore defined in relation to Process (a), with a compound of the formula Va:

$$L^2\text{-}X^2\text{—}X^1\text{-}L^5 \qquad \text{Va}$$

wherein $X^1$ and $X^2$ are as hereinbefore defined, and $L^2$ and $L^5$ are suitable displaceable groups, provided that $L^5$ is more labile than $L^2$.

Suitable displaceable groups represented by $L^2$ and $L^5$ include for example halogeno such as chloro.

The reaction is conveniently carried out in the presence of a suitable base and in a suitable inert solvent or diluent as defined above for the reaction of the quinazoline of formula V with the compound of the formula ZH.

The compounds of the formulae ZH and Va are commercially available compounds or they are known in the literature, or they can be can be prepared by standard processes known in the art.

Conveniently, in an embodiment of Process (c), a quinazoline of Formula I may be prepared directly from a quinazoline of formula II by reacting the quinazoline of formula II with a compound of formula Va and then reacting the resultant product directly with the compound of the formula ZH without isolating the compound of formula V. This reaction enables the quinazoline of Formula I to be prepared in a single reaction vessel starting with the quinazoline of formula H.

Reaction Conditions for Process (d)

Process (d) may be used to alkylate an NH group in a quinazoline derivative of Formula I, for example when Z is amino or (1-6C)alkylamino, or when the group $Z\text{-}X^2$ carries an amino or (1-6C)alkylamino substituent. Suitable reductive amination conditions are well known in the art. For example, for the production of those quinazoline derivatives of the Formula I which contain an N-methyl group, the corresponding compound containing a N—H group may be reacted with formaldehyde in the presence of a suitable reducing agent. A suitable reducing agent is, for example, a hydride reducing agent, for example formic acid, an alkali metal aluminium hydride such as lithium aluminium hydride, or, suitably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is suitably performed under acidic conditions in the presence of a suitable acid such as hydrogen chloride or acetic acid, a buffer may also be used to maintain pH at the desired level during the reaction. When the reducing agent is formic acid the reaction is conveniently carried out using an aqueous solution of the formic acid. The reaction is performed at a temperature in the range, for example, −10 to 100° C., such as 0 to 50° C., conveniently, at or near ambient temperature.

Quinazoline derivatives of the Formula I which contain an NH group (for example when Z is amino or (1-6C)alkylamino) may be prepared using one of the processes described hereinbefore. For example by coupling a compound of the Formula II with a suitable, optionally protected, amino acid using Process (a) followed by removal of any protecting groups.

Reaction Conditions for Process (e)

The cleavage reaction may conveniently be carried out by any of the many procedures known for such a transformation. A particularly suitable cleavage reaction is the treatment of a quinazoline derivative of the Formula I wherein $R^1$ is a (1-6C) alkoxy group with an alkali metal halide such as lithium iodide in the presence of 2,4,6-collidine (2,4,6-trimethylpyridine). We have found that the use of 2,4,6-collidine provides selective cleavage of the (1-6C)alkoxy group at the C6 position on the quinazoline ring. The reaction may be carried out in the presence of a suitable inert solvent or diluent as defined hereinbefore. Conveniently however the reaction may be performed using only the 2,4,6-collidine without the need for additional solvents/diluents. The reaction is suitably carried out at a temperature in the range, for example, 10 to 170° C., preferably at elevated temperature for example 120 to 170° C., for example approximately 130° C.

Reaction Conditions for Process (f)

The coupling reaction is conveniently carried out under Mitsunobu conditions as described above in relation to step (iiib) in Reaction Scheme 1.

Preparation of Starting Materials for Process (f)

The compound of Formula VI used as starting material may be prepared by, for example, the cleavage of a quinazoline derivative of the Formula I, wherein $R^1$ is, for example, methoxy using Process (e) described hereinbefore. Alternatively, compound of Formula VI may be prepared using conventional procedures. For example, when $X^1$ is CO, a compound of the Formula VI may be prepared using the method illustrated in Reaction Scheme 4:

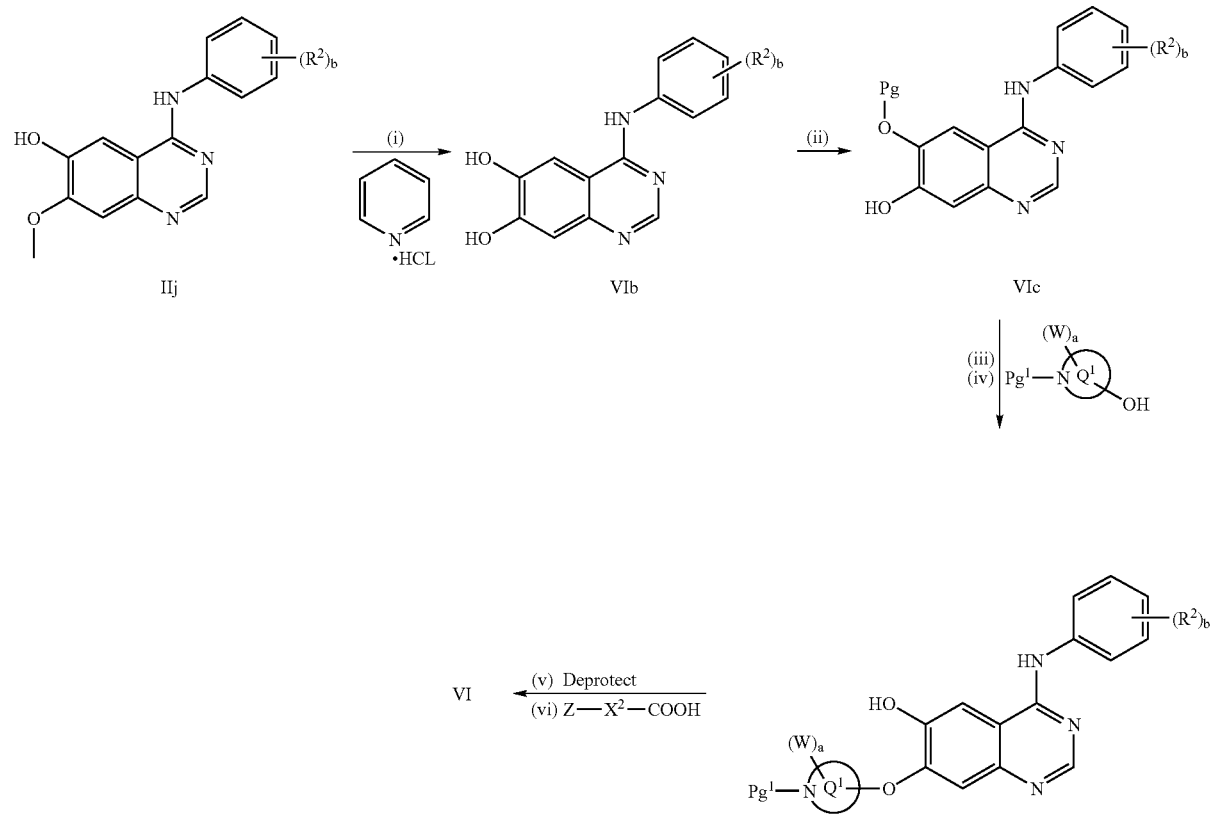

wherein $R^1$, $R^2$, $Q^1$, W, $X^2$, a, b, Pg and $Pg^1$ are as hereinbefore defined, except any functional group is protected if necessary, and whereafter any protecting group that is present is removed by conventional means.

Conditions in Reaction Scheme 4

Step (i): Cleavage of methoxy group under analogous conditions to those described in step (iii) in Reaction Scheme 3.

Step (ii) Pg is a suitable hydroxy protecting group as hereinbefore defined, for example an alkanoyl such as acetyl. The group Pg may be introduced under standard conditions for example by reacting the compound of Formula VIb with acetic anhydride.

Step (iii) Coupling under Mitsunobu conditions as described above in relation to step (iiib) in Reaction Scheme 1.

Step (iv): Deprotection to remove the protecting group Pg. For example when Pg is acetyl by alkaline hydrolysis in an alcohol, for example using a methanolic ammonia solution.

Step (v): Deprotection to remove the amine protecting group $Pg^1$, for example when $Pg^1$ is tert-butoxycarbonyl, by treating the compound of Formula (VId) with a suitable acid such a trifluoroacetic acid.

Step (vi): Coupling with acid Z-$X^2$—COOH using the method described above for Process (a).

The quinazoline derivative of the Formula I may be obtained from the above processes in the form of the free base or alternatively it may be obtained in the form of a salt, an acid addition salt. When it is desired to obtain the free base from a salt of the compound of Formula I, the salt may be treated with a suitable base, for example, an alkali or alkaline earth metal carbonate or hydroxide, for example sodium carbonate, potassium carbonate, calcium carbonate, sodium hydroxide or potassium hydroxide, or by treatment with ammonia for example using a methanolic ammonia solution such as 7N ammonia in methanol.

The protecting groups used in the processes above may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); lower alkanoyloxyalkyl groups (for example pivaloyloxymethyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl. For example a tert butoxycarbonyl protecting group may be removed from an amino group by an acid catalysed hydrolysis using trifluoroacetic acid.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group.

When a pharmaceutically acceptable salt of a quinazoline derivative of the Formula I is required, for example an acid-addition salt, it may be obtained by, for example, reaction of said quinazoline derivative with a suitable acid using a conventional procedure.

When a pharmaceutically acceptable ester of a quinazoline derivative of the Formula I is required, it may be obtained by, for example, reaction of said quinazoline derivative with a suitable acid or alcohol using a conventional procedure as herein described in relation to definition of pharmaceutically acceptable esters.

As mentioned hereinbefore some of the compounds according to the present invention may contain one of more chiral centers and may therefore exist as stereoisomers (for example when $Q^1$ is piperidin-3-yl). Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. When a specific stereoisomer is isolated it is suitably isolated substantially free for other stereoisomers, for example containing less than 20%, particularly less than 10% and more particularly less than 5% by weight of other stereoisomers.

In the section above relating to the preparation of the quinazoline derivative of Formula I, the expression "inert solvent" refers to a solvent which does not react with the starting materials, reagents, intermediates or products in a manner which adversely affects the yield of the desired product.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

Certain intermediates used in the processes described above are novel and form a further feature of the present invention. According to a further aspect of the present invention there is provided a quinazoline derivative of the Formula II as hereinbefore defined wherein a is 2 and each $R^2$, which may be the same or different, is halogeno (particularly selected from fluoro and chloro) and wherein the $R^2$ groups are located at the ortho (2-) and meta (3-) positions on the aniline ring; or a salt thereof. A particular compound of the Formula II is a compound of the Formula II wherein the anilino group is 3-chloro-2-fluoroanilino or 3-bromo-2-fluoroanilino, more particularly the anilino group is 3-chloro-2-fluoroanilino. In an embodiment in the compound of Formula II, or a salt thereof, $R^1$ is (1-4C)alkoxy; a is 0 or 1; W, when present is on a ring carbon atom in $Q^1$ and is selected from (1-4C)alkyl, hydroxy and (1-4C)alkoxy (preferably W is 0); $Q^1$ is piperidin-4-yl and the anilino group is 3-chloro-2-fluoroanilino or 3-bromo-2-fluoroanilino, more particularly the anilino group is 3-chloro-2-fluoroanilino. The intermediate of Formula II may be in the form of a salt of the intermediate. Such salts need not be a pharmaceutically acceptable salt. For example it may be useful to form prepare an intermediate in the form of a pharmaceutically non-acceptable salt if, for example, such salts are useful in the manufacture of a compound of Formula I. Preferably, salts of the compound of Formula II are pharmaceutically acceptable salts as hereinbefore defined in relation to the quinazoline derivative of Formula I.

Biological Assays

The inhibitory activities of compounds were assessed in non-cell based protein tyrosine kinase assays as well as in cell based proliferation assays before their in vivo activity was assessed in Xenograft studies.

a) Protein Tyrosine Kinase Phosphorylation Assays

This test measures the ability of a test compound to inhibit the phosphorylation of a tyrosine containing polypeptide substrate by EGFR, erbB2 or erbB4 tyrosine kinase enzyme.

Recombinant intracellular fragments of EGFR, erbB2 and erbB4 (accession numbers X00588, X03363 and L07868 respectively) were cloned and expressed in the baculovirus/Sf21 system. Lysates were prepared from these cells by treatment with ice-cold lysis buffer (20 mM N-2-hydroxyethylpiperizine-N'-2-ethanesulfonic acid (HEPES) pH 7.5, 150 mM NaCl, 10% glycerol, 1% Triton X-100, 1.5 mM $MgCl_2$, 1 mM ethylene glycol-bis(β-aminoethyl ether) N',N',N',N'-tetraacetic acid (EGTA), plus protease inhibitors and then cleared by centrifugation.

Constitutive kinase activity of these recombinant proteins was determined by their ability to phosphorylate a synthetic peptide (made up of a random co-polymer of Glutamic Acid, Alanine and Tyrosine in the ratio of 6:3:1). Specifically, Maxisorb™ 96-well immunoplates were coated with synthetic peptide (0.2 μg of peptide in a 200 μl phosphate buffered saline (PBS) solution and incubated at 4° C. overnight). Plates were washed in 50 mM HEPES pH 7.4 at room temperature to remove any excess unbound synthetic peptide. EGFR or erbB2 activities were assessed by incubation in peptide coated plates for 20 minutes at room temperature in 100 mM HEPES pH 7.4 at room temperature, adenosine trisphosphate (ATP) at Km concentration for the respective enzyme, 10 mM $MnCl_2$, 0.1 mM $Na_3VO_4$, 0.2 mM DL-dithiothreitol (DTT), 0.1% Triton X-100 with test compound in DMSO (final concentration of 2.5%). Reactions were terminated by the removal of the liquid components of the assay followed by washing of the plates with PBS-T (phosphate buffered saline with 0.5% Tween 20).

The immobilised phospho-peptide product of the reaction was detected by immunological methods. Firstly, plates were incubated for 90 minutes at room temperature with anti-phosphotyrosine primary antibodies that were raised in the mouse (4G10 from Upstate Biotechnology). Following extensive washing, plates were treated with Horseradish Peroxidase (HRP) conjugated sheep anti-mouse secondary antibody (NXA931 from Amersham) for 60 minutes at room temperature. After further washing, HRP activity in each well of the plate was measured colorimetrically using 22'-Azino-di-[3-ethylbenzthiazoline sulfonate (6)] diammonium salt crystals (ABTS™ from Roche) as a substrate.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b) EGFR Driven KB Cell Proliferation Assay

This assay measures the ability of a test compound to inhibit the proliferation of KB cells (human naso-pharangeal carcinoma obtained from the American Type Culture Collection (ATCC)).

KB cells were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $1.25 \times 10^3$ cells per well of a 96 well plate in DMEM containing 2.5% charcoal stripped serum, 1 mM glutamine and non-essential amino acids at 37° C. in 7.5% $CO_2$ and allowed to settle for 4 hours.

Following adhesion to the plate, the cells are treated with or without EGF (final concentration of 1 ng/ml) and with or without compound at a range of concentrations in dimethylsulfoxide (DMSO) (0.1% final) before incubation for 4 days. Following the incubation period, cell numbers were determined by addition of 50 μl of 3-(4,5-Dimethylthiazol-2-yl)-2,5-diphenyltetrazolium bromide (MTT) (stock 5 mg/ml) for 2 hours. MTT solution was then tipped off, the plate gently tapped dry and the cells dissolved upon the addition of 100 μl of DMSO.

Absorbance of the solubilised cells was read at 540 nm using a Molecular Devices ThermoMax microplate reader. Inhibition of proliferation was expressed as an $IC_{50}$ value. This was determined by calculation of the concentration of compound that was required to give 50% inhibition of proliferation. The range of proliferation was calculated from the positive (vehicle plus EGF) and negative (vehicle minus EGF) control values.

c) Clone 24 phospho-erbB2 Cell Assay

This immunofluorescence end point assay measures the ability of a test compound to inhibit the phosphorylation of erbB2 in a MCF7 (breast carcinoma) derived cell line which was generated by transfecting MCF7 cells with the full length erbB2 gene using standard methods to give a cell line that overexpresses full length wild type erbB2 protein (hereinafter 'Clone 24' cells).

Clone 24 cells were cultured in Growth Medium (phenol red free Dulbecco's modified Eagle's medium (DMEM) containing 10% foetal bovine serum, 2 mM glutamine and 1.2 mg/ml G418) in a 7.5% $CO_2$ air incubator at 37° C. Cells were harvested from T75 stock flasks by washing once in PBS (phosphate buffered saline, pH 7.4, Gibco No. 10010-015) and harvested using 2 mls of Trypsin (1.25 mg/ml)/ethylaminediaminetetraacetic acid (EDTA) (0.8 mg/ml) solution. The cells were resuspended in Growth Medium. Cell density was measured using a haemocytometer and viability was calculated using Trypan Blue solution before being further diluted in Growth Medium and seeded at a density of $1 \times 10^4$ cells per well (in 100 ul) into clear bottomed 96 well plates (Packard, No. 6005182).

3 days later, Growth Medium was removed from the wells and replaced with 100 ul Assay Medium (phenol red free DMEM, 2 mM glutamine, 1.2 mg/ml G418) either with or without erbB inhibitor compound. Plates were returned to the incubator for 4 hrs and then 20 μl of 20% formaldehyde solution in PBS was added to each well and the plate was left at room temperature for 30 minutes. This fixative solution was removed with a multichannel pipette, 100 μl of PBS was added to each well and then removed with a multichannel pipette and then 50 μl PBS was added to each well. Plates were then sealed and stored for up to 2 weeks at 4° C.

Immunostaining was performed at room temperature. Wells were washed once with 200 μl PBS/Tween 20 (made by adding 1 sachet of PBS/Tween dry powder (Sigma, No. P3563) to 1 L of double distilled $H_2O$) using a plate washer then 200 μl Blocking Solution (5% Marvel dried skimmed milk (Nestle) in PBS/Tween 20) was added and incubated for 10 minutes. Blocking Solution was removed using a plate washer and 200 μl of 0.5% Triton X-100/PBS was added to permeabalise the cells. After 10 minutes, the plate was washed with 200 μl PBS/Tween 20 and then 200 μl Blocking Solution was added once again and incubated for 15 minutes. Following removal of the Blocking Solution with a plate washer, 30 μl of rabbit polyclonal anti-phospho ErbB2 IgG antibody (epitope phospho-Tyr 1248, SantaCruz, No. SC-12352-R), diluted 1:250 in Blocking Solution, was added to each well and incubated for 2 hours. Then this primary antibody solution was removed from the wells using a plate washer followed by two 200 μl PBS/Tween 20 washes using a plate washer. Then 30 μl of Alexa-Fluor 488 goat anti-rabbit IgG secondary antibody (Molecular Probes, No. A-11008), diluted 1:750 in Blocking Solution, was added to each well. From now onwards, wherever possible, plates were protected from light exposure, at this stage by sealing with black backing tape. The plates were incubated for 45 minutes and then the secondary antibody solution was removed from the wells followed by two 200 ul PBS/Tween 20 washes using a plate washer. Then 100 μl PBS was added to each plate, incubated for 10 minutes and then removed using a plate washer. Then a further 100 μl PBS was added to each plate and then, without prolonged incubation, removed using a plate washer. Then 50 μl of PBS was added to each well and plates were resealed with black backing tape and stored for up to 2 days at 4° C. before analysis.

The Fluorescence signal is each well was measured using an Acumen Explorer Instrument (Acumen Bioscience Ltd.), a plate reader that can be used to rapidly quantitate features of images generated by laser-scanning. The instrument was set to measure the number of fluorescent objects above a pre-set threshold value and this provided a measure of the phosphorylation status of erbB2 protein. Fluorescence dose response data obtained with each compound was exported into a suitable software package (such as Origin) to perform curve fitting analysis. Inhibition of erbB2 phosphorylation was expressed as an $IC_{50}$ value. This was determined by calculation of the concentration of compound that was required to give 50% inhibition of erbB2 phosphorylation signal.

d) In vivo Xenograft Assay

This assay measures the ability of a test compound to inhibit the growth of a LoVo tumour (colorectal adenocarcinoma obtained from the ATCC) in Female Swiss athymic mice (Alderley Park, nu/nu genotype).

Female Swiss athymic (nu/nu genotype) mice were bred and maintained in Alderley Park in negative pressure Isolators (PFI Systems Ltd.). Mice were housed in a barrier facility with 12 hr light/dark cycles and provided with sterilised food and water ad libitum. All procedures were performed on mice of at least 8 weeks of age. LoVo tumour cell (colorectal adenocarcinoma obtained from the ATCC) xenografts were established in the hind flank of donor mice by sub cutaneous injections of $1 \times 10^7$ freshly cultured cells in 100 μl of serum free media per animal. On day 5 post-implant, mice were randomised into groups of 7 prior to the treatment with compound or vehicle control that was administered once daily at 0.1 ml/10 g body weight. Tumour volume was assessed twice weekly by bilateral Vernier calliper measurement, using the formula (length×width)×√(length×width)×(π/6), where length was the longest diameter across the tumour, and width was the corresponding perpendicular. Growth inhibition from start of study was calculated by comparison of the mean changes in tumour volume for the control and treated groups, and statistical significance between the two groups was evaluated using a Students t test.

Although the pharmacological properties of the compounds of the Formula I vary with structural change as expected, in general activity possessed by compounds of the Formula I, may be demonstrated at the following concentrations or doses in one or more of the above tests (a), (b), (c) and (d):

Test (a):—$IC_{50}$ in the range, for example, 0.001-1 μM;
Test (b):—$IC_{50}$ in the range, for example, 0.001-5 μM;
Test (c):—$IC_{50}$ in the range, for example, 0.01-5 μM;
Test (d):—activity in the range, for example, 1-200 mg/kg/day;

No physiologically unacceptable toxicity was observed in Test (d) at the effective dose for compounds tested of the present invention. Accordingly no untoward toxicological effects are expected when a compound of Formula I, or a pharmaceutically acceptable salt thereof, as defined hereinbefore is administered at the dosage ranges defined hereinafter.

By way of example, using Test (a) (for the inhibition of EGFR tyrosine kinase protein phosphorylation) and Test (b) (the KB cell assay) described above, representative compounds described in the Examples herein gave the $IC_{50}$ results shown below in Table A:

TABLE A

| Compound of Example | $IC_{50}$ (nM) Test (a) (Inhibition of EGFR tyrosine kinase protein phosphorylation) | $IC_{50}$ (nM) Test (b) (EGFR driven KB cell proliferation assay) |
|---|---|---|
| 2 | 76 | 112 |
| 3 | 41 | 55 |
| 4[1] | 30 | 37 |
| 4[3] | 65 | 84 |
| 4[4] | 52 | 109 |

According to a further aspect of the invention there is provided a pharmaceutical composition which comprises a quinazoline derivative of the Formula I, or a pharmaceutically acceptable salt or a pharmaceutically acceptable ester thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a quinazoline derivative of the formula I will naturally vary according to the nature and severity of the conditions, the age and sex of the animal or patient and the route of administration, according to well known principles of medicine.

In using a quinazoline derivative of the formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

We have found that the compounds of the present invention possess anti-proliferative properties such as anti-cancer properties that are believed to arise from their erbB family receptor tyrosine kinase inhibitory activity, particularly inhibition of the EGF receptor (erbB1) tyrosine kinase. Furthermore, certain of the compounds according to the present invention possess substantially better potency against the EGF receptor tyrosine kinase, than against other tyrosine kinase enzymes, for example erbB2, VEGF or KDR receptor tyrosine kinases. Such compounds possess sufficient potency against the EGF receptor tyrosine kinase that they may be used in an amount sufficient to inhibit EGF receptor tyrosine kinase whilst demonstrating little, or significantly lower, activity against other tyrosine kinase enzymes such as erbB2. Such compounds are likely to be useful for the selective inhibition of EGF receptor tyrosine kinase and are likely to be useful for the effective treatment of, for example EGF driven tumours.

Accordingly, the compounds of the present invention are expected to be useful in the treatment of diseases or medical conditions mediated alone or in part by erbB receptor tyrosine kinases (especially EGF receptor tyrosine kinase), i.e. the compounds may be used to produce an erbB receptor tyrosine kinase inhibitory effect in a warm-blooded animal in need of such treatment. Thus the compounds of the present invention provide a method for the treatment of malignant cells characterised by inhibition of one or more of the erbB family of receptor tyrosine kinases. Particularly the compounds of the invention may be used to produce an anti-proliferative and/or pro-apoptotic and/or anti-invasive effect mediated alone or in part by the inhibition of erbB receptor tyrosine kinases. Particularly, the compounds of the present invention are expected to be useful in the prevention or treatment of those tumours that are sensitive to inhibition of one or more of the erbB receptor tyrosine kinases, such as EGF and/or erbB2 and/or erbB4 receptor tyrosine kinases (especially EGF receptor tyrosine kinase) that are involved in the signal transduction steps which drive proliferation and survival of these tumour cells. Accordingly the compounds of the present invention are expected to be useful in the treatment of psoriasis, benign prostatic hyperplasia (BPH), atherosclerosis and restenosis and/or cancer by providing an anti-proliferative effect, particularly in the treatment of erbB receptor tyrosine kinase sensitive cancers. Such benign or malignant tumours may affect any tissue and include non-solid tumours such as leukaemia, multiple myeloma or lymphoma, and also solid tumours, for example bile duct, bone, bladder, brain/CNS, breast, colorectal, endometrial, gastric, head and neck, hepatic, lung (particularly non-small-cell lung), neuronal, oesophageal, ovarian, pancreatic, prostate, renal, skin, testicular, thyroid, uterine and vulval cancers.

According to this aspect of the invention there is provided a quinazoline derivative of the Formula I, or a pharmaceutically acceptable salt, or a pharmaceutically acceptable ester thereof, for use as a medicament.

According to a further aspect of the invention there is provided a quinazoline derivative of the Formula I, or a pharmaceutically acceptable salt, or a pharmaceutically acceptable ester thereof, for use in the production of an anti-proliferative effect in a warm-blooded animal such as a human.

Thus according to this aspect of the invention there is provided the use of a quinazoline derivative of the Formula I, or a pharmaceutically acceptable salt, or a pharmaceutically acceptable ester thereof, as defined hereinbefore in the manufacture of a medicament for use in the production of an anti-proliferative effect in a warm-blooded animal such as a human.

According to a further feature of this aspect of the invention there is provided a method for producing an anti-proliferative effect in a warm-blooded animal, such as a human, in need of such treatment which comprises administering to said animal an effective amount of a quinazoline derivative of the Formula I, or a pharmaceutically acceptable salt, or a pharmaceutically acceptable ester thereof, as hereinbefore defined.

According to a further aspect of the invention there is provided the use of a quinazoline derivative of the Formula I, or a pharmaceutically acceptable salt, or a pharmaceutically acceptable ester thereof, as defined hereinbefore in the manufacture of a medicament for use in the prevention or treatment of those tumours which are sensitive to inhibition of erbB receptor tyrosine kinases, such as EGFR and/or erbB2 and/or erbB4 (especially EGFR) tyrosine kinases, that are involved in the signal transduction steps which lead to the proliferation of tumour cells.

According to a further feature of this aspect of the invention there is provided a method for the prevention or treatment of those tumours in a warm-blooded animal such as a human which are sensitive to inhibition of one or more of the erbB family of receptor tyrosine kinases, such as EGFR and/or erbB2 and/or erbB4 (especially EGFR) tyrosine kinases, that are involved in the signal transduction steps which lead to the proliferation and/or survival of tumour cells which comprises administering to said animal an effective amount of a quinazoline derivative of the Formula I, or a pharmaceutically acceptable salt, or a pharmaceutically acceptable ester thereof, as defined hereinbefore.

According to a further feature of this aspect of the invention there is provided a compound of the Formula I, or a pharmaceutically acceptable salt, or a pharmaceutically acceptable ester thereof, for use in the prevention or treatment of those tumours in a warm-blooded animal such as a human which are sensitive to inhibition of erbB receptor tyrosine kinases, such as EGFR and/or erbB2 and/or erbB4 (especially EGFR) tyrosine kinases, that are involved in the signal transduction steps which lead to the proliferation of tumour cells.

According to a further aspect of the invention there is provided the use of a quinazoline derivative of the Formula I, or a pharmaceutically acceptable salt, or a pharmaceutically acceptable ester thereof, as defined hereinbefore in the manufacture of a medicament for use in providing a EGFR and/or erbB2 and/or erbB4 (especially a EGFR) tyrosine kinase inhibitory effect in a warm-blooded animal such as a human.

According to a further feature of this aspect of the invention there is provided a method for providing a EGFR and/or an erbB2 and or an erbB4 (especially a EGFR) tyrosine kinase inhibitory effect in a warm-blooded animal such as a human which comprises administering to said animal an effective amount of a quinazoline derivative of the Formula I, or a pharmaceutically acceptable salt, or a pharmaceutically acceptable ester thereof, as defined hereinbefore.

According to a further feature of this aspect of the invention there is provided a compound of the Formula I, or a pharmaceutically acceptable salt, or a pharmaceutically acceptable ester thereof, for use in providing a EGFR and/or erbB2 and/or erbB4 (especially a EGFR) tyrosine kinase inhibitory effect in a warm-blooded animal such as a human.

According to a further feature of the present invention there is provided the use of a quinazoline derivative of the Formula I, or a pharmaceutically acceptable salt, or a pharmaceutically acceptable ester thereof, as defined hereinbefore in the manufacture of a medicament for use in providing a selective EGFR tyrosine kinase inhibitory effect in a warm-blooded animal such as a human.

According to a further feature of this aspect of the invention there is provided a method for providing a selective EGFR tyrosine kinase inhibitory effect in a warm-blooded animal such as a human which comprises administering to said animal an effective amount of a quinazoline derivative of the Formula I, or a pharmaceutically acceptable salt, or a pharmaceutically acceptable ester thereof, as defined hereinbefore.

According to a further feature of this aspect of the invention there is provided a compound of the Formula I, or a pharmaceutically acceptable salt, or a pharmaceutically acceptable ester thereof, for use in providing a selective EGFR tyrosine kinase inhibitory effect in a warm-blooded animal such as a human.

By "a selective EGFR kinase inhibitory effect" is meant that the quinazoline derivative of Formula I is more potent against EGF receptor tyrosine kinase than it is against other kinases. In particular some of the compounds according to the invention are more potent against EGF receptor kinase than it is against other tyrosine kinases such as other erbB receptor tyrosine kinases such erbB2. For example a selective EGFR kinase inhibitor according to the invention is at least 5 times, preferably at least 10 times more potent against EGF receptor tyrosine kinase than it is against erbB2 tyrosine kinase, as determined from the relative $IC_{50}$ values in suitable assays. For example, by comparing the $IC_{50}$ value from the KB cell assay (a measure of the EGFR tyrosine kinase inhibitory activity) with the $IC_{50}$ value from the Clone 24 phospho-erbB2 cell assay (a measure of erb-B2 tyrosine kinase inhibitory activity) for a given test compound as described above.

According to a further aspect of the present invention there is provided the use of a quinazoline derivative of the Formula I, or a pharmaceutically acceptable salt, or a pharmaceutically acceptable ester thereof, as defined hereinbefore in the manufacture of a medicament for use in the treatment of a cancer (for example a cancer selected from leukaemia, multiple myeloma, lymphoma, bile duct, bone, bladder, brain/CNS, breast, colorectal, endometrial, gastric, head and neck, hepatic, lung (particularly non-small-cell lung), neuronal, oesophageal, ovarian, pancreatic, prostate, renal, skin, testicular, thyroid, uterine and vulval cancer) in a warm-blooded animal such as a human.

According to a further feature of this aspect of the invention there is provided a method for treating a cancer (for example a cancer selected from leukaemia, multiple myeloma, lymphoma, bile duct, bone, bladder, brain/CNS, breast, colorectal, endometrial, gastric, head and neck, hepatic, lung (particularly non-small-cell lung), neuronal, oesophageal, ovarian, pancreatic, prostate, renal, skin, testicular, thyroid, uterine and vulval cancer) in a warm-blooded animal, such as a human, in need of such treatment, which comprises administering to said animal an effective amount of a quinazoline derivative of the Formula I, or a pharmaceutically acceptable salt, or a pharmaceutically acceptable ester thereof, as defined hereinbefore.

According to a further aspect of the invention there is provided a compound of the Formula I, or a pharmaceutically acceptable salt, or a pharmaceutically acceptable ester thereof, for use in the treatment of a cancer (for example selected from leukaemia, multiple myeloma, lymphoma, bile duct, bone, bladder, brain/CNS, breast, colorectal, endometrial, gastric, head and neck, hepatic, lung (particularly non-small-cell lung), neuronal, oesophageal, ovarian, pancreatic, prostate, renal, skin, testicular, thyroid, uterine and vulval cancer) in a warm-blooded animal such as a human.

As mentioned above the size of the dose required for the therapeutic or prophlyactic treatment of a particular disease will necessarily be varied depending upon, amongst other things, the host treated, the route of administration and the severity of the illness being treated.

The anti-proliferative treatment/tyrosine kinase inhibitory effect/anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, MEK inhibitors, tyrosine kinase inhibitors and serine/threonine kinase inhibitors, for example other inhibitors of the epidermal growth factor family (for example other EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

(x) Cell cycle inhibitors including for example CDK inhibitiors (eg flavopiridol) and other inhibitors of cell cycle checkpoints (eg checkpoint kinase); inhibitors of aurora kinase and other kinases involved in mitosis and cytokinesis regulation (eg mitotic kinesins); and histone deacetylase inhibitors Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the Formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of the erbB receptor tyrosine protein kinases. Thus, they are useful as pharmacological standards for use in the development of new biological tests and in the search for new pharmacological agents.

The invention will now be illustrated by the following non limiting examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulfate or sodium sulfate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and/or analytical LCMS, and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at the operating frequency of the NMR apparatus used (300 or 400 MHz), using perdeuterio dimethyl sulfoxide (DMSO-$d_6$) as solvent unless otherwise indicated; the following abbreviations have been used: s, singlet; d, doublet; t, triplet; q, quartet; m, multiplet; b, broad;

(viii) chemical symbols have their usual meanings; SI units and symbols are used;

(ix) solvent ratios are given in volume:volume (v/v) terms;

(x) mass spectra (MS) were run using a Waters or Micromass electrospray LC-MS in positive or negative ion mode; values for m/z are given; generally, only ions which indicate the parent mass are reported; and unless otherwise stated, the mass ion quoted is (MH)$^+$;

(xi) where a synthesis is described as being analogous to that described in a previous example the amounts used are the millimolar ratio equivalents to those used in the previous example;

(xii) where compounds were purified using Mass-Triggered Preparative LCMS the following conditions were used:

Column: ThermoHypersil Keystone B-Basic 5 μ21 mm×100 mm

Eluant: 7.5 minutes Gradient from 20% to 95% of acetonitrile in water (buffer 2 g/l of $(NH_4)_2CO_3$, pH 8.9).

Flow rate: 25 ml/min;

(xiii) melting points (mp) were measured using a Buchi B-545 Automated melting point apparatus;

(xiv) unless stated otherwise compounds containing an asymmetrically substituted carbon atom were not resolved; and (xv) the following abbreviations have been used:

HATU    O-(7-Azabenzotriazol-1-yl)-N,N,N',N'-Tetramethyluronium Hexafluoro-Phosphate;

| | |
|---|---|
| DIPEA: | diisopropylethylamine; |
| DMA: | N,N-dimethylacetamide; |
| DMF: | N,N-dimethylformamide; |
| DCM | dichloromethane; |
| DMSO: | dimethylsulfoxide |
| EtOAc: | ethyl acetate; |
| IPA: | isopropyl alcohol; |
| TBTU: | O-(1H-Benzotriazol-1-yl)-N,N,N',N'-tetramethyl uronium tetrafluoroborate; |
| TFA: | trifluoroacetic acid; and |
| THF: | tetrahydrofuran. |

EXAMPLE 1

N-(3-Chloro-2-fluorophenyl)-7-({1-[(dimethylamino)acetyl]piperidin-4-yl}oxy)-6-methoxyquinazolin-4-amine

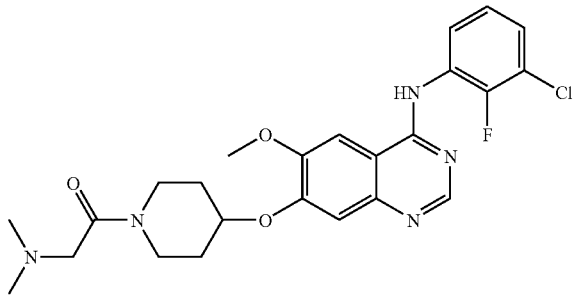

N,N-Dimethylaminoacetyl chloride hydrochloride (100 mg) was added portionwise to a stirred solution of N-(3-chloro-2-fluorophenyl)-6-methoxy-7-(piperidin-4-yloxy) quinazolin-4-amine dihydrochloride (250 mg, 0.57 mmol) and diisopropylethylamine (300 μl) in methylene chloride (25 ml) at 0° C. The reaction mixture was allowed to stir for 2 hours to room temperature. The reaction mixture was washed with saturated sodium bicarbonate solution (25 ml), dried (MgSO$_4$), filtered and evaporated. The residues were purified by column chromatography eluting with increasingly polar mixtures of methylene chloride/methanol (100/0 to 90/10), followed by methylene chloride/methanol (saturated with ammonia) (90/10). The fractions containing the desired product were combined and evaporated under vacuum to give the title product as a white foam (0.125 g, 45%); $^1$H NMR Spectrum: (DMSO $d_6$) 1.50-1.65 (m, 1H); 1.65-1.80 (m, 1H); 1.95-2.15 (m, 2H); 2.25 (s, 6H); 3.10-3.50 (m, 4H); 3.75-4.05 (m, 2H); 3.95 (s, 3H); 4.90 (m, 1H); 7.30 (m, 1H); 7.35 (s, 1H); 7.40-7.60 (m, 2H); 7.85 (s, 1H); 8.40 (s, 1H); 9.65 (s, 1H); Mass Spectrum: (M+H)$^+$ 488.

The N-(3-chloro-2-fluorophenyl)-6-methoxy-7-(piperidin-4-yloxy)quinazolin-4-amine dihydrochloride used as starting material was prepared as follows:

4.0 M HCl in Dioxane (4.0 ml) was added to a stirred suspension of 7-(benzyloxy)-4-chloro-6-methoxyquinazoline (CAS Registry No162364-72-9, prepared as described in WO98/13354, Example 1) (60 g, 0.2 mol) and 3-chloro-2-fluoroaniline (31.96 g, 0.22 mol) in acetonitrile (1200 ml). The reaction mixture was heated at 80° C. for 1 hour then left to stand overnight. Acetonitrile (500 ml) was added and the resulting precipitate filtered, washed with acetonitrile (3×500 ml) and dried under vacuum to give 7-(benzyloxy)-N-(3- chloro-2-fluorophenyl)-6-methoxyquinazolin-4-amine hydrochloride as a beige solid (85.45 g, 96%); $^1$H NMR Spectrum: (DMSO d$_6$) 4.02 (s, 3H), 5.35 (s, 2H), 7.30-7.60 (m, 9H), 7.65 (m, 1H), 8.38 (s, 1H), 8.85 (s, 1H), 11.8 (s, 1H); Mass Spectrum: (M+H)$^+$ 410.

A solution of 7-(benzyloxy)-N-(3-chloro-2-fluorophenyl)-6-methoxyquinazolin-4-amine hydrochloride (85.45 g, 0.192 mol) in trifluoroacetic acid (300 ml) was heated at 80° C. for 1 hour. The reaction mixture was the evaporated to dryness and the residues re-dissolved in methanol (200 ml). This solution was then added dropwise to a stirred aqueous solution of saturated sodium bicarbonate (500 ml). The resulting precipitate was collected by filtration, washed with acetonitrile and dried under vacuum. The resulting solids were then purified by hot (100° C.) trituration with a mixture of butanone (500 ml) and MeOH (100 ml), filtered and dried to 4-[3-chloro-2-fluoroanilino]-6-methoxyquinazolin-7-ol as a cream solid (45 g, 73%); $^1$H NMR Spectrum: (DMSO d$_6$): 3.98 (s, 3H), 7.10 (s, 1H), 7.25-7.30 (m, 1H), 7.40-7.50 (m, 1H), 7.50-7.60 (m, 1H), 7.80 (s, 1H), 8.30 (s, 1H), 9.55 (s, 1H), 10.32 (s, 1H); Mass Spectrum: (M+H)$^+$ 320.

4-[3-chloro-2-fluoroanilino]-6-methoxyquinazolin-7-ol (500 mg, 1.565 mmol) was dissolved in DMA (20 ml). tert-Butyl (4-methanesulfonyloxy)piperidine-1-carboxylate (436.6 mg, 1.565 mmol) and cesium fluoride (236.3 mg, 1.565 mmol) were added, and the mixture was heated to 60° C. with stirring. After 18 hours, tert-butyl 4-methanesulfonyloxypiperidine-1-carboxylate and cesium fluoride were again added in the same quantities to the reaction mixture and heating was continued at 60° C. for a further 18 hours. The solvent was evaporated, and the residue was partitioned between saturated aqueous sodium bicarbonate solution (50 ml) and EtOAc (2×50 ml). The organics were combined, dried over MgSO$_4$ and evaporated. The resulting product was then purified by column chromatography eluting with increasingly polar mixtures of methylene chloride/EtOAc (100/0 to 0/100). The fractions containing the desired product were combined and evaporated under vacuum to give tert-butyl 4-({4-[3-chloro-2-fluoroanilino]-6-methoxyquinazolin-7-yl}oxy)piperidine-1-carboxylate as a colourless foam (757 mg, 96%); $^1$H NMR Spectrum: (DMSO-d$_6$): 1.52 (s, 9H), 1.60-1.80 (m, 2H), 2.02-2.20 (m, 2H), 3.20-3.45 (m, 2H), 3.75-3.92 (m, 2H), 4.05 (s, 3H), 4.95 (m, 1H), 7.32-7.45 (m, 2H), 7.55-7.70 (m, 2H), 7.92 (s, 1H), 8.50 (s, 1H), 9.73 (s, 1H); Mass Spectrum: (M+H)$^+$ 503.

Trifluoroacetic acid (50 ml) was added to a solution of tert-butyl 4-({4-[3-chloro-2-fluoroanilino]-6-methoxyquinazolin-7-yl}oxy)piperidine-1-carboxylate (750 mg, 1.49 mmol) in methylene chloride (1 ml) and triethylsilane (1 ml) and the solution stirred for 1 hour. The reaction mixture was then evaporated under reduced pressure and the residues re-dissolved in EtOAc (5 ml). This solution was then treated with 1M HCl/diethylether (1 ml) followed by more diethylether (50 ml) to give a white precipitate. The resulting solids were collected following centrifugation and dried under vacuum to give N-(3-chloro-2-fluorophenyl)-6-methoxy-7-(piperidin-4-yloxy)quinazolin-4-amine dihydrochloride as a white solid (750 mg); $^1$H NMR Spectrum: (DMSO-d$_6$): 2.00-2.20 (m, 2H), 2.25-2.45 (m, 2H), 3.15-3.50 (m, 4H), 4.15 (s, 3H), 5.02 (m, 1H), 7.48 (m, 1H), 7.60-7.85 m, 3H), 8.35 (s, 1H), 8.85 (s, 1H), 9.56 (bs, 2H); Mass Spectrum: (M+H)$^+$ 403.

EXAMPLE 2

N-(3-Chloro-2-fluorophenyl)-6-methoxy-7-({1-[(2-methoxyethoxy)acetyl]piperidin-4-yl}oxy)quinazolin-4-amine

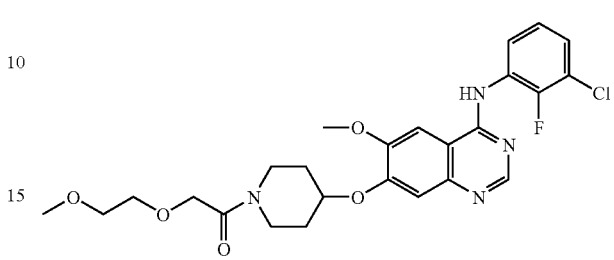

N-(3-Chloro-2-fluorophenyl)-6-methoxy-7-(piperidin-4-yloxy)quinazolin-4-amine dihydrochloride (300 mg), diisopropylethylamine (0.45 ml) and 2-(2-methoxyethoxy)acetyl chloride (0.105 g) were stirred in methylene chloride (9 ml) for 2.5 hours. Methylene chloride (20 ml) was added and the organic layer was washed with aqueous sodium hydroxide (2M, 30 ml) and water (30 ml). The resulting product was purified by flash column chromatography eluting with methanol (3%) and methylene chloride (97%) gave a foam. This was re-precipitated by stirring in diethyl ether (20 ml) to give the title product as a white solid (0.110 g); $^1$H NMR Spectrum: (DMSO d$_6$ 373K) 1.73 (m, 2H), 2.02 (m, 2H), 3.29 (s, 3H), 3.42 (m, 2H), 3.51 (t, J=7 Hz, 2H), 3.60 (t, J=9 Hz, 2H), 3.78 (m, 2H), 3.96 (s, 3H), 4.17 (s, 2H), 4.87 (m, 1H), 7.27 (m, 1H), 7.33 (s, 1H), 7.42 (m, 1H), 7.58 (m, 1H), 7.85 (s, 1H), 8.39 (s, 1H), 9.29 (br s, 1H); Mass Spectrum: (M+H)$^+$ 519; melting point 110 to 111° C.

EXAMPLE 3

N-(3-Chloro-2-fluorophenyl)-6methoxy-7-{[1-(methoxyacetyl)piperidin-4-yl]oxy}quinazolin-4-amine

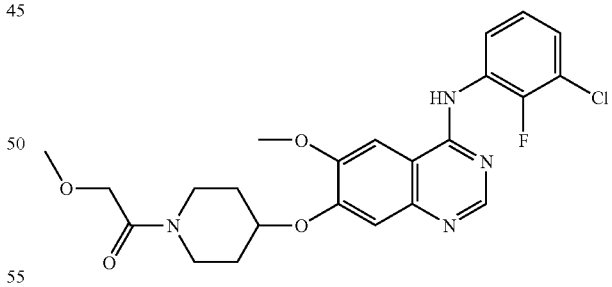

HATU (0.24 g) was added to a solution of N-(3-chloro-2-fluorophenyl)-6-methoxy-7-(piperidin-4-yloxy)quinazolin-4-amine dihydrochloride (250 mg), diisopropylethylamine (0.37 ml) and methoxyacetic acid (0.054 g) in methylene chloride (9 ml) and the mixture was stirred at room temperature for 2.5 hours. Methylene chloride (20 ml) was added and the organic layer was washed with aqueous sodium hydroxide (2M, 30 ml) and water (30 ml). The resulting product was purified by flash column chromatography eluting with methanol (3%) and methylene chloride (97%) to give a foam. This was re-precipitated by stirring in diethyl ether (20 ml) to give the title product as a white solid (0.200 g); $^1$H N Spectrum: (DMSO $d_6$ 373K) 1.73 (m, 2H), 2.02 (m, 2H), 3.37 (s, 3H), 3.41 (m, 2H), 3.77 (m, 2H), 3.98 (s, 3H), 4.09 (s, 2H), 4.85 (m, 1H), 7.26 (m, 1H), 7.30 (s, 1H), 7.39 (m, 1H), 7.59 (m, 1H), 7.81 (s, 1H), 8.38 (s, 1H), 9.34 (br s, 1H); Mass Spectrum: (M+H)$^+$ 475.

EXAMPLE 4

Using a similar procedure to that described in Example 3, N-(3-chloro-2-fluorophenyl)-6-methoxy-7-(piperidin-4-yloxy)quinazolin-4-amine dihydrochloride was coupled with the appropriate carboxylic acid to give the compounds shown in Table I:

TABLE 1

| No. and Note | R |
| --- | --- |
| [1] | hydroxyacetyl |
| [2] | ethoxyacetyl |
| [3] | 3-methoxypropanoyl |
| [4] | 3-hydroxypropanoyl |
| [5] |  |
| [6] | |
| [7] | |
| [8] | |
| [9] | |
| [10] | |
| [11] | |

TABLE 1-continued

| No. and Note | R |
| --- | --- |
| [12] | |
| [13] | |
| [14] | |
| [15] | |
| [16] | |
| [17] | |

Notes:

In Table 1 ⌇ refers to the point of attachment of the carbonyl group in Table 1 to the nitrogen in the piperidin-4-yl group.

[1] 2-[4-({4-[3-Chloro-2-fluoroanilino]-6-methoxyquinazolin-7-yl}oxy)piperidin-1-yl]-2-oxoethanol (0.170 g); $^1$H NMR Spectrum: (DMSO $d_6$ 373K) 1.78 (m, 2H), 2.02 (m, 2H), 3.42 (m, 2H), 3.75 (m, 2H), 3.97 (s, 3H), 4.11 (s, 2H), 4.84 (m, 1H), 7.25 (m, 1H), 7.31 (s, 1H), 7.40 (m, 1H), 7.50-7.67 (m, 2H), 7.82 (s, 1H), 8.38 (s, 1H), 9.31 (br s, 1H); Mass Spectrum: (M+H)$^+$ 461.

[2] N-(3-Chloro-2-fluorophenyl)-7-{[1-(ethoxyacetyl)piperidin4-yl]oxy}-6-methoxyquinazolin-4-amine as a white solid (0.185 g); $^1$H NMR Spectrum: (DMSO $d_6$ 373K) 1.18 (t, J=8 Hz, 3H), 1.74 (m, 2H), 2.03 (m, 2H), 3.41 (m, 2H), 3.52 (q, J=8 Hz, 2H), 3.79 (m, 2H), 3.98 (s, 3H), 4.12 (s, 2H), 4.84 (m, 1H), 7.23 (m, 1H), 7.32 (s, 1H), 7.42 (m, 1H), 7.58 (m, 1H), 7.81 (s, 1H), 8.38 (s, 1H), 9.30 (br s, 1H); Mass Spectrum: (M+H)$^+$ 489; melting point 160 to 161° C.

[3] N-(3-Chloro-2-fluorophenyl)-6-methoxy-7-{[1-(3-methoxypropanoyl)piperidin-4-yl]oxy}quinazolin-4-amine (0.155 g); $^1$H NMR Spectrum: (DMSO $d_6$ 373K) 1.73 (m, 2H), 2.01 (m, 2H), 2.62 (t, J=9 Hz, 2H), 3.28 (s, 3H), 3.41 (m, 2H), 3.60 (t, J=9 Hz, 2H), 3.79 (m, 2H), 3.97 (s, 3H), 4.82 (m, 1H), 7.24 (m, 1H), 7.30 (s, 1H), 7.40 (m, 1H), 7.58 (m, 1H), 7.81 (s, 1H), 8.38 (s, 1H), 9.30 (br s, 1H); Mass Spectrum: (M+H)$^+$ 489; melting point 184 to 185° C.

[4] 3-[4-({4-[3-Chloro-2-fluoroanilino]-6-methoxyquinazolin-7-yl}oxy)piperidin-1-yl]-3-oxopropan-1-ol (0.061 g); $^1$H NMR Spectrum: (DMSO $d_6$ 373K) 1.72 (m, 2H), 2.01

(m, 2H), 2.62 (t, J=8 Hz, 2H), 3.40 (m, 2H), 3.71 (m, 2H), 3.80 (m, 2H), 3.96 (s, 3H), 4.13 (t, J=5 Hz, 1H), 4.83 (m, 1H), 7.28 (m, 1H), 7.31 (s, 1H), 7.42 (m, 1H), 7.59 (m, 1H), 7.83 (s, 1H), 8.39 (s, 1H), 9.29 (br s, 1H); Mass Spectrum: (M+H)$^+$ 475; melting point 128 to 132° C.

[5] Following the coupling reaction between (2S)-2-hydroxypropanoic acid and N-(3-chloro-2-fluorophenyl)-6-methoxy-7-(piperidin-4-yloxy)quinazolin-4-amine dihydrochloride the product was purified by flash column chromatography eluting with methylene chloride/7N ammonia solution in methanol (98.6/1.4) to give a foam. This was re-precipitated by stirring in diethyl ether (20 ml) to give (2S)-1-[4-({4-[3-chloro-2-fluoroanilino]-6-methoxyquinazolin-7-yl}oxy)piperidin-1-yl]-1-oxopropan-2-ol as an amorphous white solid (0.092 g) (melting point 107 to 111° C). Recrystallisation from acetonitrile gave a crystalline solid (melting point 189 to 191° C.); $^1$H NMR Spectrum: (DMSO d$_6$) 1.19 (d, 3H), 1.48-1.75 (m, 2H), 1.94-2.13 (m, 2H), 3.21-3.53 (m, 2H), 3.93 (s, 3H), 3.78-4.06 (m, 2H), 4.40-4.52 (m, 1H), 4.83-4.99 (m, 2H), 7.28 (dd, 1H), 7.33 (s, 1H), 7.42-7.55 (m, 2H), 7.81 (s, 1H), 8.36 (s, 1H), 9.62 (s, 1H); Mass Spectrum: (M+H)$^+$ 475.

[6] Following the coupling reaction, the product was purified by flash column chromatography eluting with methylene chloride/7N ammonia solution in methanol (98/2) gave a foam. This was re-precipitated by stirring in diethyl ether (20 ml) to give (2S,3S)-1-[4-({4-[3-chloro-2-fluoroanilino]-6-methoxyquinazolin-7-yl}oxy)piperidin-1-yl]-3-methyl-1-oxopentan-2-ol as a white solid (0.244 g); $^1$H NMR Spectrum: (DMSO d$_6$) 0.78 (d, J=7 Hz, 3H), 0.91 (t, J=7 Hz, 3H), 1.21 (m, 1H), 1.44 (m, 1H), 1.61 (m, 3H), 2.05 (m, 2H), 3.40 (m, 2H), 3.79 (m, 1H), 3.95 (s, 3H), 4.00 (m, 1H), 4.28 (m, 1H), 4.43 (m, 1H), 4.93 (m, 1H), 7.29 (m, 1H), 7.36 (s, 1H), 7.48 (m, 1H), 7.53 (m, 1H), 7.83 (s, 1H), 8.39 (s, 1H), 9.63 (br s, 1H); Mass Spectrum: (M+H)$^+$ 517; melting point 114 to 118° C.

[7] Following the coupling reaction, the product was purified by flash column chromatography eluting with methanol (4%) and methylene chloride (96%) gave a foam. This was re-precipitated by stirring in diethyl ether (20 ml) to give 4-[4-({4-[3-chloro-2-fluoroanilino]-6-methoxyquinazolin-7-yl}oxy)piperidin-1-yl]-2-methyl-4-oxobutan-2-ol as a white solid (0.232 g); $^1$H NMR Spectrum: (DMSO d$_6$) 1.20 (s, 6H), 1.54-1.77 (m, 2H), 2.04 (m, 2H), 2.49 (s, 2H), 3.30 (m, 1H), 3.45 (m, 1H), 3.86 (m, 1H), 3.96 (s, 3H), 4.00 (m, 1H), 4.88 (s, 1H), 4.91 (1H, m), 7.28 (m, 1H), 7.35 (s, 1H), 7.47 (m, 1H), 7.54 (m, 1H), 7.83 (s, 1H), 8.40 (s, 1H), 9.63 (br s, 1H); Mass Spectrum: (M+H)$^+$ 503; melting point 196 to 199° C.

[8] Following the coupling reaction, the product was purified by flash column chromatography eluting with methylene chloride/7N ammonia solution in methanol (98/2) gave a foam. This was re-precipitated by stirring in diethyl ether (20 ml) to give N-(3-chloro-2-fluorophenyl)-6-methoxy-7-{[1-(tetrahydrofuran-2-ylcarbonyl)piperidin-4-yl]oxy}quinazolin-4-amine as a white solid (0.260 g); $^1$H NMR Spectrum: (DMSO d$_6$ 373K) 1.73 (m, 2H), 1.99 (m, 2H), 2.05 (m, 3H), 2.14 (m, 1H), 3.48 (m, 2H), 3.83 (m, 4H), 3.99 (s, 3H), 4.69 (t, J=7 Hz, 1H), 4.89 (1H, m), 7.29 (m, 1H), 7.37 (s, 1H), 7.43 (m, 1H), 7.60 (m, 1H), 7.83 (s, 1H), 8.39 (s, 1H), 9.33 (br s, 1H); Mass Spectrum: (M+H)$^+$ 501; melting point 199 to 201° C.

[9] Following the coupling reaction, the product was purified by flash column chromatography eluting with methanol (4%) and methylene chloride (96%) gave a foam. his was re-precipitated by stirring in diethyl ether (20 ml) to give 3-[4-({4-[3-chloro-2-fluoroanilino]-6-methoxyquinazolin-7-yl}oxy)piperidin-1-yl]-2,2-dimethyl-3-oxopropan-1-ol as a white solid (0.244 g). $^1$H NMR Spectrum: (DMSO d$_6$) 1.10 (s, 6H), 1.64 (m, 2H), 2.03 (m, 2H), 3.39 (m, 2H), 3.45 (m, 2H), 3.95 (s, 3H), 3.98 (m, 2H), 4.54 (t, J=6 Hz, 1H), 4.91 (1H, m), 7.29 (m, 1H), 7.35 (s, 1H), 7.48 (m, 1H), 7.53 (m, 1H), 7.83 (s, 1H), 8.39 (s, 1H), 9.64 (br s, 1H); Mass Spectrum: (M+H)$^+$ 503; melting point 111 to 115° C.

[10] (3R,5S)-1-Acetyl-5-{[4-({4-[3-chloro-2-fluoroanilino]-6-methoxyquinazolin-7-yl}oxy)piperidin-1-yl]carbonyl}pyrrolidin-3-ol (0.160 g); $^1$H NMR Spectrum: (DMSO d$_6$ 373K) 1.65-1.87 (m, 3H), 1.93 (s, 3H), 2.04 (m, 3H), 3.44-3.64 (m, 4H), 3.81 (m, 2H), 3.98 (s, 3H), 4.28-4.39 (m, 1H), 4.71 (m, 1H), 4.89 (m, 2H), 7.23 (m, 1H), 7.32 (s, 1H), 7.40 (m, 1H), 7.59 (m, 1H), 7.81 (s, 1H), 8.39 (s, 1H), 9.29 (br s, 1H); Mass Spectrum: (M+H)$^+$ 558; melting point 183 to 187° C.

[11] Following the coupling reaction, the product was purified by flash column chromatography eluting with methanol (3%) and methylene chloride (97%) to give a foam. This was re-precipitated by stirring in diethyl ether (20 ml) to give (2S)-1-[4-({4-[3-chloro-2-fluoroanilino]-6-methoxyquinazolin-7-yl}oxy)piperidin-1-yl]-1-oxobutan-2-ol (0.108 g) as a white solid; $^1$H NMR Spectrum: (DMSO d$_6$ 373K) 0.91 (t, J=9 Hz, 3H), 1.52 (m, 1H), 1.70 (m, 3H), 2.05 (m, 2H), 3.40 (m, 2H), 3.84 (m, 2H), 3.94 (s, 3H), 4.28 (m, 1H), 4.40 (m, 1H), 4.88 (m, 1H), 7.26 (m, 1H), 7.32 (s, 1H), 7.42 (m, 1H), 7.60 (m, 1H), 7.80 (s, 1H), 8.38 (s, 1H), 9.30 (br s, 1H); Mass Spectrum: (M+H)$^+$ 489; melting point 152 to 153° C.

[12] Following the coupling reaction, the product was purified by flash column chromatography eluting with methylene chloride/7N ammonia solution in methanol (98/2) gave a foam. This was re-precipitated by stirring in diethyl ether (20 ml) to give N-(3-chloro-2-fluorophenyl)-6-methoxy-7-({1-[(2S)-tetrahydrofuran-2-ylcarbonyl]piperidin-4-yl}oxy)quinazolin-4-amine as a white solid (0.142 g); $^1$H NMR Spectrum: (DMSO d$_6$ 373K) 1.73 (m, 2H), 1.99 (m, 2H), 2.05 (m, 3H), 2.14 (m, 1H), 3.48 (m, 2H), 3.83 (m, 4H), 3.99 (s, 3H), 4.69 (t, J=7 Hz, 1H), 4.89 (1H, m), 7.29 (m, 1H), 7.37 (s, 1H), 7.43 (m, 1H), 7.60 (m, 1H), 7.83 (s, 1H), 8.39 (s, 1H), 9.29 (br s, 1H); Mass Spectrum: (M+H)$^+$ 501; melting point 198 to 199° C.

[13] Following the coupling reaction, the product was purified by flash column chromatography eluting with methylene chloride/7N ammonia solution in methanol (98/2) gave a foam. This was re-precipitated by stirring in diethyl ether (20 ml) to give N-(3-chloro-2-fluorophenyl)-6-methoxy-7-({1-[(2R)-tetrahydrofuran-2-ylcarbonyl]piperidin-4-yl}oxy)quinazolin-4-amine as a white solid (0.212 g); $^1$H N Spectrum: (DMSO d$_6$ 373K) 1.73 (m, 2H), 1.99 (m, 2H), 2.05 (m, 3H), 2.14 (m, 1H), 3.48 (m, 2H), 3.83 (m, 4H), 3.99 (s, 3H), 4.69 (t, J=7 Hz, 1H), 4.89 (1H, m), 7.29 (m, 1H), 7.37 (s, 1H), 7.43 (m, 1H), 7.60 (m, 1H), 7.83 (s, 1H), 8.39 (s, 1H), 9.29 (br s, 1H); Mass Spectrum: (M+H)$^+$ 501; melting point 193 to 194° C.

[14] Following the coupling reaction, the product was purified by flash column chromatography eluting with methanol (2.5%) and methylene chloride (97.5%) to give a foam. This was re-precipitated by stirring in diethyl ether (20 ml) to give (2S)-1-[4-({4-[3-chloro-2-fluoroanilino]-6-methoxyquinazolin-7-yl}oxy)piperidin-1-yl]-3,3-dimethyl-1-oxobutan-2-ol (0.026 g) as a white solid; $^1$H NMR Spectrum: (DMSO d$_6$ 373K) 0.94 (s, 9H), 1.72 (m, 2H), 2.03 (m, 2H), 3.49 (m, 2H), 3.90 (m, 2H), 3.96 (s, 3H), 4.17 (m, 1H), 4.24 (m, 1H), 4.86 (m, 1H), 7.25 (m, 1H), 7.31 (s, 1H), 7.40

(m, 1H), 7.59 (m, 1H), 7.82 (s, 1H), 8.38 (s, 1H), 9.29 (br s, 1H); Mass Spectrum: (M+H)+ 517; melting point 205 to 206° C.

[15] 7-({1-[(1-acetylpiperidin-4-yl)carbonyl]piperidin-4-yl}oxy)-N-(3-chloro-2-fluorophenyl)-6-methoxyquinazolin-4-amine; ¹H NMR Spectrum: (DMSO+CD₃COOD): 1.33-1.46 (m, 1H); 1.50-1.62 (m, 1H): 1.62-1.74 (m, 3H); 1.75-1.85 (m, 1H); 2.00-2.18 (m, 2H); 2.02 (s, 3H); 2.62-2.71 (m, 1H); 2.92-3.00 (m, 1H); 3.13 (dd, 1H); 3.30-3.43 (m, 1H); 3.47-3.57 (m, 1H); 3.80-3.98 (m, 3H); 4.02 (s, 3H); 4.39 (d, 1H); 4.93 (bs, 1H); 7.41 (dd, 1H); 7.49 (s, 1H); 7.58 (dd, 1H); 7.68 (dd, 1H); 8.11 (s, 1H); 8.92 (s, 1H); Mass Spectrum: (M+H)+ 556.

[16] N-(3-chloro-2-fluorophenyl)-6-methoxy-7-{[1-(tetrahydrofuran-3-ylcarbonyl)piperidin-4-yl]oxy}quinazolin-4-amine; ¹H NMR Spectrum: (DMSO+CD₃COOD): 11.64-1.74 (m, 1H); 1.74-1.84 (m, 1H); 2.01-2.17 (m, 4H); 3.33-3.55 (m, 3H); 3.66-3.80 (m, 3H); 3.80-3.99 (m, 3H); 4.03 (s, 3H); 3.93 (bs, 1H); 7.41 (dd, 1H); 7.48 (s, 1H); 7.58 (dd, 1H); 7.67 (dd, 1H); 8.12- (s, 1H); 8.92 (s, 1H); Mass Spectrum: (M+H)+ 501.

[17] Following the coupling reaction, the product was purified by flash column chromatography eluting with methanol (5%) and methylene chloride (95%) to give a foam. This was re-precipitated by stirring in diethyl ether (20 ml) to give 1-{[4-({4-[3-chloro-2-fluoroanilino]-6-methoxyquinazolin-7-yl}oxy)piperidin-1-yl]carbonyl}cyclopropanol as a white solid (0.125 g); ¹H NMR Spectrum: (DMSO d₆ 373K) 0.80 (m, 2H), 0.95 (m, 2H), 1.72 (m, 2H), 2.02 (m, 2H), 3.54 (m, 2H), 3.96 (s, 3H), 4.00 (m, 2H), 4.87 (m, 1H), 5.90 (s, 1H), 7.25 (m, 1H), 7.31 (s, 1H), 7.40 (m, 1H), 7.58 (m, 1H), 7.80 (s, 1H), 8.38 (s, 1H), 9.30 (br s, 1H); Mass Spectrum: (M+H)+ 487; melting point 177 to 178° C.

EXAMPLE 5

N-(3-chloro-2-fluorophenyl)-6-methoxy-7-{[(3S)-1-(methoxyacetyl)piperidin-3-yl]oxy}quinazolin-4-amine

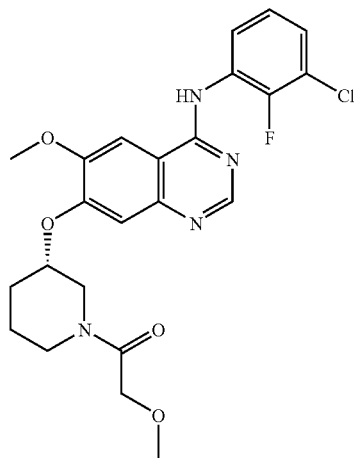

HATU (0.24 g) was added to a solution of N-(3-chloro-2-fluorophenyl)-6-methoxy-7-[(3S)-piperidin-3-yloxy]quinazolin-4-amine dihydrochloride (250 mg), diisopropylethylamine (0.37 ml) and methoxyacetic acid (0.054 g) in methylene chloride (9 ml) and the mixture was stirred at room temperature for 2.5 hours. Methylene chloride (20 ml) was added and the organic layer was washed with aqueous sodium hydroxide (2M, 30 ml) and water (30 ml). The resulting product was purified by flash column chromatography eluting with methanol (3%) and methylene chloride (97%) gave a foam. This was re-precipitated by stirring in diethyl ether (20 ml) to give the title product as a white solid (0.202 g); ¹H NMR Spectrum: (DMSO d₆ 373K) 1.60 (m, 1H), 1.88 (m, 2H), 2.10 (m, 1H), 3.32 (s, 3H), 3.51 (m, 2H), 3.62 (m, 1H), 3.87 (m, 1H), 3.98 (s, 3H), 4.02 (d, J=14 Hz, 1H), 4.12 (d, J=14 Hz, 1H), 4.66 (m, 1H), 7.26 (m, 1H), 7.33 (s, 1H), 7.43 (m, 1H), 7.62 (m, 1H), 7.83 (s, 1H), 8.40 (s, 1H), 9.34 (br s, 1H); Mass Spectrum: (M+H)+ 475.

The N-(3-chloro-2-fluorophenyl)-6-methoxy-7-[(3S)-piperidin-3-yloxy]quinazolin-4-amine dihydrochloride used as starting material was prepared as follows:

Diethylazodicarboxylate (3.73 g) was added dropwise to a mixture of tert-butyl (3R)-3-hydroxypiperidine-1-carboxylate (4.29 g), 4-chloro-6-methoxyquinazolin-7-ol (3.00 g) and triphenylphosphine (5.61 g) in methylene chloride (75 ml). The solution was then heated to 0° C. and stirred for 3 hours. After cooling the mixture was filtered and then purified by flash column chromatography eluting with isohexane/acetone/triethylamine (80/20/1) to give tert-butyl (3S)-3-[(4-chloro-6-methoxyquinazolin-7-yl)oxy]piperidine-1-carboxylate as a colourless oil (3.29 g) which was used directly; Mass Spectrum: (M+H)+ 394.

4.0M HCl in dioxane (6.0 ml) was added to a stirred suspension of tert-butyl (3S)-3-[(4-chloro-6-methoxyquinazolin-7-yl)oxy]piperidine-1-carboxylate (3.21 g) and 3-chloro-2-fluoroaniline (0.98 ml) in acetonitrile (50 mL). The reaction mixture was heated at 80° C. and left at this temperature overnight. The solvent was evaporated and the residue purified by flash column chromatography eluting with increasingly polar mixtures of methylene chloride/7N ammonia solution in methanol (97/3 to 95/5) to give N-(3-chloro-2-fluorophenyl)-6-methoxy-7-[(3S)-piperidin-3-yloxy]quinazolin-4-amine dihydrochloride as a solid (3.20 g); ¹H NMR Spectrum: (DMSO d₆) 1.56 (m, 2H), 1.72 (m, 1H), 2.12 (m, 1H), 2.48-2.59 (m, 2H), 2.82 (m,1H), 3.20 (m, 1H), 3.95 (s, 3H), 4.49 (m, 1H), 7.26 (s, 1H), 7.28 (m, 1H), 7.47 (m, 1H), 7.53 (m, 1H), 7.81 (s, 1H), 8.38 (s, 1H), 9.63(s, 1H); Mass Spectrum: (M+H)+ 403.

EXAMPLE 6

2-[(3S)-3-({4-[3-chloro-2-fluoroanilino]-6-methoxyquinazolin-7-yl}oxy)piperidin-1-yl]-2-oxoethanol

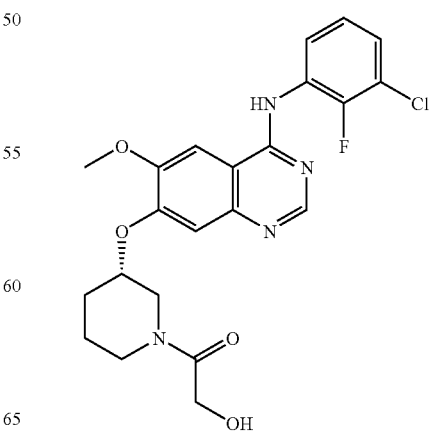

Using an analogous procedure to that described in Example 5 N-(3-chloro-2-fluorophenyl)-6-methoxy-7-[(3S)-piperidin-3-yloxy]quinazolin-4-amine dihydrochloride (250 mg) was coupled with glycolic acid (0.045 g). The resulting product was purified by flash column chromatography eluting with methanol (3%) and methylene chloride (97%) to give a foam. This was re-precipitated by stirring in diethyl ether (20 ml) to give the title product as a white solid (0.105 g); $^1$H NMR Spectrum: (DMSO d$_6$ 373K) 1.59 (m, 1H), 1.87 (m, 2H), 2.09 (m, 1H), 3.40-3.60 (m, 4H), 3.86 (m, 1H), 3.98 (s, 3H), 4.044.18 (m, 2H), 4.66 (m, 1H), 7.24 (m, 1H), 7.31 (s, 1H), 7.40 (m, 1H), 7.60 (m, 1H), 7.80 (s, 1H), 8.38 (s, 1H), 9.30 (br s, 1H); Mass Spectrum: (M+H)$^+$ 461.

EXAMPLE 7

N-(3-Chloro-2-fluorophenyl)-6-methoxy-7-({(3S)-1-[(4-methylpiperazin-1-yl)acetyl]piperidin-3-yl}oxy)quinazolin-4-amine

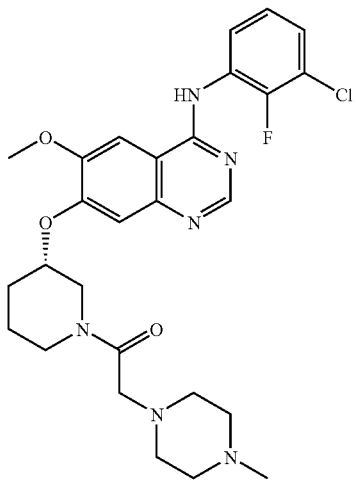

Chloroacetyl chloride (47 µl) was added to a solution of N-(3-chloro-2-fluorophenyl)-6-methoxy-7-[(3S)-piperidin-3-yloxy]quinazolin-4-amine dihydrochloride (250 mg) and diisopropylethylamine (373 µl) in methylene chloride (10 ml) and the mixture was stirred at ambient temperature for 1 hour. 1-Methylpiperazine (228 mg) was added, and the solution stirred for 1 hour before being washed with aqueous sodium hydroxide (2M, 10 ml) and water (10 ml). The organics were then purified by flash column chromatography eluting with methylene chloride/7N ammonia solution in methanol (97/3) to give a foam. This was re-precipitated by stirring in diethyl ether (20 ml) to give the title product as a white solid (0.135 g); $^1$H NMR Spectrum: (DMSO d$_6$) 1.42-1.67 (m, 1H), 1.70-1.95 (m, 2H), 1.98-2.48 (m, 9H), 2.18 (s, 3H), 2.82-3.05 (m, 1H), 3.20-4.02 (m, 8H), 4.68 (m, 1H,), 7.30 (m, 1H), 7.34 (s, 1H), 7.44-7.60 (m, 2H), 7.82 (m, 1H), 8.38 (s, 1H), 9.64 (m, 1H); Mass Spectrum: (M+H)$^+$ 543; melting point 120 to 121° C.

EXAMPLE 8

N-(3-Chloro-2-fluorophenyl)-6-methoxy-7-({1-[(4-methylpiperazin-1-yl)acetyl]piperidin-4-yl}oxy)quinazolin-4-amine

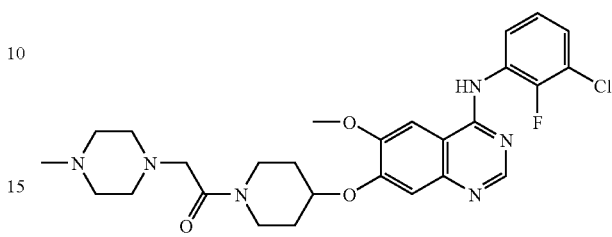

Using an analogous procedure to that described in Example 7 N-(3-chloro-2-fluorophenyl)-6-methoxy-7-(piperidin-4-yloxy)quinazolin-4-amine dihydrochloride (250 mg) was reacted with chloroacetyl chloride (47 µl), followed by 1-Methylpiperazine (228 mg) and purification to give the title product as a white solid (0.110 g); $^1$H NMR Spectrum: (DMSO d$_6$) 1.57 (m, 1H), 1.72 (m, 1H), 1.96-2.12 (m, 2H), 2.15 (s, 3H), 2.27-2.48 (m, 8H), 3.08-3.52 (m, 4H), 3.86-4.04 (m, 2H), 3.95 (s, 3H), 4.90 (m, 1H,), 7.30 (m, 1H), 7.37 (s, 1H), 7.47-7.58 (m, 2H), 7.83 (s, 1H), 8.38 (s, 1H), 9.63 (s, 1H); Mass Spectrum: (M+H)$^+$ 543.

EXAMPLE 9

(2R)-1-[4-({4-[3-Chloro-2-fluoroanilino]-6-methoxyquinazolin-7-yl}oxy)piperidin-1-yl]-1-oxopropan-2-ol (Process (a))

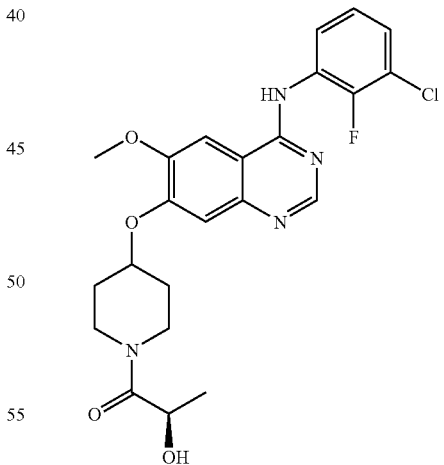

A suspension of a hydrochloride salt of N-(3-chloro-2-fluorophenyl)-6-methoxy-7-(piperidin-4-yloxy)quinazolin-4-amine (4.87 g, 11.1 mmol, prepared using an analogous process to that described in Example 1) in 1-methyl-2-pyrrolidinone (40 ml) was stirred and cooled in a bath of ice/water. Triethylamine (4.7 mls, 33.7 mmol), N,N-diisopropylethylamine (1.9 ml, 11 mmol) and D-(−)-lactic acid (1.5 g, 16.7 mmol) were added. HATU (5.27 g, 13.87 mmol) was then added portionwise such that the internal temperature remained less than 12° C. The reaction mixture was stirred at room temperature overnight and partitioned between saturated aqueous sodium bicarbonate solution (NaHCO₃) and ethyl acetate (EtOAc). The combined organic layers were washed with saturated aqueous ammonium chloride (×2), 50% aqueous brine (×2) and brine (×1), dried over anhydrous sodium sulfate, filtered and evaporated. The residues were purified by column chromatography eluting with dichloromethane/7N ammonia in methanol (96/4). Fractions containing the desired product were evaporated to a gum which was triturated with diethylether/isohexane (1:1). This solid was then crystallised from acetonitrile to give the title product as a white powder (2.93 g, 55.6%); $^1$H NMR Spectrum (DMSO $d_6$) 1.20 (d, 3H), 1.50-1.80 (m, 2H), 1.93-2.13 (m, 2H), 3.15-3.53 (m, 2H), 3.94 (s, 3H), 3.72-4.08 (m, 2H), 4.35-4.55 (m, 1H), 4.80-5.00 (m, 2H), 7.27(dd, 1H); 7.34 (s, 1H); 7.40-7.60 (m, 2H); 7.80 (s, 1H); 8.38 (s, 1H); 9.63 (s, 1H); Mass Spectrum: (M+H)⁺ 475; melting point: 189 to 189.5° C.

EXAMPLE 10

N-(3-Chloro-2-fluorophenyl)-6-methoxy-7-({1-[(2R)-2-(methylamino)propanoyl]piperidin-4-yl}oxy)quinazolin-4-amine (Process (a))

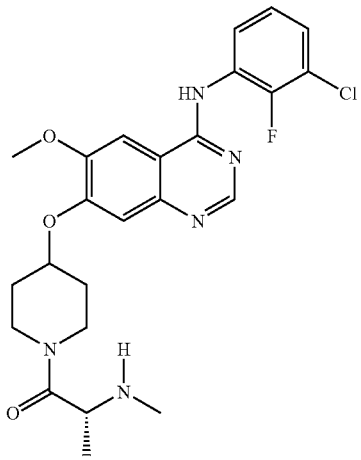

tert-butyl {(1R)-2-[4-({4-[(3-chloro-2-fluoroanilino]-6-methoxyquinazolin-7-yl}oxy)piperidin-1-yl]-1-methyl-2-oxoethyl}methylcarbamate (2.22 g, 3.77 mmol) was dissolved in acetonitrile (20 ml) and treated with 4M HCl in dioxane (3.8 ml, 15.2 mmol) at 80° C. for 5 minutes. The reaction mixture was partitioned between saturated aqueous sodium hydrogen carbonate and ethyl acetate. The organics were washed with brine (×1), dried over sodium sulfate, filtered and evaporated. The residues were purified by column chromatography eluting with dichloromethane/7N ammonia in methanol (92/8). Fractions containing the desired product were evaporated to give a gum which was triturated with diethyl ether/isohexane (1:1) to give the title product as a white powder. (1.55 g, 84.1%); $^1$H NMR Spectrum: (DMSO $d_6$ +CD₃CO₂D) 1.35 (d, 3H), 1.61-1.81 (m, 2H), 1.98-2.15 (m, 2H), 2.48 (s, 3H), 3.26-3.51 (m, 2H), 3.65-3.79 (m, 1H), 3.92 (s, 3H), 3.84-4.08 (m, 1H), 4.32-4.42 (m, 1H), 4.85-4.99 (m, 1H), 7.20-7.29 (m, 1H), 7.36 (s, 1H), 7.42-7.54 (m, 2H), 7.81 (s, 1H), 8.35 (s, 1H); Mass Spectrum: (M+H)⁺ 488.

The tert-butyl {(1R)-2-[4-({4-[(3-chloro-2-fluoroanilino]-6-methoxyquinazolin-7-yl}oxy)piperidin-1-yl]-1-methyl-2-oxoethyl}methylcarbamate starting material was prepared as follows:

A hydrochloride salt of N-(3-Chloro-2-fluorophenyl)-6-methoxy-7-(piperidin-4-yloxy)quinazolin-4-amine (2.0 g, 4.55 mmol) was coupled with N-tert-butoxycarbonyl-N-methyl-D-alanine according to the method described in Example 9. The product was purified using column chromatography eluting with dichloromethane/7N ammonia in methanol (98/2) to give tert-butyl {(1R)-2-[4-({4-[(3-chloro-2-fluoroanilino]-6-methoxyquinazolin-7-yl}oxy)piperidin-1-yl]-1-methyl-2-oxoethyl}methylcarbamate as a foam. (2.34 g, 87.6%); $^1$H NMR Spectrum: (CDCl₃) 1.29 (d, 3H), (1.48) (s, 9H), 1.75-1.89 (m, 1H), 1.89-2.04 (m, 2H), 2.07-2.22 (m, 1H), 2.75 (s, 3H), 3.26-3.42 (m, 1H), 3.50-3.85 (m, 2H), 4.02 (s, 3H), 3.91-4.28 (m, 1H), 4.65-4.93 (m, 1H), 5.10-5.21 (m, 1H), 7.05 (s, 1H), 7.13-7.21 (m, 2H), 7.28-7.33 (m, 2H), 8.44-8.54 (m, 1H), 8.69 (s, 1H); Mass Spectrum: (M+H)⁺ 588

EXAMPLE 11

N-(3-Chloro-2-fluorophenyl)-7-({1-[(2R)-2-(dimethylamino)propanoyl]piperidin-4-yl}oxy)-6-methoxyquinazolin-4-amine (Process (d))

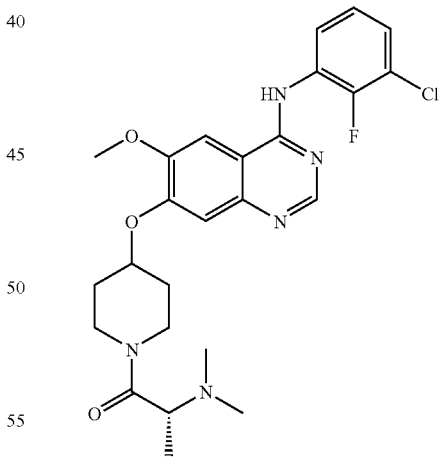

A mixture of N-(3-chloro-2-fluorophenyl)-6-methoxy-7-({1-[(2R)-2-(methylamino)propanoyl]piperidin-4-yl}oxy)quinazolin-4-amine (0.5 g, 1.03 mmol (Example 10), paraformaldehyde (0.3 g, 10.0 mmol) and anhydrous magnesium sulfate (0.25 g, 2.08 mmol) in methanol (5 ml) was treated with 4M hydrogen chloride in dioxane (257 μl, 1.03 mmol). Sodium cyanoborohydride (0.26 g, 4.12 mmol) was added and the mixture heated to 40° C. for 3 hours. The reaction mixture was then partitioned between saturated aqueous sodium hydrogen carbonate and ethyl acetate. The organics were washed with brine, dried over sodium sulfate, filtered and evaporated. The residue was purified by column chromatography eluting with dichloromethane/7N ammonia in methanol (96/4). Fractions containing the desired product were evaporated to give a gum which was triturated with diethyl ether/isohexane (1:1) to give the title product as a white powder (0.415 g, 80.7%); $^1$H NMR Spectrum: (DMSO d$_6$ +CD$_3$CO$_2$D) 1.18-1.25 (m, 3H), 1.52-1.80 (m, 2H), 1.95-2.15 (m, 2H), 2.48 (s, 6H), 3.18-3.54 (m, 2H), 3.73-3.91 (m, 1.5H), 3.92 (s, 3H), 4.00-4.14 (m, 1.5H), 4.83-4.95 (m, 1H), 7.21-7.29 (m, 1H), 7.35 (s, 1H), 7.41-7.55 (m, 2H), 7.80 (s, 1H), 8.35 (s, 1H); Mass Spectrum: (M+H)$^+$ 502.

EXAMPLE 12

N-(3-Chloro-2-fluorophenyl)-6-methoxy-7-({1-[(2S)-2-methoxypropanoyl]piperidin-4-yl}oxy)quinazolin-4-amine (Process (a))

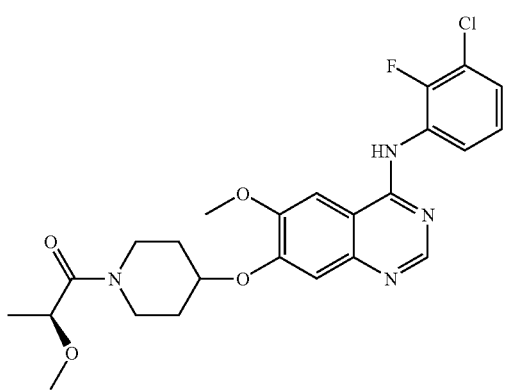

Solid TBTU (285 mg, 0.75 mmol) was added to a stirred solution of N-(3-chloro-2-fluorophenyl)-6-methoxy-7-(piperidin-4-yloxy)quinazolin-4-amine (200 mg, 0.50 mmol), DIPEA (0.261 ml, 1.50 mmol) and (S)-(−)-2-methoxypropionoic acid (57 mg, 0.55 mmol) in methylene chloride (3 ml). The resulting solution was allowed to stir at room temperature overnight, diluted with methylene chloride (20 ml), washed with 2N sodium hydroxide (2×5 ml), water (5 ml), dried (MgSO$_4$), filtered and evaporated. The resulting foams were purified using flash chromatograpy on silica eluting with increasingly polar mixtures of methanol/methylene chloride (0/100-3/97) to give the title compound as a white solid (100%); $^1$H NMR Spectrum: 1.34 (d, 3H), 1.64-1.72 (m, 2H), 2.04-2.07 (m, 2H), 3.20 (s, 3H), 3.25-3.47 (m, 2H), 3.86-3.97 (m, 2H), 4.03 (s, 3H), 4.21-4.23 (m, 1H), 4.88-4.91 (m, 1H), 7.28(dd, 1H), 7.33 (s, 1H), 7.47 (dd, 1H), 7.51 (dd, 1H), 7.92 (s, 1H), 8.38 (s, 1H), 9.67 (s, 1H); Mass Spectrum: (M+H)$^+$ 489.

The N-(3-chloro-2-fluorophenyl)-6-methoxy-7-(piperidin-4-yloxy)quinazolin-4-amine starting material was obtained from the corresponding dihydrochloride salt (Example 1) by a basic aqueous work-up at pH=11.5 and extraction of the aqueous layer by dichloromethane. The organic layer was dried on magnesium sulfate and concentrated to give the free amine as a white foam; $^1$H NMR Spectrum: (CDCl$_3$) 1.78-1.85 (m, 2H+1NH), 2.18 (m, 2H), 2.80 (m, 2H), 3.22 (m, 2H), 4.03 (s, 3H), 4.61 (m, 1H), 7.03 (s, 1R), 7.15 (m, 2H), 7.29 (s, 1H), 7.31 (m, 1H), 8.50 (m, 1H), 8.69 (s, 1NH); Mass Spectrum: (M+H)$^+$ 403.

EXAMPLE 13

N-(3-Chloro-2-fluorophenyl)-6-methoxy-7-({1-[(2R)-2-methoxypropanoyl]piperidin-4-yl}oxy)quinazolin-4-amine (Process (a))

The method described in Example 12 was repeated using (R)-(+)-2-methoxypropionic acid (57 mg, 0.55 mmol) to give the title compound as a white solid (82%); $^1$H NMR Spectrum: 1.24 (d, 3H), 1.57-1.67 (m, 2H), 2.04-2.09 (m, 2H), 3.22 (s, 3H), 3.22-3.47 (m, 2H), 3.87-3.97 (m, 2H), 3.97 (s, 3H), 4.22-4.27 (m, 1H), 4.92-4.95 (m, 1H), 7.27-7.30 (dd, 1H), 7.35 (s, 1H), 7.47 (dd, 1H), 7.60 (dd, 1H), 7.82 (s, 1H), 8.37 (s, 1H), 9.67 (s, 1H); Mass Spectrum: (M+H)$^+$ 489.

EXAMPLE 14

(2R)-2-Amino-3-[4-({4-[3-chloro-2-fluoroanilino]-6-methoxyquinazolin-7-yl}oxy)piperidin-1-yl]-3-oxopropan-1-ol (Process (a))

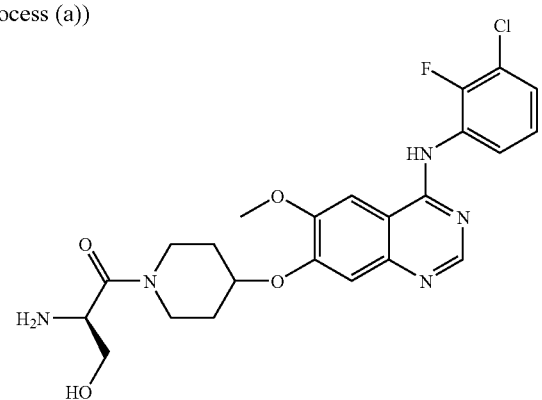

TBTU (709 mg, 1.87 mmol) was added to a stirred solution of N-(3-chloro-2-fluorophenyl)-6-methoxy-7-(piperidin-4-yloxy)quinazolin-4-amine (500 mg, 1.24 mmol), DIPEA (0.648 ml, 3.72 mmol) and N-(tert-butoxycarbonyl)-D-serine (280 mg, 1.36 mmol) in methylene chloride (3 ml). The resulting solution was allowed to stir at room temperature overnight, diluted with methylene chloride (20 ml), washed with 2N NaOH (2×5 ml), water (5 ml), dried (MgSO$_4$) and evaporated. The resulting foam was dissolved in methylene chloride (5 ml) and treated with trifluoroacetic acid (5 ml). The resulting solution was left to stand at room temperature for 1 hour, concentrated and purified by mass-triggered preparative LCMS to give the title compound (42.5%); $^1$H NMR Spectrum: 1.58-1.72 (m, 2H), 2.01-2.08 (m, 2H), 3.24-3.44 (m, 2H), 3.80-4.03 (m, 4H), 3.95 (s, 3H), 4.77 (m, 1H), 4.91-4.94 (m, 1H), 7.27(dd, 1H), 7.35 (s, 1H), 7.47 (dd, 1H), 7.51 (dd, 1H), 7.82 (s, 1H), 8.38 (s, 1H), 9.67 (s, 1H); Mass Spectrum: (M+H)$^+$ 490.

EXAMPLE 15

(2S)-2-Amino-3-[4-({4-[3-chloro-2-fluoroanilino]-6-methoxyquinazolin-7-yl}oxy)piperidin-1-yl]-3-oxopropan-1-ol The method described in Example 14 was repeated but using N-(tert-butoxycarbonyl)-L-serine (280 mg, 1.36 mmol) to give the title product (32%); $^1$H NMR Spectrum: 1.58-1.73 (m, 2H), 2.01-2.08 (m, 2H), 3.24-3.44 (m, 2H), 3.80-4.00 (m, 4H), 3.97 (s, 3H), 4.74 (m, 1H), 4.93-4.96 (m, 1H), 7.28(dd, 1H), 7.35 (s, 1H), 7.47 (dd, 1H), 7.51 (dd, 1H), 7.82 (s, 1H), 8.37 (s, 1H), 9.67 (s, 1H); Mass Spectrum: (M+H)$^+$ 490.

EXAMPLE 16

(2S)-3-[4-({4-[3-Chloro-2-fluoroanilino]-6-methoxyquinazolin-7-yl}oxy)piperidin-1-yl]-2-(dimethylamino)-3-oxopropan-1-ol (Process(d))

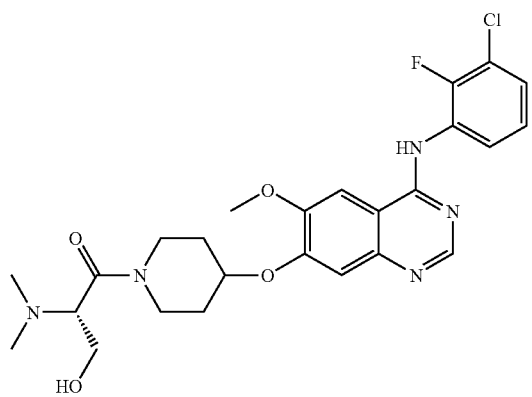

Solid NaCNBH$_3$ (38.3 mg, 0.614 mmol) was added to a stirred solution of (2S)-2-amino-3-[4-({4-[3-chloro-2-fluoroanilino]-6-methoxyquinazolin-7-yl}oxy)piperidin-1-yl]-3-oxopropan-1-ol (150 mg, 0.307 mmol, Example 15), sodium acetate trihydrate (251 mg, 3.07 mmol), formaldehyde 37% (aq) (2.5 ml) and acetic acid (184 mg, 3.07 mmol) at 0-5° C. The resulting solution was allowed to warm to room temperature and stir for 1 hour. The mixture was then evaporated and the resulting yellow residue was purified by flash chromatography on silica gel eluting with increasingly polar mixtures of dichloromethane/7N ammonia in methanol (100/0-85/15). Fractions containing the desired product were combined and evaporated to give the title compound as a white solid (26%); $^1$H NMR Spectrum: 1.52-1.69 (m, 2H), 1.94-2.07 (m, 2H), 2.28-2.30 (2 x s, 6H), 3.15-3.22 (m, 2H), 3.53-3.76 (m, 4H), 3.94 (s, 3H), 4.02 (m, 1H), 4.49 (m, 1H), 4.92-4.94 (m, 1H), 7.27(dd, 1H), 7.34 (s, 1H), 7.47 (dd, 1H), 7.51 (dd, 1H), 7.81 (s, 1H), 8.38 (s, 1H), 9.65 (s, 1H); Mass Spectrum: (M+H)$^+$ 518.

EXAMPLE 17

(2R)-3-[4-({4-[3-Chloro-2-fluoroanilino]-6-methoxyquinazolin-7-yl}oxy)piperidin-1-yl]-2-(dimethylamino)-3-oxopropan-1-ol (Process(d))

The process described in Example 16 was repeated using (2R)-2-amino-3-[4-({4-[3-chloro-2-fluoroanilino]-6-methoxyquinazolin-7-yl}oxy)piperidin-1-yl]-3-oxopropan-1-ol (150 mg, 0.307 mmol, Example 14) to give the title compound (32%); $^1$H NMR Spectrum: 1.58-1.69 (m, 2H), 1.93-2.06 (m, 2H), 2.26-2.28 (2×s, 6H), 3.17-3.20 (m, 2H), 3.53-3.74 (m, 4H), 3.94 (s, 3H), 4.04 (m, 1H), 4.47 (m, 1H), 4.91 (m, 1H), 7.26 (dd, 1H), 7.35 (s, 1H), 7.47 (dd, 1H), 7.51 (dd, 1H), 7.81 (s, 1H), 8.37 (s, 1H), 9.66 (s, 1H); Mass Spectrum: (M+H)$^+$ 518.

EXAMPLE 18

(2S)-1-(4-{[4-[3-Chloro-2-fluoroanilino]-6-(2-pyrrolidin-1-ylethoxy)quinazolin-7-yl]oxy}piperidin-1-yl)-1-oxopropan-2-ol (Process (b))

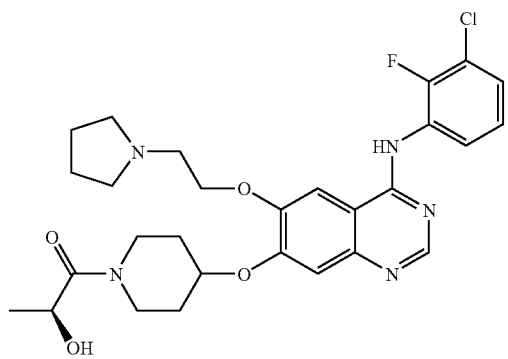

(S)-(−)-2-Acetoxyproprionyl chloride (0.131 g, 0.87 mmol) was added to a stirred solution of N-(3-chloro-2-fluorophenyl)-7-(piperidin-4-yloxy)-6-(2-pyrrolidin-1-ylethoxy)quinazolin-4-amine trihydrochloride (220 mg, 0.395 mmol) and triethylamine (0.110 ml, 0.79 mmol) in methylene chloride (10 ml) at −10° C. The resulting solution was allowed to warm to room temperature and stirred for 30 minutes. The resulting yellow solution was diluted with methylene chloride (10 ml) and washed with water (3×5 ml), dried (MgSO$_4$) and evaporated. The resulting foam was dissolved in THF (1 ml) and pyrrolidine (1 ml) was added. The mixture was heated at 70° C. for 3 hours, evaporated and the residues purified by flash chromatography on silica gel eluting with dichloromethane/7N ammonia in methanol (95/5). Fractions containing the desired product were combined and evaporated to give the title product as a white solid. (0.099 g, 45.6%); $^1$H NMR Spectrum: (DMSO-d$_6$): δ1.20 (d, 3H), 1.52-1.82 (m, 6H), 1.86-2.08 (m, 4H), 3.24-3.50 (m, 4H), 3.74-3.86 (m, 2H), 4.28 (m, 2H), 4.45 (m, 1H), 4.89-4.95 (m, 3H), 7.27 (dd, 1H), 7.36 (s, 1H), 7.48 (dd, 1H), 7.53 (dd, 1H), 7.87 (s, 1H), 8.38 (s, 1H), 9.65 (s, 1H); Mass Spectrum: (M+H)$^+$ 558.

The N-(3-chloro-2-fluorophenyl)-7-(piperidin-4-yloxy)-6-(2-pyrrolidin-1-ylethoxy)quinazolin-4-amine trihydrochloride used as a starting material (1) was prepared as follows:

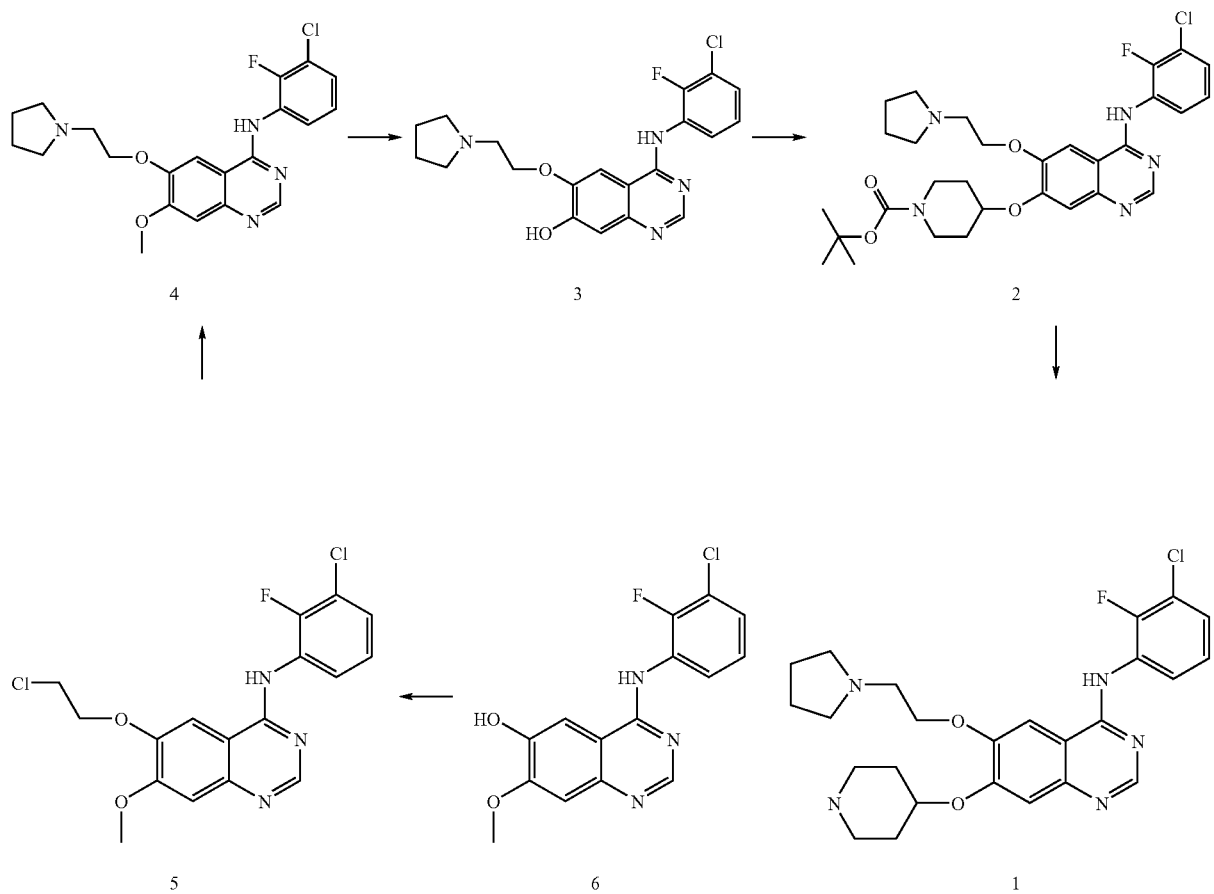

1,2-Dichloroethane (5 ml) was added to a stirred suspension of 4-(3-chloro-2-fluoroanilino)-6-hydroxy-7-methoxyquinazoline 6 (2.0 g, 6.27 mmol, prepared as described in Reference Example 2 of WO03/082831) and potassium carbonate (1.39 g, 10.0 mmol) in DMF (10 ml), and the resulting suspension was heated at 60° C. for 48 hours. The reaction mixture was diluted with methylene chloride (50 ml) and washed with water (3×20 ml), dried (MgSO$_4$) and evaporated to dryness to afford 5 (2.39 g, 100%) as a brown oil which was used without further purification; Mass Spectrum: (M+H)$^+$ 382.

Pyrrolidine (4.44 g, 5.13 ml, 62.5 mmol) was added to a stirred solution of 5 (2.38 g, 6.25 mmol) in DMF (30 ml) and the resulting pale brown solution was heated at 90° C. for 2 hours. The reaction mixture was evaporated to dryness using a rotary evaporator and under high vacuum to afford 4 (2.6 g, 100%) as a brown foam; Mass Spectrum: (M+H)$^+$ 417.

Intermediate 4 (2.60 g, 6.3 mmol) was added to neat liquid pyridinium hydrochloride (3.6 g, 31.3 mmol) at 170° C. over a period of 5 minutes. The reaction mixture was allowed to stir at 170° C. for 1 hour. The reaction mixture was cooled to room temperature and the resulting solid was suspended in water (30 ml) and the resulting black precipitate eliminated by filtration. The pH of the filtrate was increased to 7 with concentrated aqueous ammonia and the resulting solution was evaporated to dryness. The resulting beige solid was purified by flash chromatography on silica gel eluting with increasingly polar mixtures of dichloromethane/7N ammonia in methanol (100/0-85/15). Fractions containing the desired product were combined and evaporated to give 3 as a pale green foam (1.62 g, 64%). Mass Spectrum: (M+H)$^+$ 403.

Di-tert-butylazodicarboxylate (0.571 g, 2.48 mmol) was added to a stirred solution of 3 (500 mg, 1.24 mmol), 4-hydroxy-1-tert-butoxycarbonylpiperidine (374 mg, 1.86 mmol) and triphenylphosphine (660 mg, 2.48 mmol) in THF (10 ml) at 0° C. over 5 minutes. The resulting yellow solution was allowed to warm to room temperature and subsequently heated at 70° C. for 1 hour. The reaction mixture was concentrated and the residues were purified by flash chromatography on silica gel eluting with increasingly polar mixtures of methylene chloride/7N ammonia in methanol (100/0-95/5). Fractions containing the desired product were combined and evaporated to give a 2 as a pale green oil (0.52 g, 72%); Mass Spectrum: (M+H)$^+$ 586.

TFA (1 ml) was added to a stirred solution of 2 (220 mg, 0.395 mmol) in methylene chloride (1 ml) at 0° C. over 5 minutes. The resulting yellow solution was allowed to warm to room temperature and stir for 1 hour. The reaction mixture was evaporated to dryness and the residues re-dissolved in methylene chloride (10 ml). Ethyl ether (10 ml) was added followed by a 4.0 M solution of HCl in dioxane (2 ml). The resulting thick white precipitate was collected by filtration, washed with Ethyl ether (3×2 ml) and dried to a constant weight to give N-(3-chloro-2-fluorophenyl)-7-(piperidin-4-yloxy)-6-(2-pyrrolidin-1-ylethoxy)quinazolin-4-amine trihydrochloride (1) as a white solid which was used without further purification (0.48 g, 100%); Mass Spectrum: (M+H)$^+$ 486.

EXAMPLE 19
(2S)-1-(4-{[4-[3-Chloro-2-fluoroanilino]-6-(2-methoxyethoxy)quinazolin-7-yl]oxy}piperidin-1-yl)-1-oxopropan-2-ol (Process (a))

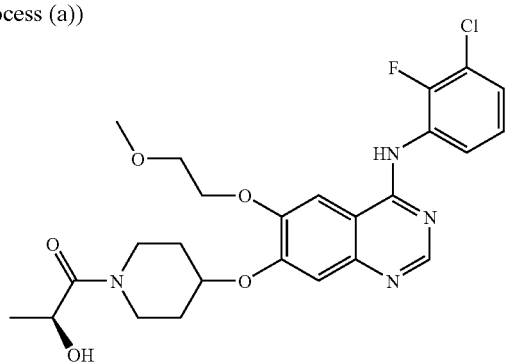

TBTU (200 mg, 0.525 mmol) was added to a stirred solution of N-(3-chloro-2-fluorophenyl)-6-(2-methoxyethoxy)-7-(piperidin-4-yloxy)quinazolin-4-amine dihydrochloride (180 mg, 0.404 mmol), L-(+)-lactic acid (37 mg, 0.44 mmol) and DIPEA (0.091 ml, 0.525 mmol) in methylene chloride (10 ml). The resulting solution was stirred at room temperature for 2 hours then diluted with methylene chloride (10 ml). This solution was washed with 2N NaOH (2×5 ml), dried (MgSO$_4$), filtered and evaporated. The residues were purified by flash chromatography on silica gel eluting with methylene chloride/7N ammonia in methanol (95/5) to give the title product as a white solid (89 mg, 42.6%); $^1$H NMR Spectrum: (DMSO-d$_6$): δ1.21 (d, 3H), 1.64-1.72 (m, 2H), 1.86-2.07 (m, 2H), 3.37-3.46 (m, 2H), 3.77-3.92 (m, 5H), 4.27 (m, 2H), 4.46 (m, 1H), 4.90-4.92 (m, 3H), 7.29 (dd, 1H), 7.36 (s, 1H), 7.48 (dd, 1H), 7.52 (dd, 1H), 7.86 (s, 1H), 8.38 (s, 1H), 9.63 (s, 1H); Mass Spectrum : (M+H)$^+$ 519.

The N-(3-chloro-2-fluorophenyl)-6-(2-methoxyethoxy)-7-(piperidin-4-yloxy)quinazolin-4-amine dihydrochloride (intermediate 7 in the reaction scheme below) used as starting material was prepared as follows:

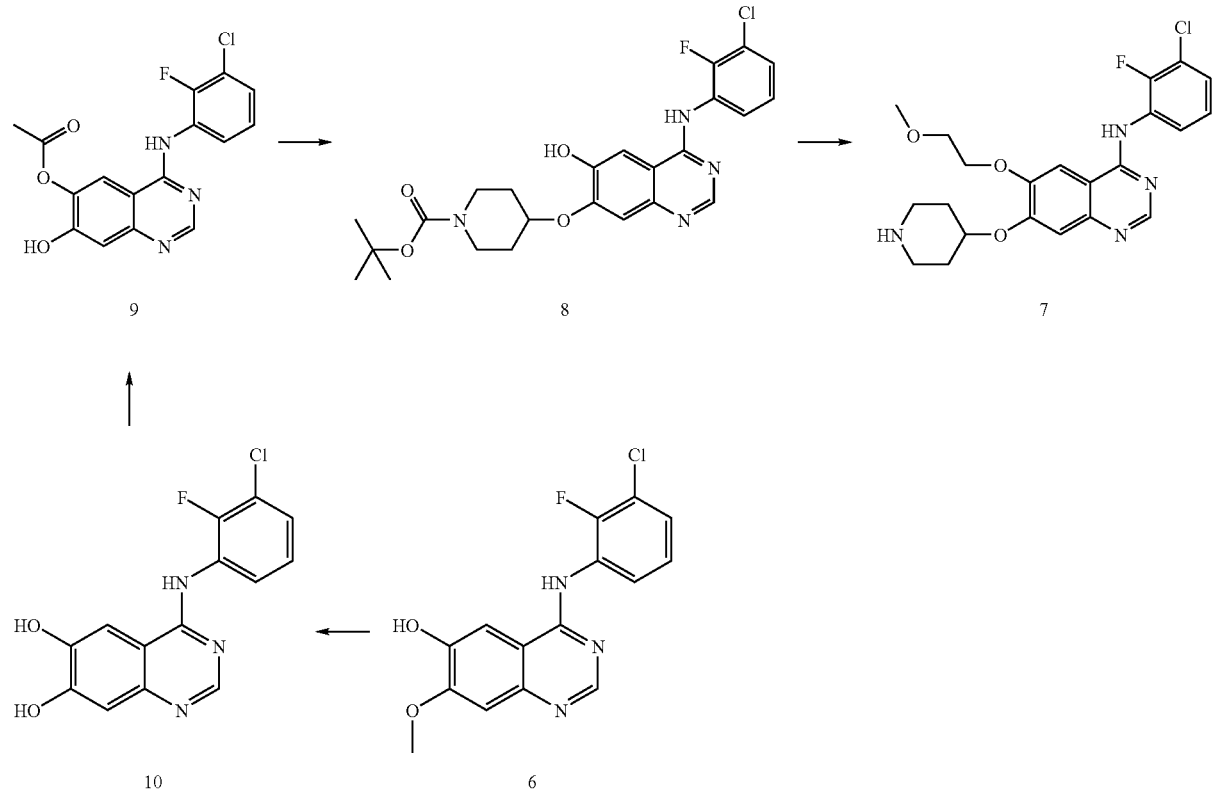

Solid 4-(3-chloro-2-fluoroanilino)-6-hydroxy-7-methoxyquinazoline 6 (1.00 g, 3.13 mmol) was added to neat liquid pyridinium hydrochloride (3.62 g, 31.3 mmol) at 170° C. over a period of 10 minutes. The reaction mixture was stirred at 170° C. for 2 hours then cooled to room temperature. The mixture was then suspended in water (30 ml) and the resulting precipitate was collected by filtration, washed with acetonitrile (5 ml) diethyl ether (5 ml) and dried to a constant weight in a vacuum oven at 50° C. to afford 10 as a beige solid (0.71 g, 77%); Mass Spectrum: (M+H)+ 306.

Acetic anhydride (117 mg, 1.15 mmol) and a solution NaOH (46 mg, 1.15 mmol) in water (3 ml) was added to a stirred suspension of 10 (350 mg, 1.15 mmol) in THF (3 ml) at −10° C. The resulting two-phase mixture was stirred at room temperature for 2 hours. The organic phase was retained, dried (MgSO$_4$) and evaporated to dryness. The resulting beige foam was triturated with acetonitrile (3 ml), cooled to 0° C. and the resulting precipitate was collected by filtration and dried to a constant weight at 40° C. in a vacuum oven to give 9 as a beige solid (232 mg, 68%); Mass Spectrum: (M+H)+ 348.

Solid di-tert-butylazodicarboxylate (364 mg, 1.58 mmol) was added to a stirred solution of 9 (250 mg, 0.72 mmol), triphenylphosphine (420 mg, 1.58 mmol) and 4-hydroxy-1-tert-butoxycarbonylpiperidine (289 mg, 1.44 mmol) in THF (10 ml) at room temperature over 5 minutes. The resulting yellow solution was stirred at room temperature for 2 hours and concentrated to afford a yellow foam. The foam was dissolved in 7N NH$_3$ in MeOH (5 ml) and left to stand for 1 hour. The solution was concentrated and purified by flash chromatography on silica gel (elution with a mixture of DCM-MeOH 95/5) to give 8 (138 mg, 39%) as a beige foam; Mass Spectrum: (M+H)+ 489.

Solid di-tert-butylazodicarboxylate (166 mg, 0.72 mmol) was added to a stirred solution of 8 (115 mg, 0.24 mmol), triphenylphosphine (0.191 g, 0.72 mmol) and 2-methoxyethanol (55 mg, 0.72 mmol) in THF (2 ml) at room temperature over 5 minutes. The resulting yellow solution was stirred at room temperature for 2 hours then concentrated to a yellow foam. This was dissolved in DCM (1 ml), treated with trifluoroacetic acid (1 ml) and left to stand for 1 hour. The solution was concentrated and purified by mass-triggered preparative LCMS to give N-(3-chloro-2-fluorophenyl)-6-(2-methoxyethoxy)-7-(piperidin-4-yloxy)quinazolin-4-amine dihydrochloride (7) as a white solid (80 mg, 77%); Mass Spectrum: (M+H)+ 447.13.

EXAMPLE 20

4-[3-chloro-2-fluoroanilino]-7-({1-[(2S)-2-hydroxypropanoyl]piperidin-4-yl}oxy)quinazolin-6-ol

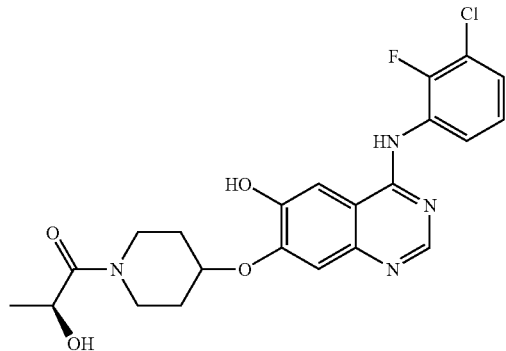

Solid lithium iodide (2.11 g, 15.8 mmol) was added to stirred neat 2,4,6-collidine (5 ml) at 130° C. The resulting yellow solution was heated at 130° C. for 1 hour. Solid (2S)-1-[4-({4-[(3-chloro-2-fluoroanilino]-6-methoxyquinazolin-7-yl}oxy)piperidin-1-yl]-1-oxopropan-2-ol (1.5 g, 3.17 mmol, Example 4[5]) over a period of 10 minutes. The resulting solution was stirred at 130° C. for 16 hours to give a dark brown solid precipitate. The liquid was decanted and the solid was purified by mass-triggered preparative LCMS to give the title product as a brown solid (1.30 g, 87%); $^1$H NMR Spectrum: (DMSO-d$_6$): δ1.21 (d, 3H), 1.61-1.77 (m, 2H), 1.95-2.08 (m, 2H), 3.41-3.51 (m, 2H), 3.86-3.92 (m, 2H), 4.47 (m, 1H), 4.91 (m, 1H), 7.26 (m, 1H), 7.32 (s, 1H), 7.45 (m, 1H), 7.53 (m, 1H), 7.70 (s, 1H), 8.33 (s, 1H), 9.45 (s, 2H); Mass Spectrum: (M+H)+ 461.

EXAMPLE 21

(2S)-1-[4-({4-[3-Chloro-2-fluoroanilino]-6-isopropoxyquinazolin-7-yl}oxy)piperidin-1-yl]-1-oxopropan-2-ol (Process (f))

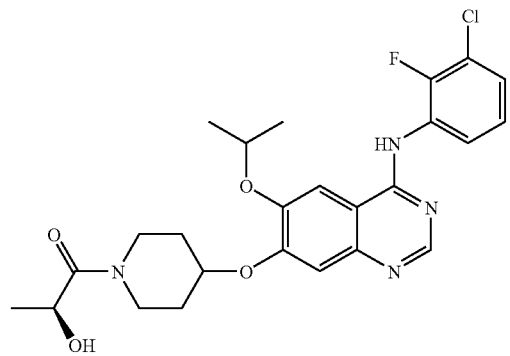

Solid di-tert-butylazodicarboxylate (225 mg, 0.98 mmol) was added to a stirred solution of 2-propanol (0.074 ml, 0.98 mmol) and triphenylphosphine (260 mg, 0.98 mmol) in THF (1 ml) at 0° C. over 5 minutes. The resulting yellow solution was allowed to warm to room temperature and 4-[3-chloro-2-fluoroanilino]-7-({1-[(2S)-2-hydroxypropanoyl]piperidin-4-yl}oxy)quinazolin-6-ol (250 mg, 0.33 mmol, Example 20) was added. The mixture was heated at 80° C. for 3 hours, cooled and evaporated. The residues were purified by mass-triggered preparative LCMS to give the title compound as a white solid (75 mg, 45.7%); $^1$H NMR Spectrum: (CDCl$_3$): δ1.37 (d, 3H), 1.43 (d, 6H), 1.61-1.72 (m, 2H), 1.95-2.07 (m, 2H), 3.38-3.50 (m, 2H), 3.78-3.88 (m, 2H), 4.49 (m, 1H), 4.66

(m, 1H), 4.82 (m, 1H), 7.15 (m, 3H), 7.31 (s, 1H), 8.52 (s, 1H), 8.69 (s, 1H); Mass Spectrum: (M+H)+ 503.

EXAMPLE 22

(2S)-1-[4-({4-[(3-Chloro-4-fluoroanilino]-6-methoxyquinazolin-7-yl}oxy)piperidin-1-yl]-1-oxopropan-2-ol.

(Process (a))

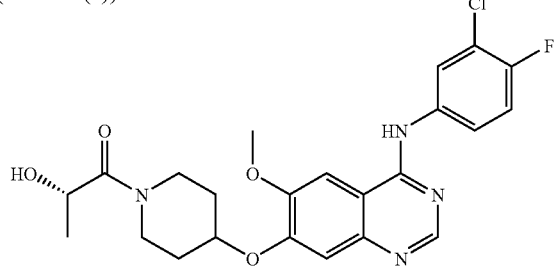

HATU (190 mg, 0.5 mmol) was added to a stirred solution of N-(3-chloro-4-fluorophenyl)-6-methoxy-7-(piperidin-4-yloxy)quinazolin-4-amine hydrochloride (200 mg, 0.456 mmol), L-(+)-lactic acid (45 mg, 0.5 mmol) and N-methyl morpholine (0.15 ml, 1.39 mmol) in DMF (10 ml) at room temperature. After 2 hours the mixture was evaporated to dryness and the residues were purified by column chromatography on silica eluting with increasingly polar mixtures of dichloromethane/methanol (99/1-90/10). Fractions containing the desired product were evaporated to a gum. This was triturated with diethylether (10 ml) and the resulting solid was collected by filtration and dried under high vacuum to give the title product as a white powder. (54.2 mg, 25%); $^1$H NMR Spectrum: (DMSO $d_6$) 1.1-1.3 (m, 3H), 1.5-1.8 (m,2H), 1.9-2.15 (m, 2H), 3.0-3.60 (m, 2H +H$_2$O), 3.7-4.1 (m, 2H), 3.95 (s, 3H), 4.43 (m, 1H), 4.95 (m, 2H), 7.32 (s, 1H), 7.47 (dd, 1H), 7.7-7.8 (m, 1H), 7.83 (s, 1H), 8.0-8.1 (m, 1H), 8.58 (s, 1H), 9.87 (bs, 1H); Mass Spectrum: (M+H)+ 475.

The N-(3-chloro-4-fluorophenyl)-6-methoxy-7-(piperidin-4-yloxy)quinazolin-4-amine hydrochloride used as the starting material was prepared as follows:

Di-tert-butylazodicarboxylate (1.64 g, 7.14 mmol) in methylene chloride (20 ml) was added slowly to a stirred suspension of 4-Chloro-6-methoxyquinazolin-7-ol (1.0 g, 4.76 mmol, prepared as described in WO2004041829, Example 1 therein (preparation of starting materials)), 4-hydroxy-1-tert-butoxycarbonylpiperidine (1.44 g, 7.14 mmol) and triphenylphosphine (1.87 g, 7.14 mmol) in methylene chloride (50 ml) at 5° C. under an atmosphere of nitrogen. The reaction mixture was allowed to warm to room temperature for 18 hours. The reaction mixture was then filtered and purified by flash chromatography on silica eluting with increasingly polar mixtures of isohexane/ethyl acetate/triethylamine (75/24/1 followed by 0/99/1). The fractions containing the desired product were combined and evaporated under vacuum to give tert-butyl 4-[(4-chloro-6-methoxyquinazolin-7-yl)oxy]piperidine-1-carboxylate as a white solid (1.75 g, 93.4%); $^1$H NMR Spectrum: (DMSO $d_6$) 1.40 (s, 9H), 1.5-1.7 (m, 2H), 1.9-2.1 (m, 2H), 3.1-3.3 (m, 2H), 3.60-3.80 (m, 2H), 3.95 (s, 3H), 4.92 (m, 1H), 7.38 (s, 1H), 7.58 (s, 1H), 8.83 (s, 1H); Mass Spectrum: (M+H)+ 394.

4.0M HCl in Dioxane (1 ml) was added to a suspension of tert-butyl 4-[(4-chloro-6-methoxyquinazolin-7-yl)oxy]piperidine-1-carboxylate (331 mg, 0.84 mmol) and 3-chloro-4-fluoroaniline (134.5 mg) in acetonitrile (10 ml). The reaction mixture was stirred and heated at 70° C. for 4 hours. The resulting precipitate was filtered hot, washed with acetonitrile and dried under vacuum to give N-(3-chloro-4-fluorophenyl)-6-methoxy-7-(piperidin-4-yloxy)quinazolin-4-amine hydrochloride (566 mg); Mass Spectrum: (M+H)+ 403.

EXAMPLE 23

(2R)-1-[4-({4-[3-Chloro-4-fluoroanilino]-6methoxyquinazolin-7-yl}oxy)piperidin-1-yl]-1-oxopropan-2-ol (Process (a))

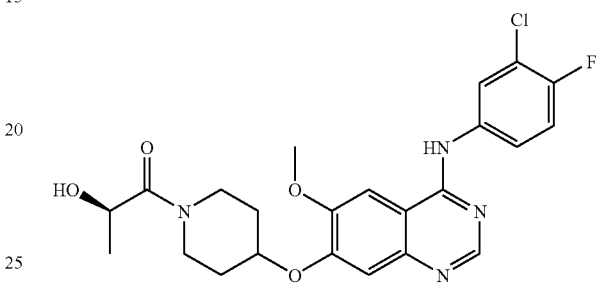

D-Lactic acid was coupled with N-(3-chloro-4-fluorophenyl)-6-methoxy-7-(piperidin-4-yloxy)quinazolin-4-amine hydrochloride using the same conditions as those described in Example 22 to give the title product; $^1$H NMR Spectrum: (DMSO $d_6$) 1.2 (d, 3H), 1.5-1.8 (m,2H), 1.9-2.15 (m, 2H), 3.1-3.50 (m, 2H+H$_2$O), 3.7-4.1 (m, 2H), 3.95 (s, 3H), 4.45 (pent, 1H), 4.8-5.8 (m, 2H), 7.32 (s, 1H), 7.45 (dd, 1H), 7.7-7.85 (m, 2H), 8.1 (dd, 1H), 8.5 (s, 1H), 9.55 (s, 1H); Mass Spectrum: (M+H)+ 475; melting point 143.6° C.

EXAMPLE 24

(2S)-1-[4-({4-[3-Bromoanilino]-6-methoxyquinazolin-7-yl}oxy)piperidin-1-yl]-1-oxopropan-2-ol (Process (a))

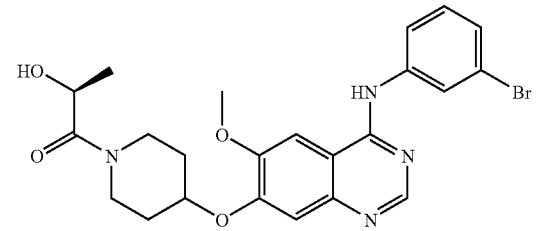

N-(3-Bromophenyl)-6-methoxy-7-(piperidin-4-yloxy)quinazolin-4-amine hydrochloride was coupled with L-(+)-lactic acid using an analogous process to that described in Example 22 to give the title product as a white powder; $^1$H NMR Spectrum: (DMSO $d_6$) 1.2 (d, 3H), 1.5-1.8 (m,2H), 1.9-2.15 (m, 2H), 3.1-3.60 (m, 2H+H$_2$O), 3.7-4.1 (m, 2H), 3.95 (s, 3H), 4.45 (m, 1H), 4.8-5.0 (m, 2H), 7.2-7.4 (m, 3H), 7.8-7.9 (m, 2H), 8.13 (s, 1H), 8.5 (s, 1H), 9.5 (s, 1H); Mass Spectrum: (M+H)+ 501,503.

The N-(3-bromophenyl)-6-methoxy-7-(piperidin-4-yloxy)quinazolin-4-amine hydrochloride starting material was prepared as follows.

tert-Butyl 4-[(4-chloro-6-methoxyquinazolin-7-yl)oxy]piperidine-1-carboxylate was coupled with 3-bromoaniline using an analogous process to that described in Example 21 (preparation of starting materials) for the preparation of N-(3-chloro-4-fluorophenyl)-6-methoxy-7-(piperidin-4-yloxy)quinazolin-4-amine hydrochloride, to give N-(3-bromophenyl)-6-methoxy-7-(piperidin-4-yloxy)quinazolin-4-amine hydrochloride; $^1$H NMR Spectrum: (DMSO $d_6$): 1.8-2.1 (m, 2H), 2.1-2.3 (m, 2H), 3.0-3.35 (m, 4H), 4.05 (s, 3H), 4.88 (m, 1H), 7.38-7.52 (m, 2H), 7.6 (s, 1H), 7.8 (d, 1H), 8.05 (s, 1H), 8.5 (s, 1H), 8.87 (s, 1H), 9.2 (bs, 2H), 11.7 (s, 1H); Mass Spectrum: (M+H)$^+$ 431.

EXAMPLE 25

(2R)-1-[4-({4-[3-Bromoanilino]-6-methoxyquinazolin-7-yl}oxy)piperidin-1-yl]-1-oxopropan-2-ol (Process (a))

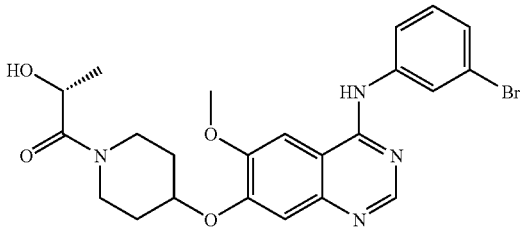

N-(3-bromophenyl)-6-methoxy-7-(piperidin-4-yloxy)quinazolin-4-amine hydrochloride was coupled with D-lactic acid using an analogous process to that described in Example 22 to give the title product as a white powder; $^1$H NMR Spectrum: (DMSO $d_6$) 1.2 (d, 3H), 1.5-1.8 (m,2H), 1.9-2.15 (m, 2H), 3.1-3.55 (m, 2H+H$_2$O), 3.7-4.1 (m, 2H), 3.95 (s, 3H), 4.43 (m, 1H), 4.8-5.0 (m, 2H), 7.2-7.4 (m, 3H), 7.8-7.9 (m, 2H), 8.15 (s, 1H), 8.5 (s, 1H), 9.5 (s, 1H); Mass Spectrum: (M+H)$^+$ 501,503.

EXAMPLE 26

(2S)-1-[4-({4-[5-Chloro-2-fluoroanilino]-6-methoxyquinazolin-7-yl}oxy)piperidin-1-yl]-1-oxopropan-2-ol (Process (a))

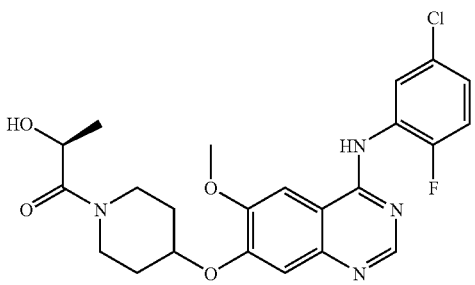

N-(5-Chloro-2-fluorophenyl)-6-methoxy-7-(piperidin-4-yloxy)quinazolin-4-amine hydrochloride was coupled with L-(+)-lactic acid using an analogous process to that described in Example 22 to give the title product as a white powder; $^1$H NMR Spectrum: (DMSO $d_6$) 1.2 (d, 3H), 1.5-1.8 (m,2H), 1.9-2.15 (m, 2H), 3.1-3.60 (m, 2H+H$_2$O), 3.7-4.1 (m, 2H), 3.95 (s, 3H), 4.45 (m, 1H), 4.8-5.0 (m, 2H), 7.3-7.45 (m, 3H), 7.7 (d, 1H), 7.85 (s, 1H), 8.5 (s, 1H), 9.95 (s, 1H); Mass Spectrum: (M+H)$^+$ 475.

The N-(5-Chloro-2-fluorophenyl)-6-methoxy-7-(piperidin-4-yloxy)quinazolin-4-amine hydrochloride starting material was prepared as follows.

tert-butyl 4-[(4-chloro-6-methoxyquinazolin-7-yl)oxy]piperidine-1-carboxylate was coupled with 2-fluoro-5-chloroaniline using an analogous process to that described in Example 22 (preparation of starting materials) for the preparation of N-(3-chloro-4-fluorophenyl)-6-methoxy-7-(piperidin-4-yloxy)quinazolin-4-amine hydrochloride, to give N-(5-chloro-2-fluorophenyl)-6-methoxy-7-(piperidin-4-yloxy)quinazolin-4-amine hydrochloride; $^1$H NMR Spectrum: (DMSO $d_6$) 1.8-2.1 (m, 2H), 2.1-2.35 (m, 2H), 3.0-3.35 (m, 4H), 4.05 (s, 3H), 4.8-5.0 (m, 1H), 7.4-7.55 (m, 2H), 7.55-7.75 (m, 2H), 8.45 (s, 1H), 8.82 (s, 1H), 9.22 (bs, 2H), 11.94 (s, 1H); Mass Spectrum: (M+H)$^+$ 403.

EXAMPLE 27

(2R)-1-[4-({4-[5-Chloro-2-fluoroanilino]-6-methoxyquinazolin-7-yl}oxy)piperidin-1-yl]-1-oxopropan-2-ol (Process (a))

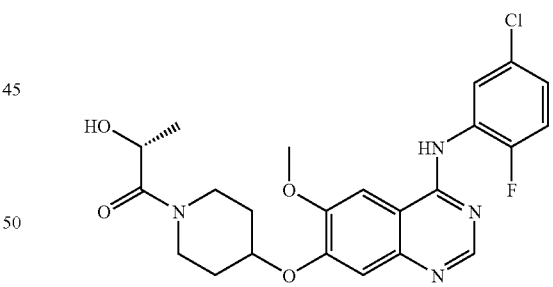

N-(5-Chloro-2-fluorophenyl)-6-methoxy-7-(piperidin-4-yloxy)quinazolin-4-amine hydrochloride was coupled with D-lactic acid using an analogous process to that described in Example 22 to give the title product as a white powder; $^1$H NMR Spectrum: (DMSO $d_6$) 1.2 (d, 3H), 1.45-1.8 (m,2H), 1.9-2.15 (m, 2H), 3.1-3.55 (m, 2H+H$_2$O), 3.7-4.1 (m, 2H), 3.95 (s, 3H), 4.45 (pent, 1H), 4.8-5.0 (m, 2H), 7.25-7.45 (m, 3H), 7.7 (dd, 1H), 7.8 (s, 1H), 8.4 (s, 1H), 9.55 (s, 1H); Mass Spectrum: (M+H)$^+$ 475.

EXAMPLE 28

(2S)-1-[4-({4-[3-Ethynylanilino]-6-methoxyquinazolin-7-yl}oxy)piperidin-1-yl]-1-oxopropan-2-ol (Process (a))

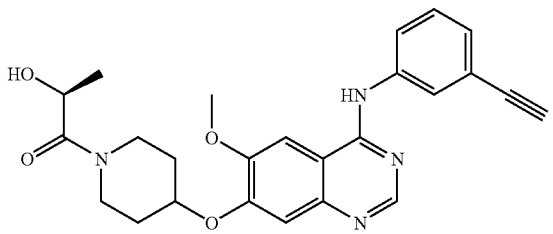

N-(3-Ethynylphenyl)-6-methoxy-7-(piperidin-4-yloxy)quinazolin-4-amine hydrochloride was coupled with L-(+)-lactic acid using an analogous process to that described in Example 22 to give the title product as a white powder; $^1$H NMR Spectrum: (DMSO $d_6$) 1.2 (d, 3H), 1.45-1.8 (m,2H), 1.9-2.15 (m, 2H), 3.1-3.55 (m, 2H+$H_2O$), 3.7-4.1 (m, 2H), 3.95 (s, 3H), 4.18 (s, 1H), 4.45 (pent, 1H), 4.8-5.0 (m, 2H), 7.2 (d, 1H), 7.33 (s, 1H), 7.39 (dd, 1H), 7.83 (s, 1H), 7.89 (d, 1H), 7.97 (s, 1H), 8.5 (s, 1H), 9.48 (s, 1H); Mass Spectrum: $(M+H)^+$ 447.

The N-(3-ethynylphenyl)-6-methoxy-7-(piperidin-4-yloxy)quinazolin-4-amine hydrochloride used as starting material was prepared as follows:

tert-butyl 4-[(4-chloro-6-methoxyquinazolin-7-yl)oxy]piperidine-1-carboxylate was coupled with 3-ethynylaniline using an analogous process to that described in Example 22 (preparation of starting materials) for the preparation of N-(3-chloro-4-fluorophenyl)-6-methoxy-7-(piperidin-4-yloxy)quinazolin-4-amine hydrochloride, to give N-(3-ethynylphenyl)-6-methoxy-7-(piperidin-4-yloxy)quinazolin-4-amine hydrochloride $^1$H NMR Spectrum: (DMSO $d_6$) 1.85-2.1 (m, 2H), 2.1-2.3 (m, 2H), 3.0-3.35 (m, 4H), 4.05 (s, 3H), 4.25 (s, 1H), 4.8-4.95 (m, 1H), 7.39 (d, 1H), 7.47 (dd, 1H), 7.6 (s, 1H), 7.8 (d, 1H), 7.89 (s, 1H), 8.5 (s, 1H), 8.83(s, 1H), 9.22 (bs, 2H), 11.68 (s, 1H); Mass Spectrum: $(M+H)^+$ 375.

EXAMPLE 29

(2R)-1-[4-({4-[(3-Ethynylanilino]-6-methoxyquinazolin-7-yl}oxy)piperidin-1-yl]-1-oxopropan-2-ol (Process (a))

N-(3-Ethynylphenyl)-6-methoxy-7-(piperidin-4-yloxy)quinazolin-4-amine hydrochloride was coupled with D-lactic acid using an analogous process to that described in Example 28 to give the title product as a white powder; $^1$H NMR Spectrum: (DMSO $d_6$) 1.2 (d, 3H), 1.45-1.8 (m,2H), 1.9-2.15 (m, 2H), 3.1-3.55 (m, 2H+$H_2O$), 3.7-4.1 (m, 2H), 3.95 (s, 3H), 4.18 (s, 1H), 4.45 (pent, 1H), 4.8-5.0 (m, 2H), 7.2 (d, 1H), 7.33 (s, 1H), 7.39 (dd, 1H), 7.83 (s, 1H), 7.89 (d, 1H), 7.97 (s, 1H), 8.48 (s, 1H), 9.47 (s, 1H); Mass Spectrum: $(M+H)^+$ 447.

EXAMPLE 30

(2S)-1-[4-({4-[3-Bromo-2-fluoroanilino]-6-methoxyquinazolin-7-yl}oxy)piperidin-1-yl]-1-oxopropan-2-ol (Process (a))

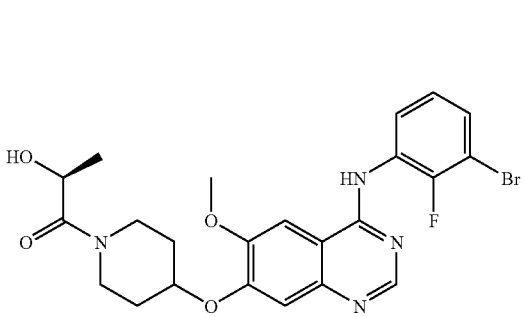

N-(3-Bromo-2-fluorophenyl)-6-methoxy-7-(piperidin-4-yloxy)quinazolin-4-amine hydrochloride was coupled with L-(+)-lactic acid using an analogous process to that described in Example 22 to give the title product as a white powder; $^1$H NMR Spectrum: (DMSO $d_6$) 1.2 (d, 3H), 1.45-1.8 (m,2H), 1.9-2.15 (m, 2H), 3.1-3.55 (m, 2H+$H_2O$), 3.7-4.1 (m, 2H), 3.95 (s, 3H), 4.45 (pent, 1H), 4.8-5.0 (m, 2H), 7.21 (dd, 1H), 7.32 (s, 1H), 7.48-7.65 (m, 2H), 7.8 (s, 1H), 8.37 (s, 1H), 9.6 (s, 1H); Mass Spectrum: $(M+H)^+$ 521.

The N-(3-Bromo-2-fluorophenyl)-6-methoxy-7-(piperidin-4-yloxy)quinazolin-4-amine hydrochloride starting material was prepared as follows:

tert-Butyl 4-[(4-chloro-6-methoxyquinazolin-7-yl)oxy]piperidine-1-carboxylate was coupled with tert-butyl (3-bromo-2-fluorophenyl)carbamate using an analogous process to that described in Example 22 (preparation of starting materials) for the preparation of N-(3-chloro-4-fluorophenyl)-6-methoxy-7-(piperidin-4-yloxy)quinazolin-4-amine hydrochloride, to give N-(3-bromo-2-fluorophenyl)-6-methoxy-7-(piperidin-4-yloxy)quinazolin-4-amine hydrochloride; $^1$H NMR Spectrum: (DMSO $d_6$) 1.85-2.1 (m, 2H), 2.1-2.32 (m, 2H), 3.0-3.35 (m, 4H), 4.02 (s, 3H), 4.83-5.0 (m, 1H), 7.3 (dd, 1H), 7.5-7.65 (m, 2H), 7.75 (dd, 1H), 8.45 (s, 1H), 8.8(s, 1H), 9.15 (bs, 2H), 11.86 (s, 1H); Mass Spectrum: $(M+H)^+$ 447.12.

The tert-butyl (3-bromo-2-fluorophenyl)carbamate starting material was prepared as follows. Triethylamine (0.6 ml) was added to a stirred solution of 3-bromo-2-fluorobenzoic acid (438 mg, 2 mmol) in tert-butanol (10 ml). Diphenyl phosphoryl azide (1 ml, 4.6 mmol) was then added and the reaction mixture was heated under reflux overnight.

The solution was evaporated to dryness and azeotroped with toluene. The residues were then purified by flash chromatography on silica eluting with ethyl acetate/i-hexane (10/90). Fractions containing the required product were combined and evaporated to give tert-butyl (3-bromo-2-fluorophenyl)carbamate as a white solid (330 mg); $^1$H NMR Spectrum: ($CDCl_3$) 1.5 (s, 9H), 6.4 (s, 1H), 7.1-7.25 (m, 1H), 7.7 (dd, 1H).

EXAMPLE 31

(2R)-1-[4-({4-[3-Bromo-2-fluoroanilino]-6-methoxyquinazolin-7-yl}oxy)piperidin-1-yl]-1-oxopropan-2-ol (Process (a))

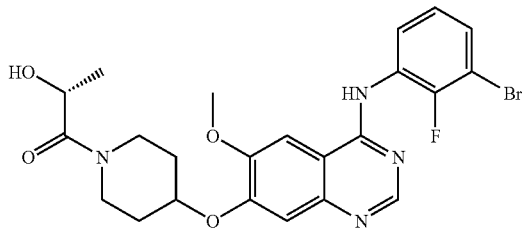

N-(3-Bromo-2-fluorophenyl)-6-methoxy-7-(piperidin-4-yloxy)quinazolin-4-amine hydrochloride was coupled with D-lactic acid using an analogous process to that described in Example 22 to give the title product as a white powder; $^1$H NMR Spectrum: (DMSO d$_6$) 1.2 (d, 3H), 1.45-1.8 (m,2H), 1.9-2.15 (m, 2H), 3.1-3.55 (m, 2H+H$_2$O), 3.7-4.1 (m, 2H), 3.95 (s, 3H), 4.45 (pent, 1H), 4.8-5.0 (m, 2H), 7.22 (dd, 1H), 7.32 (s, 1H), 7.48-7.65 (m, 2H), 7.8 (s, 1H), 8.37 (s, 1H), 9.62 (s, 1H); Mass Spectrum: (M+H)$^+$ 521.

EXAMPLE 32

(2S)-1-[4-({4-[(4-Chloro-2-fluoroanilino]-6-methoxyquinazolin-7-yl}oxy)piperidin-1-yl]-1-oxopropan-2-ol (Process (a))

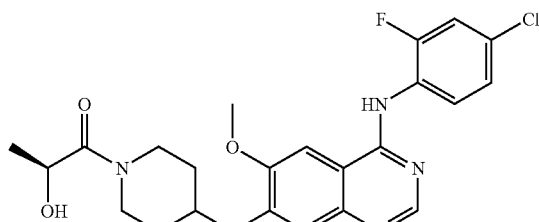

N-(4-Chloro-2-fluorophenyl)-6-methoxy-7-(piperidin-4-yloxy)quinazolin-4-amine hydrochloride was coupled with L-(+)-lactic acid using an analogous process to that described in Example 22 to give the title product as a white powder; $^1$H NMR Spectrum: (DMSO d$_6$) 1.2 (d, 3H), 1.45-1.8 (m,2H), 1.9-2.15 (m, 2H), 3.1-3.55 (m, 2H+H$_2$O), 3.7-4.1 (m, 2H), 3.93 (s, 3H), 4.44 (pent, 1H), 4.8-5.0 (m, 2H), 7.25-7.4 (m, 2H), 7.45-7.65 (m, 2H), 7.8 (s, 1H), 8.33 (s, 1H), 9.5 (s, 1H); Mass Spectrum: (M+H)$^+$ 475; melting point 149° C.

The N-(4chloro-2-fluorophenyl)-6-methoxy-7-(piperidin-4-yloxy)quinazolin-4-amine hydrochloride starting material was prepared as follows:

4-[(4-chloro-2-fluorophenyl)amino]-6-methoxyquinazolin-7-ol (5 g, 15.65 mmol, prepared as described in WO 2001/077085) was dissolved in DMA (200 ml). tert-Butyl (4-methanesulfonyloxy)piperidine-1-carboxylate (6.55 g, 23.5 mmol) and cesium fluoride (7.09 g, 46.95 mmol) were added, and the mixture was heated to 60° C. with stirring. The solvent was evaporated, and the residue was partitioned between water (200 ml) and EtOAc (200 ml). The organics were washed with water (2×100 ml) and brine (100 ml), dried over MgSO$_4$ and evaporated to give tert-butyl 4-({4-[4-chloro-2-fluoroanilino]-6-methoxyquinazolin-7-yl}oxy)piperidine-1-carboxylate (7.23 g, 91.9%); $^1$H NMR Spectrum: (DMSO-d$_6$): 1.4 (d, 9H), 1.5-1.7 (m, 2H), 1.8-2.1 (m, 2H), 3.1-3.3 (m, 2H), 3.65-3.85 (m, 2H), 3.91 (s, 3H), 4.75-4.9 (m, 1H), 7.3 (s, 1H), 7.32 (dd, 1H), 7.54 (dd, 1H), 7.57 (dd, 1H), 7.80 (s, 1H), 8.32 (s, 1H), 9.5 (s, 1H); Mass Spectrum: (M+H)$^+$ 503.

A solution of 4M hydrogen chloride in dioxane (100 ml) was added to a stirred solution of tert-butyl 4-({4-[4-chloro-2-fluoroanilino]-6-methoxyquinazolin-7-yl}oxy)piperidine-1-carboxylate (7.23 g, 14.4 mmol) in acetonitrile (100 ml). The reaction mixture was heated at 70° C. for 1 hour then concentrated to ½ volume. The resulting precipitate was collected by filtration, washed with acetonitrile and dried under vacuum to give N-(4-chloro-2-fluorophenyl)-6-methoxy-7-(piperidin-4-yloxy)quinazolin-4-amine hydrochloride as a white solid (4.42 g, 76.3%); $^1$H NMR Spectrum: (DMSO-d$_6$): 1.90-2.10 (m, 2H), 2.10-2.32 (m, 2H), 3.00-3.35 (m, 4H), 4.02 (s, 3H), 4.90 (m, 1H), 7.36-7.50 (m, 1H), 7.50-7.70 (m, 3H), 8.48 (s, 1H), 8.80(s, 1H), 9.30(bs, 2H), 11.90 (bs, 1H); Mass Spectrum: (M+H)$^+$ 403.

EXAMPLE 33

(2R)-1-[4-({4-[4-chloro-2-fluoroanilino]-6-methoxyquinazolin-7-yl}oxy)piperidin-1-yl]-1-oxopropan-2-ol (Process)a))

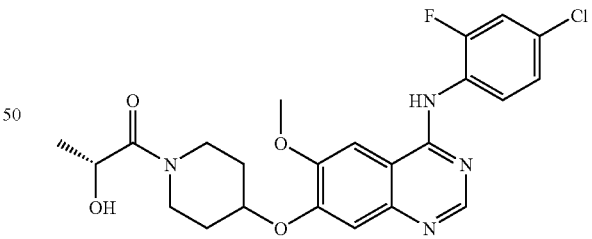

N-(4-Chloro-2-fluorophenyl)-6-methoxy-7-(piperidin-4-yloxy)quinazolin-4-amine hydrochloride was coupled with D-lactic acid using an analogous process to that described in Example 22 to give the title product as a white powder; $^1$H NMR Spectrum: (DMSO d$_6$) 1.2 (d, 3H), 1.45-1.8 (m,2H), 1.9-2.15 (m, 2H), 3.1-3.55 (m, 2H+H$_2$O), 3.7-4.1 (m, 2H), 3.93 (s, 3H), 4.43 (pent, 1H), 4.80-4.98 (m, 2H), 7.25-7.4 (m, 2H), 7.45-7.65 (m, 2H), 7.8 (s, 1H), 8.35 (s, 1H), 9.5 (s, 1H); Mass Spectrum: (M+H)$^+$ 475; melting point 118° C.

EXAMPLE 34

N-(3-chloro-2-fluorophenyl)-6-methoxy-7-{[1-(1-methyl-L-prolyl)piperidin-4-yl]oxy}quinazolin-4-amine (Process) a))

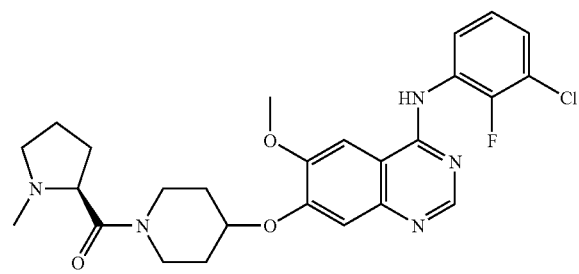

N-(3-Chloro-2-fluorophenyl)-6-methoxy-7-(piperidin-4-yloxy)quinazolin-4-amine hydrochloride was coupled with N-methyl-L-proline using an analogous process to that described in Example 2 to give the title product as a white powder; $^1$H NMR Spectrum: (DMSO $d_6$) 1.4-1.9 (m,5H), 1.9-2.20 (m, 7H), 2.9-3.05 (m, 1H), 3.05-3.25 (m, 2H), 3.25-3.65 (m, 1H+H$_2$O), 3.75-4.2 (m, 2H), 3.95 (s, 3H), 4.75-5.0 (m, 1H), 7.2-7.4 (m, 2H), 7.4-7.6 (m, 2H), 7.8 (s, 1H), 8.37 (s, 1H), 9.65 (s, 1H); Mass Spectrum: (M+H)$^+$ 514; melting point 193° C.

EXAMPLE 35

(2S)-1-[4-({4-[3-chloro-2-fluoroanilino]-6-methoxyquinazolin-7-yl}oxy)piperidin-1-yl]-1-oxopropan-2-ol (Process (b))

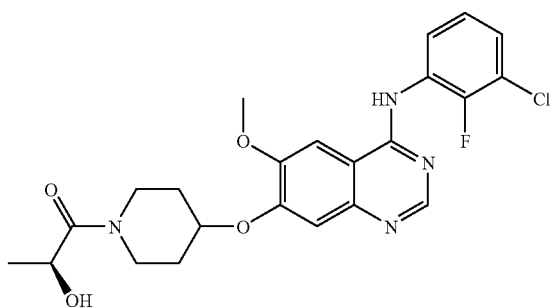

N-(3-Chloro-2-fluorophenyl)-6-methoxy-7-(piperidin-4-yloxy)quinazolin-4-amine (500 mg, 1.05 mmol) and 4-dimethylaminopyridine (128 mg, 1.05 mmol) were stirred in acetonitrile (2.5 ml) and diisopropylethylamine (0.366 ml, 2.10 mmol) was added. The mixture was cooled to 0° C. and a solution of (S)-(−)-2-acetoxypropionyl chloride (0.166 ml, 1.31 mmol) in acetonitrile (0.5 ml) was added drop-wise. The reaction mixture was then stirred at this temperature for 0.5 hours. Water (1.0 ml) and potassium hydroxide (0.641 ml of a 49% w/w solution in water) were added and the mixture stirred at room temperature over night. The layers were separated and the organic layer diluted with ethyl acetate (2.5 ml). Water was added followed by glacial acetic acid (0.210 ml). The mixture was stirred and partitioned. The organics were dried over magnesium sulphate, filtered and concentrated under reduced pressure to give the title product (215 mg, 43%) as a white solid; $^1$H NMR Spectrum: (DMSO $d_6$) 1.19 (d, 3H), 1.48-1.75 (m, 2H), 1.94-2.13 (m, 2H), 3.21-3.53 (m, 2H), 3.93 (s, 3H), 3.78-4.06 (m, 2H), 4.40-4.52 (m, 1H), 4.83-4.99 (m, 2H), 7.28 (dd, 1H), 7.33 (s, 1H), 7.42-7.55 (m, 2H), 7.81 (s, 1H), 8.36 (s, 1H), 9.62 (s, 1H); Mass Spectrum: (M+H)$^+$ 475.

EXAMPLE 36

N-(3-Chloro-2-fluorophenyl)-6-methoxy-7-{[-(3-methoxypropanoyl)piperidin-4-yl]oxy}quinazolin-4-amine (Process (b))

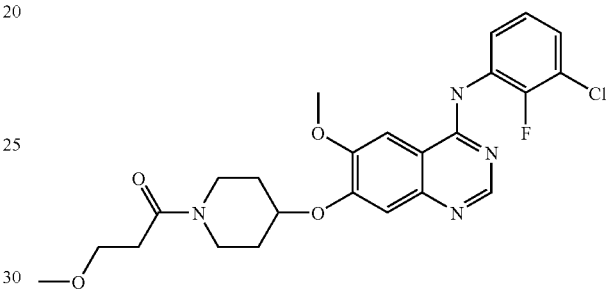

N-(3-Chloro-2-fluorophenyl)-6-methoxy-7-(piperidin-4-yloxy)quinazolin-4-amine was coupled with 3-methoxypropionyl chloride using an analogous process to that described in Example 35 except that following addition of the water and potassium hydroxide at the completion of the coupling reaction, the layers were separated directly and the product was extracted and isolated as described in Example 35 to give the title product; $^1$H NMR Spectrum: (DMSO $d_6$) 1.59 (m, 1H); 1.69 (m, 1H); 2.04 (m, 2H); 2.61 (t, 2H); 3.21 (s, 3H); 3.26 (m, 1H); 3.41 (m, 1H); 3.57 (t, 2H); 3.77 (m, 1H); 3.95 (m, 4H); 4.90 (m, 1H); 7.29 (m, 1H); 7.35 (s, 1H); 7.48 (m, 1H); 7.53 (m, 1H); 7.83 (s, 1H); 8.39 (s, 1H); 9.63 (s, 1H). Mass Spectrum: (M+H)$^+$ 489.

EXAMPLE 37

Pharmaceutical Compositions

The following illustrates representative pharmaceutical dosage forms of the invention as defined herein (the active ingredient being termed "Compound X") which may be prepared, for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Injection I | (50 mg/ml) |
|---|---|
| Compound X | 5.0% w/v |
| 1M Sodium hydroxide solution | 15.0% v/v |

-continued

| | |
|---|---|
| 0.1M Hydrochloric acid (to adjust pH to 7.6) | |
| Polyethylene glycol 400 | 4.5% w/v |
| Water for injection to 100%. | |

The above compositions may be prepared by conventional procedures well known in the pharmaceutical art. For example, Tablet I may be prepared by blending the components together and compressing the mixture into a tablet.

The invention claimed is:

1. A compound which is (2S)-1-[4-({4-[3-chloro-2-fluoroanilino]-6-methoxyquinazolin-7-yl}oxy)piperidin-1-yl]-1-oxopropan-2-ol, or a pharmaceutically acceptable salt, or a pharmaceutically acceptable ester thereof.

2. The compound according to claim 1 wherein said compound is (2S)-1-[4-({4-[3-chloro-2-fluoroanilino]-6-methoxyquinazolin-7-yl}oxy)piperidin-1-yl]-1-oxopropan-2-ol.

3. The compound according to claim 1 wherein the compound is a pharmaceutically acceptable salt of (2S)-1-[4-({4-[3-chloro-2-fluoroanilino]-6-methoxyquinazolin-7-yl}oxy)piperidin-1-yl]-1-oxopropan-2-ol.

4. A pharmaceutical composition which comprises (2S)-1-[4-({4-[3-chloro-2-fluoroanilino]-6-methoxyquinazolin-7-yl}oxy)piperidin-1-yl]-1-oxopropan-2-ol, or a pharmaceutically acceptable salt, or a pharmaceutically acceptable ester thereof, in association with a pharmaceutically acceptable diluent or carrier.

5. The pharmaceutical composition according to claim 4, wherein said composition comprises (2S)-1-[4-({4-[3-chloro-2-fluoroanilino]-6-methoxyquinazolin-7-yl}oxy)piperidin-1-yl]-1-oxopropan-2-ol, in association with a pharmaceutically acceptable diluent or carrier.

6. The pharmaceutical composition according to claim 4, wherein composition comprises a pharmaceutically acceptable salt of (2S)-1-[4-({4-[3-chloro-2-fluoroanilino]-6-methoxyquinazolin-7-yl}oxy)piperidin-1-yl]-1-oxopropan-2-ol, in association with a pharmaceutically acceptable diluent or carrier.

7. A method for treating a cancer selected from a group consisting of lung cancer, non-small cell lung cancer, breast cancer, head & neck cancer, gastric cancer and colorectal cancer, in a warm-blooded animal in need of such treatment, which comprises administering to said animal an effective amount of (2S)-1-[4-({4-[3-chloro-2-fluoroanilino]-6-methoxyquinazolin-7-yl}oxy)piperidin-1-yl]-1-oxopropan-2-ol, or a pharmaceutically acceptable salt, or a pharmaceutically acceptable ester thereof.

8. The method according to claim 7, wherein said treatment comprises administering to said animal an effective amount of (2S)-1-[4-({4-[3-chloro-2-fluoroanilino]-6-methoxyquinazolin-7-yl}oxy)piperidin-1-yl]-1-oxopropan-2-ol.

9. The method according to claim 7, wherein said treatment comprises administering to said animal an effective amount of a pharmaceutically acceptable salt of (2S)-1-[4-({4-[3-chloro-2-fluoroanilino]-6-methoxyquinazolin-7-yl}oxy)piperidin-1-yl]-1-oxopropan-2-ol.

10. The method according to claim 7 or 8 wherein said cancer is lung cancer.

11. The method according to claim 7 or 8 wherein said cancer is non-small cell lung cancer.

12. The method according to claim 7 or 8 wherein said cancer is breast cancer.

13. The method according to claim 7 or 8 wherein said cancer is head and neck cancer.

14. The method according to claim 7 or 8 wherein said cancer is gastric cancer.

15. The method according to claim 7 or 8 wherein said cancer is colorectal cancer.

16. The method according to claim 7 or 8 wherein said cancer is ovarian cancer.

17. The method according to claim 7 or 8 further comprising the simultaneous, sequential or separate administration to said animal of an effective amount of an additional anti-tumour agent.

18. A method for treating psoriasis in a warm-blooded animal in need of such treatment, which comprises administering to said animal an effective amount of (2S)-1-[4-({4-[3-chloro-2-fluoroanilino]-6-methoxyquinazolin-7-yl}oxy)piperidin-1-yl]-1-oxopropan-2-ol, or a pharmaceutically acceptable salt, or a pharmaceutically acceptable ester thereof.

* * * * *